(12) United States Patent
Clausen

(10) Patent No.: US 10,195,057 B2
(45) Date of Patent: Feb. 5, 2019

(54) TRANSFEMORAL PROSTHETIC SYSTEMS AND METHODS FOR OPERATING THE SAME

(75) Inventor: Arinbjorn Viggo Clausen, Reykjavik (IS)

(73) Assignee: Össur hf., Reykjavik (IS)

(*) Notice: Subject to any disclaimer, the term of this patent is extended or adjusted under 35 U.S.C. 154(b) by 289 days.

(21) Appl. No.: 13/244,010

(22) Filed: Sep. 23, 2011

(65) Prior Publication Data

US 2012/0016492 A1  Jan. 19, 2012

Related U.S. Application Data

(60) Division of application No. 12/409,336, filed on Mar. 23, 2009, now Pat. No. 8,057,550, which is a
(Continued)

(51) Int. Cl.
*A61F 2/68* (2006.01)
*A61F 2/70* (2006.01)
(Continued)

(52) U.S. Cl.
CPC .................. *A61F 2/68* (2013.01); *A61F 2/60* (2013.01); *A61F 2/64* (2013.01); *A61F 2/6607* (2013.01); *A61F 2/72* (2013.01); *A61F 2002/5004* (2013.01); *A61F 2002/5006* (2013.01); *A61F 2002/5018* (2013.01); *A61F 2002/607* (2013.01); *A61F 2002/701* (2013.01);
(Continued)

(58) Field of Classification Search
CPC ...... A61F 2/60; A61F 2/68; A61F 2/72; A61F 2002/704; A61F 2/70; A61F 2002/701

USPC ................................................... 623/27
See application file for complete search history.

(56) References Cited

U.S. PATENT DOCUMENTS 909,859 A    1/1909 Apgar
2,475,373 A    7/1949 Catranis
(Continued)

FOREIGN PATENT DOCUMENTS

CH    543277    12/1973
CN    2043873    9/1989
(Continued)

OTHER PUBLICATIONS

Abbas, et al., Neural Network Control of Functional Neuromuscular Stimulation Systems: Computer Stimulation Studies, 1995.
(Continued)

*Primary Examiner* — Jacqueline Woznicki
(74) *Attorney, Agent, or Firm* — Knobbe Martens Olson & Bear LLP

(57) ABSTRACT

Certain embodiments of the invention relate to increasing the functionality of a transfemoral prosthetic device. In one embodiment, the transfemoral prosthetic device is configured such that the prosthetic knee maintains a load consistent with a healthy knee walking on level ground, while the prosthetic ankle adjusts for the incline or decline. In certain embodiments, adjustments, such as a toe lift function, are automatically performed after about three strides of the transfemoral prosthetic device user and/or when each of the strides has a stride speed of at least about 0.55 meters/second.

21 Claims, 29 Drawing Sheets

| Possible Transits: From State to State | Stance | Level Ground Walking | Ascending Stairs | Descending Stairs | Incline (up) | Decline | Sitting Down | Sitting | Standing Up | Adjust Heel Height |
|---|---|---|---|---|---|---|---|---|---|---|
| Stance | N/A | Toe Clearance | −10° | −10° | −2.5°, −5° | +2.5°, +5° | No Action | | | Set Heel Height |
| Level Ground Walking | No Action | N/A | −10° | −10° | −2.5°, −5° | +2.5°, +5° | | | | |
| Ascending Stairs | User Setpoint | Toe Clearance | N/A | −10° | −2.5°, −5° | | | | | |
| Descending Stairs | User Setpoint | Toe Clearance | −10° | N/A | −2.5°, −5° | +2.5°, +5° | | | | |
| Incline (up) | No Action | Toe Clearance | −10° | | N/A | +2.5°, +5° | | | | |
| Decline | No Action | Toe Clearance | | −10° | −2.5°, −5° | N/A | | | | |
| Sitting Down | | | | | | | N/A | Relax Ankle | | |
| Sitting | | | | | | | | N/A | User Setpoint | Set Heel Height |
| Standing Up | User Setpoint | Toe Clearance | | | | | | | N/A | |
| Adjust Heel Height | User Setpoint | | | | | | User Setpoint | User Setpoint | | N/A |

Related U.S. Application Data continuation-in-part of application No. 11/355,047, filed on Feb. 15, 2006, said application No. 12/409,336 is a continuation-in-part of application No. 11/056,344, filed on Feb. 11, 2005, now Pat. No. 7,811,334.

(60) Provisional application No. 61/039,055, filed on Mar. 24, 2008, provisional application No. 60/679,953, filed on May 10, 2005, provisional application No. 60/653,717, filed on Feb. 16, 2005, provisional application No. 60/588,232, filed on Jul. 15, 2004, provisional application No. 60/544,259, filed on Feb. 12, 2004.

(51) Int. Cl.
*A61F 2/60* (2006.01)
*A61F 2/64* (2006.01)
*A61F 2/66* (2006.01)
*A61F 2/72* (2006.01)
*A61F 2/50* (2006.01)
*A61F 2/76* (2006.01)

(52) U.S. Cl.
CPC ... *A61F 2002/704* (2013.01); *A61F 2002/705* (2013.01); *A61F 2002/763* (2013.01); *A61F 2002/764* (2013.01); *A61F 2002/768* (2013.01); *A61F 2002/769* (2013.01); *A61F 2002/7625* (2013.01); *A61F 2002/7635* (2013.01); *A61F 2002/7685* (2013.01)

(56) References Cited

U.S. PATENT DOCUMENTS

| | | |
|---|---|---|
| 2,568,051 A | 9/1951 | Catranis |
| 2,619,652 A | 12/1952 | Vesper |
| 2,843,853 A | 7/1958 | Mauch |
| 2,859,451 A | 11/1958 | Mauch |
| 3,316,558 A | 5/1967 | Mortensen |
| 3,417,409 A | 12/1968 | Prahl |
| 3,501,776 A | 3/1970 | Beeker et al. |
| 3,589,134 A | 6/1971 | Hackmann |
| 3,659,294 A | 5/1972 | Glabiszewski |
| 3,701,368 A | 10/1972 | Stern |
| 3,791,375 A | 2/1974 | Pfeifer |
| 3,820,168 A | 6/1974 | Horvath |
| 3,866,246 A | 2/1975 | Seamone et al. |
| 3,871,032 A | 3/1975 | Wolfgang |
| 3,953,900 A | 5/1976 | Thompson |
| 3,995,324 A | 12/1976 | Burch |
| 4,005,496 A | 2/1977 | Wilkes |
| 4,023,215 A | 5/1977 | Moore |
| 4,030,141 A | 6/1977 | Graupe |
| 4,064,569 A | 12/1977 | Campbell |
| 4,065,815 A | 1/1978 | Sen-Jung |
| 4,100,918 A | 7/1978 | Glancy |
| 4,179,759 A | 12/1979 | Smith |
| 4,209,860 A | 7/1980 | Graupe |
| 4,212,087 A | 7/1980 | Mortensen |
| 4,310,932 A | 1/1982 | Nader et al. |
| 4,314,379 A | 2/1982 | Tanie et al. |
| 4,354,676 A | 10/1982 | Ariel |
| 4,363,498 A | 12/1982 | Biermann et al. |
| 4,370,977 A | 2/1983 | Mauldin et al. |
| 4,386,891 A | 6/1983 | Riefel et al. |
| 4,387,472 A | 6/1983 | Wilson |
| 4,433,679 A | 2/1984 | Mauldin et al. |
| 4,458,367 A | 7/1984 | May |
| 4,488,320 A | 12/1984 | Wilson |
| 4,518,307 A | 5/1985 | Bloch |
| 4,521,924 A | 6/1985 | Jacobsen et al. |
| 4,556,956 A | 12/1985 | Dickenson et al. |
| 4,558,704 A | 12/1985 | Petrofsky |
| 4,569,352 A | 2/1986 | Petrofsky et al. |
| 4,578,083 A | 3/1986 | Williams |
| 4,579,558 A | 4/1986 | Ramer |
| 4,600,357 A | 7/1986 | Coules |
| 4,602,619 A | 7/1986 | Wolf et al. |
| 4,617,920 A | 10/1986 | Carsalade |
| 4,649,934 A | 3/1987 | Fraser et al. |
| 4,652,266 A | 3/1987 | Truesdell |
| 4,657,000 A | 4/1987 | Hepburn |
| 4,657,470 A | 4/1987 | Clarke et al. |
| 4,685,926 A | 8/1987 | Haupt |
| 4,685,927 A | 8/1987 | Haupt |
| 4,711,242 A | 12/1987 | Petrofsky |
| 4,711,450 A | 12/1987 | McArthur |
| 4,726,404 A | 2/1988 | Haber et al. |
| 4,730,625 A | 3/1988 | Fraser et al. |
| 4,760,850 A | 8/1988 | Phillips et al. |
| 4,770,662 A | 9/1988 | Giampapa |
| 4,776,326 A | 10/1988 | Roung et al. |
| 4,776,852 A | 10/1988 | Rubic |
| 4,790,522 A | 12/1988 | Drutchas |
| 4,795,474 A | 1/1989 | Horvath |
| 4,805,455 A | 2/1989 | DelGiorno et al. |
| 4,808,187 A | 2/1989 | Patterson et al. |
| 4,814,661 A | 3/1989 | Ratzlaff et al. |
| 4,838,251 A | 6/1989 | Chignon et al. |
| 4,843,921 A | 7/1989 | Kremer |
| 4,854,428 A | 8/1989 | Horvath |
| 4,865,024 A | 9/1989 | Hensley et al. |
| 4,872,803 A | 10/1989 | Asakawa |
| 4,876,944 A | 10/1989 | Wilson et al. |
| 4,878,913 A | 11/1989 | Aebischer et al. |
| 4,892,554 A | 1/1990 | Robinson |
| 4,893,648 A | 1/1990 | Horvath |
| 4,919,418 A | 4/1990 | Miller |
| 4,928,676 A | 5/1990 | Pansiera |
| 4,944,755 A | 7/1990 | Hennequin et al. |
| 4,958,705 A | 9/1990 | Horvath |
| 4,989,161 A | 1/1991 | Oaki |
| 4,994,086 A | 2/1991 | Edwards |
| 5,020,790 A | 6/1991 | Beard et al. |
| 5,033,291 A | 7/1991 | Podoloff et al. |
| 5,044,360 A | 9/1991 | Janke |
| 5,062,673 A | 11/1991 | Mimura |
| 5,062,856 A | 11/1991 | Sawamura et al. |
| 5,062,857 A | 11/1991 | Berringer |
| 5,086,785 A | 2/1992 | Gentile et al. |
| 5,092,902 A | 3/1992 | Adams et al. |
| 5,101,472 A | 3/1992 | Repperger |
| 5,112,296 A | 5/1992 | Beard et al. |
| 5,112,356 A | 5/1992 | Harris et al. |
| 5,139,525 A | 8/1992 | Kristinsson |
| 5,153,496 A | 10/1992 | LaForge |
| 5,156,630 A | 10/1992 | Rappoport et al. |
| 5,174,168 A | 12/1992 | Takagi et al. |
| 5,181,931 A | 1/1993 | Van de Veen |
| 5,197,488 A | 3/1993 | Kovacevic |
| 5,201,772 A | 4/1993 | Maxwell |
| 5,217,500 A | 6/1993 | Phillips |
| 5,219,365 A | 6/1993 | Sabolich |
| 5,230,672 A | 7/1993 | Brown et al. |
| 5,246,465 A | 9/1993 | Rincoe et al. |
| 5,252,102 A | 10/1993 | Singer et al. |
| 5,252,901 A | 10/1993 | Ozawa et al. |
| 5,253,656 A | 10/1993 | Rincoe |
| 5,265,890 A | 11/1993 | Balsells |
| 5,277,281 A | 1/1994 | Carlson et al. |
| 5,282,460 A | 2/1994 | Boldt |
| 5,284,330 A | 2/1994 | Carlson et al. |
| 5,314,498 A | 5/1994 | Gramnas |
| 5,323,650 A | 6/1994 | Fullen et al. |
| 5,327,790 A | 7/1994 | Levin et al. |
| 5,336,269 A | 8/1994 | Smits |
| 5,357,696 A | 10/1994 | Gray et al. |
| 5,376,128 A | 12/1994 | Bozeman, Jr. |
| 5,376,133 A | 12/1994 | Gramnas |
| 5,376,137 A | 12/1994 | Shorter et al. |
| 5,376,138 A | 12/1994 | Bouchard et al. |
| 5,376,141 A | 12/1994 | Phillips |

(56) References Cited

U.S. PATENT DOCUMENTS

| | | |
|---|---|---|
| 5,382,373 A | 1/1995 | Carlson et al. |
| 5,383,939 A | 1/1995 | James |
| 5,394,132 A | 2/1995 | Poil |
| 5,397,287 A | 3/1995 | Lindfors |
| 5,398,917 A | 3/1995 | Carlson et al. |
| 5,405,407 A | 4/1995 | Kodama et al. |
| 5,405,409 A | 4/1995 | Knoth |
| 5,405,410 A | 4/1995 | Arbogast et al. |
| 5,405,510 A | 4/1995 | Betts |
| 5,408,873 A | 4/1995 | Schmidt et al. |
| 5,413,611 A * | 5/1995 | Haslam et al. .......... 623/25 |
| 5,422,558 A | 6/1995 | Stewart |
| 5,425,780 A | 6/1995 | Flatt et al. |
| 5,430,643 A | 7/1995 | Seraji |
| 5,437,611 A | 8/1995 | Stern |
| 5,443,521 A | 8/1995 | Knoth et al. |
| 5,443,524 A | 8/1995 | Sawamura et al. |
| 5,443,528 A | 8/1995 | Allen |
| 5,455,497 A | 10/1995 | Hirose et al. |
| 5,472,412 A | 12/1995 | Knoth |
| 5,476,441 A | 12/1995 | Durfee et al. |
| 5,484,389 A | 1/1996 | Stark et al. |
| 5,504,415 A | 4/1996 | Podrazhansky et al. |
| D372,536 S | 8/1996 | Grifka |
| 5,545,232 A | 8/1996 | Van de Veen |
| 5,545,233 A | 8/1996 | Fitzlaff |
| 5,551,525 A | 9/1996 | Pack et al. |
| 5,563,458 A | 10/1996 | Ericson |
| 5,566,479 A | 10/1996 | Gray et al. |
| 5,571,205 A | 11/1996 | James |
| 5,571,210 A | 11/1996 | Lindh |
| 5,571,212 A | 11/1996 | Cornelius |
| 5,571,213 A | 11/1996 | Allen |
| 5,583,476 A | 12/1996 | Langford et al. |
| 5,586,557 A | 12/1996 | Nelson et al. |
| 5,624,389 A | 4/1997 | Zepf |
| 5,642,096 A | 6/1997 | Leyerer et al. |
| 5,645,590 A | 7/1997 | Van de Veen |
| 5,645,752 A | 7/1997 | Weiss et al. |
| 5,650,704 A | 7/1997 | Pratt et al. |
| 5,656,915 A | 8/1997 | Eaves |
| D383,542 S | 9/1997 | Wellershaus et al. |
| 5,662,693 A | 9/1997 | Johnson et al. |
| 5,670,077 A | 9/1997 | Carlson et al. |
| 5,678,448 A | 10/1997 | Fullen et al. |
| 5,683,615 A | 11/1997 | Munoz |
| 5,695,527 A | 12/1997 | Allen |
| 5,704,945 A | 1/1998 | Wagner et al. |
| 5,704,946 A | 1/1998 | Greene |
| 5,711,746 A | 1/1998 | Carlson |
| 5,728,170 A | 3/1998 | Becker et al. |
| 5,728,174 A | 3/1998 | Fitzlaff |
| 5,746,774 A | 5/1998 | Kramer et al. |
| 5,749,533 A | 5/1998 | Daniels |
| 5,755,812 A | 5/1998 | Becker et al. |
| 5,755,813 A | 5/1998 | Krukenberg |
| 5,779,735 A | 7/1998 | Molino |
| 5,800,561 A | 9/1998 | Rodriquez |
| 5,800,568 A | 9/1998 | Atkinson et al. |
| 5,810,752 A | 9/1998 | Grifka |
| 5,823,309 A | 10/1998 | Gopalswamy et al. |
| D402,368 S | 12/1998 | Holzapfel |
| 5,842,547 A | 12/1998 | Carlson et al. |
| D407,490 S | 3/1999 | Zepf et al. |
| 5,888,212 A | 3/1999 | Petrofsky et al. |
| 5,888,213 A | 3/1999 | Sears et al. |
| 5,888,236 A | 3/1999 | Van de Veen |
| 5,888,239 A | 3/1999 | Wellershaus et al. |
| 5,888,246 A | 3/1999 | Gow |
| 5,893,891 A | 4/1999 | Zahedi |
| 5,895,430 A | 4/1999 | O'Connor |
| 5,899,869 A | 5/1999 | Barrack, Jr. et al. |
| 5,900,184 A | 5/1999 | Weiss et al. |
| 5,906,767 A | 5/1999 | Karol et al. |
| 5,919,149 A | 7/1999 | Allum |
| 5,929,332 A | 7/1999 | Brown |
| 5,941,913 A | 8/1999 | Woolnough et al. |
| 5,878,851 A | 9/1999 | Carlson et al. |
| 5,947,238 A | 9/1999 | Jolly et al. |
| 5,948,021 A | 9/1999 | Radcliffe |
| 5,954,621 A | 9/1999 | Joutras et al. |
| 5,955,667 A | 9/1999 | Fyfe |
| 5,957,981 A | 9/1999 | Grammas |
| 5,960,918 A | 10/1999 | Moser et al. |
| 5,967,273 A | 10/1999 | Hampton |
| 5,972,035 A | 10/1999 | Blatchford |
| 5,982,156 A | 11/1999 | Weimer et al. |
| 5,984,972 A | 11/1999 | Huston et al. |
| 5,998,930 A | 12/1999 | Upadhyay et al. |
| 6,006,412 A | 12/1999 | Bergmann et al. |
| 6,007,582 A | 12/1999 | May |
| RE36,521 E | 1/2000 | Hiemisch |
| 6,027,664 A | 2/2000 | Weiss et al. |
| 6,029,374 A | 2/2000 | Herr et al. |
| 6,039,091 A | 3/2000 | Rodgers et al. |
| 6,061,577 A | 5/2000 | Andrieu et al. |
| 6,080,123 A | 6/2000 | Pansiera |
| 6,086,616 A | 7/2000 | Okuda et al. |
| 6,091,977 A | 7/2000 | Tarjan et al. |
| 6,093,162 A | 7/2000 | Fairleigh et al. |
| 6,095,486 A | 8/2000 | Ivers et al. |
| 6,104,759 A | 8/2000 | Carkner et al. |
| 6,113,642 A | 9/2000 | Petrofsky et al. |
| 6,117,177 A | 9/2000 | Chen et al. |
| 6,122,960 A | 9/2000 | Hutchings et al. |
| 6,129,690 A | 10/2000 | Hamlin et al. |
| 6,129,766 A | 10/2000 | Johnson et al. |
| 6,139,586 A | 10/2000 | Wagner et al. |
| 6,164,967 A | 12/2000 | Sale |
| 6,165,226 A | 12/2000 | Wagner |
| 6,168,634 B1 | 1/2001 | Schmitz |
| 6,183,425 B1 | 2/2001 | Whalen et al. |
| 6,187,051 B1 | 2/2001 | van de Veen |
| 6,187,052 B1 | 2/2001 | Molino et al. |
| D439,339 S | 3/2001 | Sawatzki |
| 6,195,921 B1 | 3/2001 | Truong |
| 6,206,932 B1 | 3/2001 | Johnson |
| 6,206,933 B1 | 3/2001 | Shorter et al. |
| 6,206,934 B1 | 3/2001 | Phillips |
| 6,241,775 B1 | 6/2001 | Blatchford |
| D446,304 S | 8/2001 | Sawatzki |
| 6,301,964 B1 | 10/2001 | Fyfe et al. |
| 6,342,076 B1 | 1/2002 | Lundborg |
| 6,350,286 B1 | 2/2002 | Atkinson et al. |
| 6,352,144 B1 | 3/2002 | Brooks |
| 6,361,570 B1 | 3/2002 | Gow |
| 6,373,152 B1 | 4/2002 | Wang et al. |
| 6,378,190 B2 | 4/2002 | Akeel |
| 6,379,393 B1 | 4/2002 | Mavroidis et al. |
| 6,395,193 B1 | 5/2002 | Kintz et al. |
| 6,409,695 B1 | 6/2002 | Connelly |
| 6,423,098 B1 | 7/2002 | Biedermann |
| 6,425,925 B1 | 7/2002 | Grundei |
| 6,430,843 B1 | 8/2002 | Potter et al. |
| 6,436,149 B1 | 8/2002 | Rincoe |
| 6,443,993 B1 | 9/2002 | Koniuk |
| 6,443,995 B1 | 9/2002 | Townsend et al. |
| 6,451,481 B1 | 9/2002 | Lee et al. |
| 6,485,519 B2 | 11/2002 | Meyers et al. |
| 6,494,039 B2 | 12/2002 | Pratt et al. |
| 6,500,210 B1 | 12/2002 | Sabolich et al. |
| 6,513,381 B2 | 2/2003 | Fyfe et al. |
| 6,517,585 B1 | 2/2003 | Zahedi et al. |
| 6,517,858 B1 | 2/2003 | Le Moel et al. |
| 6,522,266 B1 | 2/2003 | Soehren et al. |
| 6,537,322 B1 | 3/2003 | Johnson et al. |
| 6,543,987 B2 | 4/2003 | Ehrat |
| 6,587,728 B2 | 7/2003 | Fang et al. |
| 6,589,287 B2 | 7/2003 | Lundborg |
| 6,599,439 B2 | 7/2003 | Iregar et al. |
| 6,602,295 B1 | 8/2003 | Doddroe et al. |
| 6,610,101 B2 | 8/2003 | Herr et al. |
| 6,613,097 B1 | 9/2003 | Cooper |
| 6,645,252 B2 | 11/2003 | Asai et al. |

(56) References Cited

U.S. PATENT DOCUMENTS

| | | |
|---|---|---|
| 6,663,673 B2 | 12/2003 | Christensen |
| 6,671,531 B2 | 12/2003 | Al-Ali et al. |
| 6,679,920 B2 | 1/2004 | Biedermann et al. |
| 6,695,885 B2 | 2/2004 | Shulman et al. |
| 6,704,024 B2 | 3/2004 | Robotham et al. |
| 6,704,582 B2 | 3/2004 | Le-Faucheur et al. |
| 6,719,806 B1 | 4/2004 | Zahedi et al. |
| 6,719,807 B2 | 4/2004 | Harris |
| 6,733,180 B2 | 5/2004 | Nakamura |
| 6,740,123 B2 | 5/2004 | Davalli et al. |
| 6,740,125 B2 | 5/2004 | Mosler |
| 6,743,260 B2 | 6/2004 | Townsend et al. |
| 6,755,870 B1 | 6/2004 | Biedermann et al. |
| 6,761,743 B1 | 7/2004 | Johnson |
| 6,764,520 B2 | 7/2004 | Deffenbaugh et al. |
| 6,764,521 B2 | 7/2004 | Molino et al. |
| 6,767,370 B1 | 7/2004 | Mosler et al. |
| 6,770,045 B2 | 8/2004 | Naft et al. |
| 6,780,343 B2 | 8/2004 | Hata et al. |
| 6,805,677 B2 | 10/2004 | Simmons |
| 6,811,571 B1 | 11/2004 | Phillips |
| 6,813,582 B2 | 11/2004 | Levi et al. |
| 6,824,569 B2 | 11/2004 | Okediji |
| D499,487 S | 12/2004 | Bedard et al. |
| D501,925 S | 2/2005 | Bedard et al. |
| 6,855,170 B2 | 2/2005 | Gramnas |
| 6,863,695 B2 | 3/2005 | Doddroe et al. |
| 6,875,241 B2 | 4/2005 | Christensen |
| 6,876,135 B2 | 4/2005 | Pelrine et al. |
| 6,908,488 B2 | 6/2005 | Paasivaara |
| 6,910,331 B2 | 6/2005 | Asai et al. |
| 6,918,308 B2 | 7/2005 | Biedermann |
| 6,955,692 B2 | 10/2005 | Grundei |
| 6,966,882 B2 | 11/2005 | Horst |
| 6,966,933 B2 | 11/2005 | Christensen |
| 7,025,792 B2 | 4/2006 | Collier |
| 7,029,500 B2 | 4/2006 | Martin |
| 7,042,197 B2 | 5/2006 | Turner et al. |
| 7,063,727 B2 | 6/2006 | Phillips et al. |
| 7,066,964 B2 | 6/2006 | Wild |
| 7,066,896 B1 | 7/2006 | Kiselik |
| 7,101,487 B2 | 9/2006 | Hsu et al. |
| 7,112,938 B2 | 9/2006 | Takenaka et al. |
| 7,118,601 B2 | 10/2006 | Yasui |
| 7,131,998 B2 | 11/2006 | Pasolini |
| 7,137,998 B2 | 11/2006 | Bedard et al. |
| 7,147,667 B2 | 12/2006 | Bedard |
| 7,150,762 B2 | 12/2006 | Caspers |
| 7,164,967 B2 | 1/2007 | Etienne-Cummings et al. |
| 7,182,738 B2 | 2/2007 | Bonutti et al. |
| 7,198,071 B2 | 4/2007 | Bisbee, III et al. |
| 7,209,788 B2 | 4/2007 | Nicolelis et al. |
| 7,279,009 B2 | 10/2007 | Herr |
| 7,295,892 B2 | 11/2007 | Herr et al. |
| 7,300,240 B2 | 11/2007 | Brogardh |
| 7,308,333 B2 | 12/2007 | Kern et al. |
| 7,313,463 B2 | 12/2007 | Herr et al. |
| 7,314,490 B2 | 1/2008 | Bedard et al. |
| 7,381,192 B2 | 6/2008 | Brodard |
| 7,396,337 B2 | 7/2008 | McBean et al. |
| 7,410,338 B2 | 8/2008 | Schiele et al. |
| 7,410,471 B1 | 8/2008 | Campbell et al. |
| 7,410,472 B2 | 8/2008 | Yakimovich et al. |
| 7,431,737 B2 | 10/2008 | Ragnarsdottir et al. |
| 7,455,696 B2 | 11/2008 | Bisbee, III et al. |
| 7,462,201 B2 | 12/2008 | Christensen |
| 7,485,152 B2 | 2/2009 | Haynes et al. |
| 7,503,900 B2 | 3/2009 | Goswami |
| 7,520,904 B2 | 4/2009 | Christensen |
| 7,531,006 B2 | 5/2009 | Clausen et al. |
| 7,552,664 B2 | 6/2009 | Bulatowicz |
| 7,575,602 B2 | 8/2009 | Amirouche et al. |
| 7,578,799 B2 | 8/2009 | Thorsteinsson et al. |
| 7,588,604 B2 | 9/2009 | Okuda |
| 7,637,957 B2 | 12/2009 | Ragnarsdottir et al. |
| 7,637,959 B2 | 12/2009 | Clausen et al. |
| 7,641,700 B2 | 1/2010 | Yasui |
| 7,655,050 B2 | 2/2010 | Palmer et al. |
| 7,691,154 B2 | 4/2010 | Asgeirsson et al. |
| 7,736,394 B2 | 6/2010 | Bedard et al. |
| 7,794,505 B2 | 9/2010 | Clausen et al. |
| 7,799,091 B2 | 9/2010 | Herr et al. |
| 7,811,333 B2 | 10/2010 | Johnsson et al. |
| 7,811,334 B2 | 10/2010 | Ragnarsdottir et al. |
| 7,815,689 B2 | 10/2010 | Bedard et al. |
| 7,862,620 B2 | 1/2011 | Clausen et al. |
| 7,867,284 B2 | 1/2011 | Bedard |
| 7,867,285 B2 | 1/2011 | Clausen et al. |
| 7,883,546 B2 | 2/2011 | Kazerooni et al. |
| 7,896,927 B2 | 3/2011 | Clausen et al. |
| 7,918,808 B2 | 4/2011 | Simmons |
| 7,942,935 B2 | 5/2011 | Iversen et al. |
| 7,955,398 B2 | 6/2011 | Bedard et al. |
| 7,985,265 B2 | 7/2011 | Moser et al. |
| 7,992,849 B2 | 8/2011 | Sugar et al. |
| 8,007,544 B2 | 8/2011 | Jonsson et al. |
| 8,011,229 B2 | 9/2011 | Lieberman et al. |
| 8,048,007 B2 | 11/2011 | Roy |
| 8,048,172 B2 | 11/2011 | Jonsson et al. |
| 8,057,550 B2 | 11/2011 | Clausen |
| 8,075,633 B2 | 12/2011 | Herr et al. |
| 8,083,807 B2 | 12/2011 | Auberger et al. |
| 8,087,498 B2 | 1/2012 | Dupuis et al. |
| 8,109,890 B2 | 2/2012 | Aminian et al. |
| 8,122,772 B2 | 2/2012 | Clausen et al. |
| 8,142,370 B2 | 3/2012 | Weinberg et al. |
| 8,211,042 B2 | 7/2012 | Gilbert et al. |
| 8,231,687 B2 | 7/2012 | Bedard et al. |
| 8,287,477 B1 | 10/2012 | Herr et al. |
| 8,323,354 B2 | 12/2012 | Bedard et al. |
| 8,366,788 B2 | 2/2013 | Moser et al. |
| 8,403,997 B2 | 3/2013 | Sykes et al. |
| 8,419,804 B2 | 4/2013 | Herr et al. |
| 8,435,309 B2 | 5/2013 | Gilbert et al. |
| 8,500,823 B2 | 8/2013 | Herr et al. |
| 8,512,415 B2 | 8/2013 | Herr et al. |
| 8,551,184 B1 | 10/2013 | Herr |
| 8,601,897 B2 | 12/2013 | Lauzier et al. |
| 8,617,254 B2 | 12/2013 | Bisbee, III et al. |
| 8,652,218 B2 | 2/2014 | Goldfarb et al. |
| 8,657,886 B2 | 2/2014 | Clausen et al. |
| 8,702,811 B2 | 4/2014 | Ragnarsdottir et al. |
| 8,790,282 B2 | 7/2014 | Jung et al. |
| 8,801,802 B2 | 8/2014 | Oddsson et al. |
| 8,814,949 B2 | 8/2014 | Gramnaes |
| 8,852,292 B2 | 10/2014 | Ragnarsdottir et al. |
| 8,864,846 B2 | 10/2014 | Herr et al. |
| 8,869,626 B2 | 10/2014 | Clausen et al. |
| 8,870,967 B2 | 10/2014 | Herr et al. |
| 8,986,397 B2 | 3/2015 | Bédard et al. |
| 9,032,635 B2 | 5/2015 | Herr et al. |
| 9,044,346 B2 | 6/2015 | Langlois et al. |
| 9,060,883 B2 | 6/2015 | Herr et al. |
| 9,060,884 B2 | 6/2015 | Langlois |
| 9,066,819 B2 | 6/2015 | Gramnaes |
| 9,078,774 B2 | 7/2015 | Jónsson et al. |
| 9,114,029 B2 | 8/2015 | Ásgeirsson |
| 9,221,177 B2 | 12/2015 | Herr et al. |
| 9,271,851 B2 | 3/2016 | Claussen et al. |
| 9,289,316 B2 | 3/2016 | Ward et al. |
| 9,345,591 B2 | 5/2016 | Bisbee, III et al. |
| 9,345,592 B2 | 5/2016 | Herr et al. |
| 9,351,856 B2 | 5/2016 | Herr et al. |
| 9,358,137 B2 | 6/2016 | Bédard et al. |
| 9,459,698 B2 | 10/2016 | Lee |
| 9,462,966 B2 | 10/2016 | Clausen et al. |
| 9,498,401 B2 | 11/2016 | Herr et al. |
| 9,526,635 B2 | 12/2016 | Gilbert et al. |
| 9,526,636 B2 | 12/2016 | Bédard et al. |
| 9,532,877 B2 | 1/2017 | Holgate |
| 9,554,922 B2 | 1/2017 | Casler et al. |
| 9,561,118 B2 | 2/2017 | Clausen et al. |
| 9,604,368 B2 | 3/2017 | Holgate |
| 9,622,884 B2 | 4/2017 | Holgate et al. |

(56) References Cited

U.S. PATENT DOCUMENTS

| | | |
|---|---|---|
| 9,649,206 B2 | 5/2017 | Bédard |
| 9,682,005 B2 | 6/2017 | Herr et al. |
| 9,687,377 B2 | 6/2017 | Han et al. |
| 9,707,104 B2 | 7/2017 | Clausen |
| 9,717,606 B2 | 8/2017 | Gramnaes |
| 9,737,419 B2 | 8/2017 | Herr et al. |
| 9,808,357 B2 | 11/2017 | Langlois |
| 9,839,552 B2 | 12/2017 | Han et al. |
| 9,895,240 B2 | 2/2018 | Langlois et al. |
| 2001/0002772 A1 | 6/2001 | Kim et al. |
| 2002/0007690 A1 | 1/2002 | Song et al. |
| 2002/0079857 A1 | 6/2002 | Ishii et al. |
| 2002/0087216 A1 | 7/2002 | Atkinson et al. |
| 2002/0103541 A1 | 8/2002 | Meyers et al. |
| 2002/0138153 A1* | 9/2002 | Koniuk ................ 623/24 |
| 2003/0005786 A1 | 1/2003 | Stuart et al. |
| 2003/0019700 A1 | 1/2003 | Wittig |
| 2004/0019382 A1* | 1/2004 | Amirouche et al. ....... 623/18.11 |
| 2004/0049290 A1* | 3/2004 | Bedard ............ A61F 2/644 623/24 |
| 2004/0064195 A1 | 4/2004 | Herr |
| 2004/0078299 A1 | 4/2004 | Down-Logan et al. |
| 2004/0083007 A1 | 4/2004 | Molino et al. |
| 2004/0153484 A1 | 8/2004 | Unno |
| 2004/0217324 A1 | 11/2004 | Hsu et al. |
| 2005/0049719 A1 | 3/2005 | Wilson |
| 2005/0049721 A1 | 3/2005 | Sulprizio |
| 2005/0070834 A1 | 3/2005 | Herr et al. |
| 2005/0071017 A1 | 3/2005 | Lecomte et al. |
| 2005/0107889 A1* | 5/2005 | Bedard ............ A61F 2/66 623/24 |
| 2005/0113973 A1 | 5/2005 | Endo et al. |
| 2005/0137717 A1 | 6/2005 | Gramnas |
| 2005/0166685 A1 | 8/2005 | Boiten |
| 2005/0216097 A1 | 9/2005 | Rifkin |
| 2005/0283257 A1 | 12/2005 | Bisbee et al. |
| 2006/0025959 A1 | 2/2006 | Gomez et al. |
| 2006/0069336 A1 | 3/2006 | Krebs et al. |
| 2006/0069448 A1* | 3/2006 | Yasui ............... A61F 2/60 623/24 |
| 2006/0136072 A1 | 6/2006 | Bisbee et al. |
| 2006/0184252 A1 | 8/2006 | Oddsson et al. |
| 2006/0184280 A1 | 8/2006 | Oddsson et al. |
| 2006/0189899 A1 | 8/2006 | Flaherty et al. |
| 2006/0249315 A1 | 11/2006 | Herr et al. |
| 2006/0259153 A1 | 11/2006 | Harn et al. |
| 2006/0260620 A1 | 11/2006 | Kazerooni et al. |
| 2007/0027557 A1 | 2/2007 | Jonsson et al. |
| 2007/0043449 A1 | 2/2007 | Herr et al. |
| 2007/0050047 A1 | 3/2007 | Ragnarsdottir et al. |
| 2007/0061016 A1 | 3/2007 | Kuo et al. |
| 2007/0123997 A1 | 5/2007 | Herr et al. |
| 2007/0129653 A1 | 6/2007 | Sugar et al. |
| 2007/0162152 A1 | 7/2007 | Herr et al. |
| 2008/0004718 A1 | 1/2008 | Mosler |
| 2008/0046096 A1 | 2/2008 | Bedard et al. |
| 2008/0058668 A1 | 3/2008 | Seyed Momen et al. |
| 2008/0141813 A1 | 6/2008 | Ehrat |
| 2008/0262635 A1 | 10/2008 | Moser et al. |
| 2008/0306612 A1 | 12/2008 | Mosler |
| 2009/0030344 A1 | 1/2009 | Moser et al. |
| 2009/0030530 A1 | 1/2009 | Martin |
| 2009/0088912 A1 | 4/2009 | Rajaraman |
| 2009/0192625 A1 | 7/2009 | Boiten |
| 2009/0204229 A1 | 8/2009 | Mosler et al. |
| 2009/0204230 A1 | 8/2009 | Kaltenborn et al. |
| 2009/0265018 A1 | 10/2009 | Goldfarb et al. |
| 2009/0299480 A1 | 12/2009 | Gilbert et al. |
| 2009/0299489 A1 | 12/2009 | Gramnas |
| 2010/0023133 A1 | 1/2010 | Fairbanks et al. |
| 2010/0030343 A1 | 2/2010 | Hansen et al. |
| 2010/0042228 A1 | 2/2010 | Doddroe et al. |
| 2010/0094431 A1 | 4/2010 | Albrecht-Laatsch |
| 2010/0113980 A1 | 5/2010 | Herr et al. |
| 2010/0114329 A1 | 5/2010 | Casler et al. |
| 2010/0131101 A1 | 5/2010 | Engeberg et al. |
| 2010/0161077 A1 | 6/2010 | Boone et al. |
| 2010/0174384 A1 | 7/2010 | Herr et al. |
| 2010/0179668 A1 | 7/2010 | Herr et al. |
| 2010/0185124 A1 | 7/2010 | Bisbee, III et al. |
| 2010/0185301 A1 | 7/2010 | Hansen et al. |
| 2010/0241242 A1 | 9/2010 | Herr et al. |
| 2010/0262260 A1 | 10/2010 | Bedard et al. |
| 2010/0275718 A1 | 11/2010 | Stuart et al. |
| 2010/0305716 A1 | 12/2010 | Pusch et al. |
| 2010/0324456 A1 | 12/2010 | Jonsson et al. |
| 2010/0324699 A1 | 12/2010 | Herr et al. |
| 2011/0015761 A1 | 1/2011 | Celebi et al. |
| 2011/0082566 A1 | 4/2011 | Herr et al. |
| 2011/0106274 A1 | 5/2011 | Ragnarsdottir et al. |
| 2011/0125290 A1 | 5/2011 | Langlois |
| 2011/0130847 A1 | 6/2011 | Bedard et al. |
| 2011/0132131 A1 | 6/2011 | Worz |
| 2011/0137429 A1 | 6/2011 | Bedard |
| 2011/0166674 A1 | 7/2011 | Montmartin |
| 2011/0196509 A1 | 8/2011 | Jansent et al. |
| 2011/0202144 A1 | 8/2011 | Palmer et al. |
| 2011/0208322 A1 | 8/2011 | Rifkin et al. |
| 2011/0224804 A1 | 9/2011 | Clausen et al. |
| 2011/0245931 A1 | 10/2011 | Clausen et al. |
| 2011/0295384 A1 | 12/2011 | Herr et al. |
| 2011/0295385 A1 | 12/2011 | Herr et al. |
| 2012/0016492 A1 | 1/2012 | Clausen |
| 2012/0078415 A1 | 3/2012 | Kubo et al. |
| 2012/0130508 A1 | 5/2012 | Harris et al. |
| 2012/0191221 A1 | 6/2012 | Bedard et al. |
| 2012/0203359 A1 | 8/2012 | Schimmels et al. |
| 2012/0209405 A1 | 8/2012 | Herr et al. |
| 2012/0226364 A1 | 9/2012 | Kampas et al. |
| 2012/0232672 A1 | 9/2012 | Ragnarsdottir et al. |
| 2012/0259430 A1 | 10/2012 | Han et al. |
| 2012/0283845 A1 | 11/2012 | Herr et al. |
| 2012/0330439 A1 | 12/2012 | Goldfarb et al. |
| 2013/0035769 A1 | 2/2013 | Bedard et al. |
| 2013/0118287 A1 | 5/2013 | Holgate |
| 2013/0142608 A1 | 6/2013 | Zhang et al. |
| 2013/0144402 A1 | 6/2013 | Clausen et al. |
| 2013/0173022 A1 | 7/2013 | Arabian et al. |
| 2013/0204395 A1 | 8/2013 | Gramnaes |
| 2013/0218295 A1 | 8/2013 | Holgate et al. |
| 2013/0218298 A1 | 8/2013 | Mosler |
| 2013/0268093 A1 | 10/2013 | Gilbert et al. |
| 2013/0282141 A1 | 10/2013 | Herr et al. |
| 2013/0297041 A1 | 11/2013 | Bedard et al. |
| 2014/0039642 A1 | 2/2014 | Nijiman et al. |
| 2014/0074243 A1 | 3/2014 | Holgate |
| 2014/0081424 A1 | 3/2014 | Herr et al. |
| 2014/0114437 A1 | 4/2014 | Herr et al. |
| 2014/0121782 A1 | 5/2014 | Herr et al. |
| 2014/0200680 A1 | 7/2014 | Holgate et al. |
| 2014/0243997 A1 | 8/2014 | Clausen et al. |
| 2014/0277586 A1 | 9/2014 | Clausen |
| 2014/0330393 A1 | 11/2014 | Ward et al. |
| 2015/0032225 A1 | 1/2015 | Oddsson et al. |
| 2015/0073566 A1 | 3/2015 | Ragnarsdottir et al. |
| 2015/0127118 A1 | 5/2015 | Herr et al. |
| 2015/0164661 A1 | 6/2015 | Ragnarsdottir et al. |
| 2015/0209214 A1 | 7/2015 | Herr et al. |
| 2015/0223952 A1 | 8/2015 | Langlois et al. |
| 2015/0265429 A1 | 9/2015 | Jónsson et al. |
| 2015/0297368 A1 | 10/2015 | Langlois |
| 2015/0320573 A1 | 11/2015 | Gramnaes |
| 2015/0328020 A1 | 11/2015 | Clausen et al. |
| 2016/0302956 A1 | 10/2016 | Gilbert et al. |
| 2017/0112640 A1 | 4/2017 | Clausen et al. |
| 2017/0241497 A1 | 8/2017 | Mooney et al. |
| 2017/0304083 A1 | 10/2017 | Clausen |
| 2018/0125678 A1 | 5/2018 | Langlois |
| 2018/0177618 A1 | 6/2018 | Langlois |

FOREIGN PATENT DOCUMENTS

| | | |
|---|---|---|
| CN | 2043873 U | 9/1989 |
| CN | 1215614 | 5/1999 |

(56) References Cited

FOREIGN PATENT DOCUMENTS

| | | |
|---|---|---|
| CN | 2400072 Y | 10/2000 |
| CN | 2776340 | 5/2006 |
| DE | 3543291 | 6/1987 |
| DE | 3923056 | 1/1991 |
| DE | 3923057 | 1/1991 |
| DE | 43 05 213 | 8/1993 |
| DE | 4229330 | 3/1994 |
| EP | 0358056 | 3/1990 |
| EP | 0 380 060 | 8/1990 |
| EP | 0654254 | 5/1995 |
| EP | 0902547 | 3/1999 |
| EP | 1125825 | 1/2001 |
| EP | 1107420 | 6/2001 |
| EP | 1166726 | 1/2002 |
| EP | 1169982 | 1/2002 |
| EP | 1 410 780 | 4/2004 |
| EP | 1 442 704 | 8/2004 |
| EP | 1 547 567 | 6/2005 |
| EP | 1 792 597 | 6/2007 |
| EP | 2 564 817 | 3/2013 |
| EP | 2 702 963 | 3/2014 |
| FR | 2293185 | 7/1976 |
| FR | 2623086 A1 | 5/1989 |
| FR | 2 816 463 | 5/2002 |
| GB | 2201260 | 8/1988 |
| GB | 2 228 201 | 8/1990 |
| GB | 2244006 | 11/1991 |
| GB | 2260495 | 4/1993 |
| GB | 2301776 | 12/1996 |
| GB | 2302949 | 2/1997 |
| GB | 2338653 | 12/1999 |
| GB | 2343848 | 5/2000 |
| GB | 2367753 | 4/2002 |
| JP | 59-32453 | 2/1984 |
| JP | 59-032453 | 2/1984 |
| JP | 59-71747 | 4/1984 |
| JP | 59-071747 | 4/1984 |
| JP | 59-088147 | 5/1984 |
| JP | 60-081530 | 5/1985 |
| JP | 60-177102 | 9/1985 |
| JP | 59-189843 | 10/1985 |
| JP | 01-244748 | 9/1989 |
| JP | 03-181633 | 8/1991 |
| JP | 04-78337 | 3/1992 |
| JP | 05-123348 | 5/1993 |
| JP | 5-161668 | 6/1993 |
| JP | 7-24766 | 1/1995 |
| JP | 11-000345 | 1/1999 |
| JP | 11-056885 | 3/1999 |
| JP | 11-215793 | 8/1999 |
| JP | 2001-277175 | 10/2001 |
| JP | 2002-191654 | 7/2002 |
| JP | 2005-500 | 1/2005 |
| JP | 2005-536317 | 12/2005 |
| JP | 2009-153660 | 7/2009 |
| KR | 2002/0041137 | 6/2002 |
| SU | 1447366 | 12/1988 |
| SU | 1731210 | 5/1992 |
| WO | WO 94/06374 | 3/1994 |
| WO | WO 94/09727 | 5/1994 |
| WO | WO 95/26171 | 10/1995 |
| WO | WO 96/39110 | 12/1996 |
| WO | WO 96/41599 | 12/1996 |
| WO | WO 97/00661 | 1/1997 |
| WO | WO 97/27822 | 8/1997 |
| WO | WO 98/38951 | 9/1998 |
| WO | WO 99/00075 | 1/1999 |
| WO | WO 99/05991 | 2/1999 |
| WO | WO 99/011206 | 3/1999 |
| WO | WO 99/044547 | 9/1999 |
| WO | WO 99/55261 | 11/1999 |
| WO | WO 00/27318 | 5/2000 |
| WO | WO 01/17466 | 3/2001 |
| WO | WO 02/80825 | 10/2002 |
| WO | WO 03/003953 | 1/2003 |
| WO | WO 03/088373 | 10/2003 |
| WO | WO 2004/017890 | 3/2004 |
| WO | WO 2004/092606 | 10/2004 |
| WO | WO 2005/048887 | 6/2005 |
| WO | WO 2006/076164 | 7/2006 |
| WO | WO 2007/025116 | 3/2007 |
| WO | WO 2007/095933 | 8/2007 |
| WO | WO 2008/080231 | 7/2008 |
| WO | WO 2008/080232 | 7/2008 |
| WO | WO 2008/080233 | 7/2008 |
| WO | WO 2008/080234 | 7/2008 |
| WO | WO 2011/005482 | 1/2011 |
| WO | WO 2011/096965 | 8/2011 |
| WO | WO 2010/027968 | 3/2012 |
| WO | WO 2012/062279 | 5/2012 |
| WO | WO 2012/091555 | 7/2012 |
| WO | WO 2013/006585 | 1/2013 |
| WO | WO 2014/133975 | 9/2014 |
| WO | WO 2014/159114 | 10/2014 |
| WO | WO 2015/157723 | 10/2015 |

OTHER PUBLICATIONS

Advanced Materials & Processes, Sep. 2003, vol. 9, Issue 161, pp. 29-30, 3 pages.

Kamiar Aminian et al., *Estimation of Speed and Incline of Walking Using Neural Network*, IEEE Transactions on Instrumentation and Measurement, vol. 44, No. 3, Jun. 1995, at 743.

Andrews, BIJ., et al., Hybrid FES Orthosis Incorporating Closed Loop Control and Sensory Feedback, *J. Biomed. Eng.* 1988, vol. 10, Apr. 189-195.

Assembly and Adjustment Instructions for 1P50-R, pp. 1-21, PROTEOR, Sep. 2004.

Au S K et al., "An EMG-Position Controlled System for an Active Ankle-Foot Prosthesis: An Initial Experimental Study" Rehabilitation Robotics, 2005. ICORR 2005., 9th International Conference in Chicago, IL, USA Jun. 28-Jul. 1, 2005, Piscataway, NJ, IEEE, Jun. 28, 2005, pp. 375-379, XP008078417.

Bachmann, et al., Inertial and Magnetic Tracking of Limb Segment Orientation for Inserting Humans into Synthetic Environments, 2000.

Bar, A et al., "Adaptive Microcomputer Control of an Artificial Knee in Level Walking," J. Biomechanical Eng., vol. 5, pp. 145-150, 1983.

Baten, Inertial Sensing in Ambulatory Back Load Estimation, 1996.

Benedetti, Gait Analysis of Patients Affected by Post-Traumatic Ankle Arthrosis Treated with Osteochondral Allograft Transplantation, SIAMOC 2006 Congress Abstracts/Gait & Posture.

Blaya, Force-Controllable Ankle Foot Orthosis (AFO) to Assist Drop Foot Gait, Feb. 2003 (believed to be catalogued on or after Jul. 8, 2003.

Blaya, J.A., et al., "Adaptive Control of a Variable-Impedance Ankle-Foot Orthosis to Assist Drop-Foot Gait" IEEE Transactions on Neural Systems and Rehabilitation Engineering, vol. 12, No. 1, Mar. 2004, pp. 24-31.

Blumentritt, Siegmar, Ph.D., et al.; "Design Principles, Biomedical Data and Clinical Experience with a Polycentric Knee Offering Controlled Stance Phase Knee Flexion: A Preliminary Report", 1997, Journal of Prothetics and Orthotics, vol. 9, No. 1, 18-24.

Bogert, et al., A Method for Inverse Dynamic Analysis Using Accelerometry, 1995.

Bortz, A New Mathematical Formulation for Strapdown Inertial Navigation, 1971.

Bouten, A Triaxial Accelerometer and Portable Data Processing Unit for the Assessment of Daily Physical Activity, 1997.

Bouten, Carlifin V., et al., Assessment of Energy Expenditure for Physical Activity Using a Triaxial Accelerometer. *Med. Sci. Sports Exerc.*, vol. 26, No. 12, pp. 151-1523, 1994.

Carlson et al., "Smart Prosthetics Based on Magnetorheological Fluids", 8th Annual Symposium on Smart Structures and Materials, Mar. 2001.

Carlson, J. David, What makes a Good MR Fluid?, 8th International Conference on Electrorheological (ER) Fluids and magnetorheological (MR) Suspensions, Nice 7 pages, Jul. 9-13, 2001.

(56) References Cited

OTHER PUBLICATIONS

Copes/Bionic Ankle, The Most Significant Development in Ankle Prosthetics in Over a Half Century, 1985.
Crago, et al., New Control Strategies for Neuroprosthetic Systems, 1996.
Dai R, et al., Application of Tilt Sensors in Functional Electrical Stimulation. IEEE Trans. Rehab. Eng. 1996; 4(2):63-71.
Dietl, H. Bargehr, Der Einsatz von Elektronik bei Prothesen zur Versorgung der unteren Extremitat, Med. Orth. Tech. 117 1997, pp. 31-35.
Elliott, Scott B.; "MR Microprocessor-Controlled Swing and Stance," Presentation to American Academy of Orthotists & Prosthetists (Feb. 4, 2004), 81 pages.
Ferris, D. P., et al., An Ankle-Foot Orthosis Powered by Artificial Pneumatic Muscles, Journal of Applied Biomechanics, May 21, 2005, pp. 189-197.
Fisekovic, et al., New Controller for Functional Electrical Stimulation Systems, 2000.
Fite, Kevin et al., "Design and Control of an Electrically Powered Knee Prosthesis", 2007 IEEE 10th International Conference on Rehabilitation Robotics, Jun. 12, 2007, pp. 902-905, Noordwijk, The Netherlands.
Flowers, et al., "An Electrohydraulic Knee-Torque Controller . . . "; Journal of Biomechanical Engineering: Transactions of the ASME; Feb. 1977, pp. 3-8.
Foerster, et al. Detection of Posture and Motion by Accelerometry—A Validation Study in Ambulatory Monitoring, 1999.
Foxlin, et al., Miniature 6-DOF Inertial System for Tracking HMDs, 1998.
Frank, K., Reliable Real-Time Recognition of Motion Related Human Activities Using MEMS Inertial Sensors.
Fujita, K. et al., Joint Angle Control with Command Filter for Human Ankle Movement Using Functional Electrical Stimulation, Proceedings of the 9th Annual Conference of the IEEE Engineering in Medicine and Biology Society, Nov. 13-16, 1987.
Gelat, Thierry et al., Adaptation of the gait initiation process for stepping on to a new level using a single step. Exp Brain Res(2000) 133-538-546, Jun. 21, 2000, pp. 9.
Godha, S. et al., Integrated GPS/INS System for Pedestrian Navigation in a Signal Degraded Environment. ION GNSS 2006, Fort Worth TX, Sep. 26-29, 2006, p. 1-14.
Graps, A., An Introduction to Wavelets, IEEE Computational Science & Engineering, 1995.
Grimes, Donald L., An Active Multi-Mode Above-Knee Prosthesis Controller, Massachusetts Institute of Technology 1979, 158 pages, 1979.
Gronqvist, Raoul et al., Human-centered approaches in slipperiness measurement, Ergonomics, Oct. 20, 2001, vol. 44, Issue 13, pp. 1167-1199 (32 pages).
Hanafusa et al., "A Robot Hand with Elastic Fingers and Its Application to Assembly Process," pp. 337-359, Robot Motion, Brady et al., MIT Press, Cambridge, MA, 1982.
Hanson, James P. et al., Predicting slips and falls considering required and available friction, Ergonomics, 1999, vol. 42, Issue 12, pp. 1619-1633 (15 pages).
Hashimoto et al., "An instrumented compliant wrist using a parallel mechanism," Japan/USA Symposium on Flexible Automation, vol. 1, pp. 741-744, ASME, 1992.
Hayes, W.C., et al., Leg Motion Analysis During Gait by Multiaxial Accelerometry: Theoretical Foundations and Preliminary Validations *Journal of Biomechanical Engineering*, vol. 105, Aug. 1983, p. 283-289.
Herr, et al., "User-adaptive control of a magnetorheological prosthetic knee", Industrial Robot: an International Journal, vol. 30, No. 1, (2003) pp. 42-55.
Herr, et al., Patient-Adaptive Prosthetic and Orthotic Leg Systems, 12th Nordic Baltic Conference on Biomedical Engineering and Medical Physics, Proceedings of the International Federation for Medical & Biological Engineering, 2002.
Herr, Hugh, Presentation at "Experiencing the Frontiers of Biomedical Technology," (Mar. 10-11, 2003).
Heyn, Andreas, et al., The Kinematics of the Swing Phase Obtained From Accelerometer and Gyroscope Measurements, *18th Annual International Conference of the IEEE Engineering in Medicine and Biology Society*, Amsterdam 1996, p. 463-464.
Hill, Stephen W. et al., Altered kinetic strategy for the control of swing limb elevation over obstacles in unilateral below-knee amputee gait, Journal of Biomechanics, 1999, vol. 32, pp. 545-549 (5 pages).
Howard, "Joint and Actuator Design for Enhanced Stability in Robotic Force Control," Ph.D. thesis, Massachusetts Inst. of Technology, Dept. of Aeronautics and Astronautics, 1990.
International Search Report and Written Opinion for International Application No. PCT/US2009/037982, dated Jul. 29, 2009.
Jones, S. F. et al., The gait initiation process in unilateral lower-limb amputees when stepping up and stepping down to a new level, Clinical Biomechanics, 2005, vol. 20, pp. 405-413 (9 pages).
Jonic, et al., Three Machine Learning Techniques for Automatic Determination of Rules to Control Locomotion, 1999.
Kidder, Steven M., et al., A System for the Analysis of Foot and Ankle Kinematics During Gait. *EEE Transactions on Rehabilitation Engineering*, vol. 4, No. 1, Mar. 1996.
Kirkwood, et al., Automatic Detection of Gait Events: A Case Study Using Inductive Learning Techniques, 1989.
Kirsner, Scott, "A Step in the Right Direction Biomedical Horizons Expanding," Boston Globe (Mar. 17, 2003).
Kooij, et al., A Multisensory Integration Model of Human Stance Control, 1998.
Kostov, et al., Machine Learning in Control of Functional Electrical Stimulation Systems for Locomotion, 1995.
Kuster, M. et al., Kinematic and kinetic comparison of downhill and level walking, Clinical Biomechanics, 1995, vol. 10, Issue 2, pp. 79-84 (6 pages).
LaFortune, Mario A., Three Dimensional Acceleration of the Tibia During Walking and Running. *J. Biomechanics* vol. 24, No. 10, pp. 877-886, 1991.
Lee, S., Activity and Location Recognition Using Wearable Sensors, Pervasive Computing, IEEE, 2002.
Lelas, et al., Hydraulic versus Magnetorheological-based Electronic Knee Protheses: A Clinical Comparison, Harvard Medical School, Dept. of Phys. Med. And Rehab., Boston, MA pp. 1-16.
Light, L.H. et al., Skeletal Transients on Heel Strike in Normal Walking with Different Footwear, . Biomechanics, vol. 13, 1980, pp. 477-480.
Luinge, H.J., Inertial Sensing of Movement. Doctoral Thesis, Twente University Press, Enschede, Netherlands (2002) p. 9-13.
Martens, W., *Exploring Information Content and Some Application of Body Mounted Piezo-Resistive Accelerometers*, Phy Vision b.v., Gemert, The Netherlands.
Mayagoitia, Ruth E., et al., Accelerometer and Rate Gyroscope Measurement of Kinematics: An Inexpensive Alternative to Optical Motion Analysis Systems. *Journal of Biomechanics* 35 (2002) 537-542.
Michel, V. et al., The strategies to regulate and to modulate the propulsive forces during gait initiation in lower limb amputees, Exp Brain Res, May 27, 2004, vol. 158, pp. 356-365 (10 pages).
Moe-Nilssen, A New Method for Evaluating Motor Control in Gait Under Real-Life Environmental Conditions, Parts 1—The instrument; Part 2: Gait Analysis, 1997.
Morris, J.R. W., Accelerometry—A Technique for the Measurement of Human Body Movements, *J. Biomechanis*, 1973, vol. 6, pp. 729-736.
Moseley, Anne M. et al., High—and low-ankle flexibility and motor task performance, Gait and Posture, 2003, vol. 18, pp. 73-80 (8 pages).
"MT9 Inertial 3D Motion Tracker," Xsens Technologies B.Y., available at http://www.xsens.com/download/MT9_brochure.pdf (at least as early as Oct. 2004), printed Jul. 20, 2006, 2 pages.
Nadeau, S. et al., Frontal and sagittal plane analyses of the stair climbing task in healthy adults aged over 40 years: what are the challenges compared to level walking?, Clinical Biomechanics, 2003, vol. 18, pp. 950-959 (10 pages).

(56) References Cited

OTHER PUBLICATIONS

A. Nakagawa, Intelligent Knee Mechanism and the Possibility to Apply the Principle to the Other Joints, Engineering in Medicine and Biology Society, Proceedings of the 20th Annual International Conference of the IEEE, vol. 20, No. 5, Dec. 1998, at 2282.
OSSUR Academy, 2004 Course Descriptions, OSSUR North America, 16 pages.
Otto Bock Orthopadische Industrie GMBH & Co., C-Leg Fitting Statistics (Abstract), Mar. 2000, 4 pages.
Otto Bock Orthopadische Industrie, C-LEG A new dimension in amputee mobility, Otto Bock Data Sheet 1997.
Otto Bock Orthopadische Industrie, The Electronic C-Leg compact Leg Prosthesis System, Instructions for Use; 2002.
Otto Bock Orthopadische Industrie, The Electronic C-Leg Knee Joint System, Instructions for Use; 2002. available at http://www.ottobockus.com/products/lower_limb_prosthetics/c-leg_instructions.pdg, 32 pages (printed Jul. 20, 2006).
Otto Bock, Quality for Life, Software C-Soft, Menu-driven setting of the C-Leg, 2004 1 page.
Otto Bock's C-Leg, see http://web.archive.org/web/20040215152410/http:/www.ottobockus.com/products/lower_limb _prosthetics/c-leg.asp.
Otto, Judith, "Prosthetic Knees: What's Currently New and Impressive?", The O&P Edge, http://www.oandp.com/edge/issues/articles/2003-10_03.sp, Oct. 2003, 4 pages.
Otto, Judith, "Prosthetic Knees: What's on the Way?", The O&P edge, http://www.oandp.com/edge/issues/ articles/2003—10_02 .asp, Oct. 2003, 5 pages.
Petrofsky, Jerrold S., et. al., Feedback Control System for Walking in Man. *Comput. Biol. Med.* vol. 14, No. 2, pp. 135-149, 1984.
Pfeffer et al. , "Experiments with a Dual-Armed, Cooperative, Flexible-Drivetrain Robot System," Proc. 1993 IEEE Int. Conf. on Robotics & Automation, vol. 3, pp. 601-608, May 5, 1993.
Popovik, D. et al.; Optimal control for an Above-Knee Prosthesis With Two Degrees of Freedom, 1995, pp. 89-98, Jo. Biomechanics, vol. 28, No. 1.
Dejan Popovic et al., Control Aspects of Active Above-Knee Prosthesis, International Journal of Man-Machine Studies, vol. 35, Issue 6, Dec. 1991, at 751.
Powers, Christopher M. et al., Stair ambulation in persons with transtibial amputation: An analysis of the Seattle LightFootTM, Journal of Rehabilitation Research and Development, Jan. 1997, vol. 34, Issue 1, pp. 9-18 (10 pages).
Proteor, Assembly and Adjustrnent Instructions for IP50-R, pp. 1-21, Sep. 2004.
Raggi, M., et al. Wearable Sensors for the Real-Time Assessment of Gait Temporal Symmetry in Above-Knee Amputees: The 'SEAG' Protocol, Abstracts of the 2007 SIAMOC Congress.
Raggi, M., et al., Gait Analysis Through Inertial Sensors in Transfemoral Amputees: Step and Stride Regularity, SIAMOC 2006 Congress Abstracts/Gait & Posture.
Rao, Sreesha S. et al., Segment Velocities in Normal and Transtibial Amputees: Prosthetic Design Implications, IEEE Transactions on Rehabilitation Engineering, Jun. 1998, vol. 6, Issue 2, pp. 219-226 (8 pages).
Redfern, Mark S. et al., Biomechanics of descending ramps, Gait and Posture, 1997, vol. 6, pp. 119-125 (7 pages).
Reiner, Robert et al., Stair ascent and descent at different inclinations, Gait and Posture, 2002, vol. 15, pp. 32-44 (13 pages).
Reitman, J. S., et al., Gait Analysis in Prosthetics: Opinions, Ideas, and Conclusions, Prosthetics and Orthotics International, 2002, 26, 50-57.
Robinson, David W. et al., *Series Elastic Actuator Development for a Biomimetic Walking Robot*, MIT Leg Laboratory, 1999.
Robinson, David William, *Design and Analysis of Series Elasticity in Closed-Loop Actuator Force Control*, MIT Department of Mechanical Engineering, Jun. 1996.
Schmalz T. et al., Energy Efficiency of Trans-Femoral Amputees Walking on Computer-Controlled Prosthetic Knee Joint "C-Leg" in 3 pages, Otto Bock et al. 1998.

Sekine, et al., Classification of Waist-Acceleration Signals in a Continuous Walking Record, 2000.
Sin S. W., et al., Significance of Non-Level Walking on Transtibial Prosthesis Fitting with Particular Reference to the Effects of Anterior-Posterior Alignment, Journal of Rehabilitation Research and Development vol. 38 No. 1, Jan./Feb. 2001, p. 1-6.
Smidt, G.L., et al., An Automated Accelerometry System for Gait Analysis, *J. Biomechanics.* 1977, vol. 10, pp. 367-375.
State-of-the-Art Prosthetic Leg Incorporates Magneto-Rheological Technology, Medical Product Manufacturing News, p. 42, Nov. 2000.
Suga, T, et al., "Newly designed computer controlled knee-ankle-foot orthosis (Intellegent Orthosis)", Prostetics and Orthotics International, 1998, 22, 230-239.
Sugano et al., "Force Control of the Robot Finger Joint equipped with Mechanical Compliance Adjuster," Proc. 1992 IEEE/RSJ Int. Conf. on Intell. Robots & Sys., pp. 2005-2013, Jul. 1992.
Sup, Frank C. et al., "Design and Control of a Powered Knee and Ankle Prosthesis", 2007 IEEE International Conference on Robotics and Automation, Rome, Italy, Apr. 10, 2007, pp. 4134-4139.
Sup, Frank C. et al., "Design and Control of a Powered Transfemoral Prosthesis", The International Journal of Robotics Research, Feb. 2008, vol. 27, Issue 263.
Sup, Frank C. et al., "Design and Control of an Active Electrical Knee and Ankle Prosthesis", Proceedings of the 2nd Biennial IEEE/RASEMBS International Conference on biomedical Robotics and Biomechatronics, Oct. 19, 2008, pp. 523-528, Scottsdale, AZ.
Sup, Frank C. et al., "Design of a Pneumatically Actuated Transfemoral Prosthesis", Proceedings of IMECE2006: 2006 ASME International mechanical Engineering Congress and Exposition, Nov. 5, 2006, pp. 1-10, Chicago, Illinois.
Thakkar, Sneha, "Energy Economy Gait Analysis of an Autoadaptive Prosthetic Knee", Master's Thesis submitted to the Dept. of Electrical Engineering and Computer Science, MIT (2002) pp. 1-58.
R. Tomovic et al., *A Finite State Approach to the Synthesis of Bioengineering Control Systems*, IEEE Transactions on Human Factors in Electronics, vol. HFE-7, No. 2, Jun. 1966.
Tong, et al., Virtual Artificial Sensor Technique for Functional Electrical Stimulation, 1998.
Tong, Kaiyu and Malcolm H. Granat, *A Practical Gait Analysis System Using Gyroscopes*, Medical Engineering & Physics, vol. 21, No. 2, Mar. 1999, at 87-94.
Townsend MA et al., "Biomechanics and modeling of bipedal climbing and descending." Journal of Biomechanics 1976, vol. 9, No. 4, pp. 227-239, XP008078405.
U.S. Appl. No. 60/371,974 to Martin, filed Apr. 12, 2002.
Van der Loos, H.F.M., et al., "ProVAR Assistive Robot System Architecture", Proceedings of the 1999 IEEE International Conference on Robotics & Automation; Detroit, Michigan, May 1999, pp. 741-746.
Varol, Huseyin Atakan et al., "Decomposition-Based Control for a Powered Knee and Ankle Transfemoral Prosthesis", Proceedings of the 2007 IEEE IOth International Conference on Rehabilitation Robotics, Jun. 12, 2007, pp. 783-789, Noordwijk, The Netherlands.
Varol, Huseyin Atakan et al., "Real-time Intent Recognition for a Powered Knee and Ankle Transfemoral Prosthesis", Proceedings of the 2007 IEEE IOth International Conference on Rehabilitation Robotics, Jun. 12, 2007, pp. 16-23, Noordwijk, The Netherlands.
Varol, Huseyin Atakan, "Real-time Gait Mode Intent Recognition of a Powered Knee and Ankle Prosthesis for Standing and Walking", Proceedings of the 2nd Biennial IEEE/RAS-EMBS International Conference on Biomedical Robotics and Biomechatronics, Oct. 19, 2008, pp. 66-72, Scottsdale, AZ.
Peter H. Veltink et al. (1993), The Feasibility of Posture and Movement Detection by Accelerometry, in 15th Annual International Conference of the IEEE Engineering in Medicine and Biology Society, Oct. 28-31, 1993, San Diego, CA, 1230-1231.
Veltink, et al., Detection of Static and Dynamic Activities Using Uniaxial Accelerometers, 1996.
Wilkenfeld, Ari Ph.D.; An Auto-Adaptive External Knee Prosthesis, Artificial Intelligence Laboratory, MIT, Cambridge, Massachusetts, 3 pages, Sep. 2000.

(56) References Cited

OTHER PUBLICATIONS

Wilkenfeld, Ari Ph.D.; Biologically inspired autoadaptive control of a knee prosthesis, Dissertation Abstract, MIT, Cambridge, Massachusetts, 1 page, Sep. 2000.
Willemsen, A. TH. M., et al., Real-Time Gait Assessment Utilizing a New Way of Accelerometry. *J. Biomechanics* vol. 23, No. 8, pp. 859-863, 1990.
Willemsen, Antoon Th. M., et al., Automatic Stance-Swing Phase Detection from Accelerometer Data for Peroneal Nerve Stimulation. *IEEE Trasnactions on Biomedical Engineering*, vol. 37, No. 12, Dec. 1990, p. 1201-1208.
Williamson, Matthew M., *Series Elastic Actuators*, Massachusetts Institute of Technology Artificial Intelligence Laboratory, A.I. Technical Report No. 1524, Jan. 1995.
Woodward, M I, et al., Skeletal Accelerations Measured During Different Exercises. *Proceedings of the Institution of Mechanical Engineers*, Part H: Journal of Engineering Medicine 1993 207:79, DOI: 10.1243/PIME_PROC_1993_207_274_02.
Wu Ge, The Study of Kinematic Transients in Locomotion Using the Integrated Kinematic Sensor, IEEE Transactions on Rehabilitation Engineering, vol. 4, No. 3, Sep. 1996, p. 193-200.
Zamiska, Nicholas, Bionic Knee 'Learns' How to Walk, 1 page, The Wall Street Journal, Jul. 6, 2004.
Complaint for Patent Infringement filed Nov. 15, 2011, *Össur hf v. iWalk, Inc.* (involving U.S. Pat. No. 7,431,737 and 7,896,927), Case No. SACV11-01759 AN, 85 pages.
Defendant iWalk's Answer and Counterclaim to Plaintiff's Complaint for Patent Infringement filed Jan. 6, 2012, *Össur hf v. iWalk, Inc.* (involving U.S. Pat. Nos. 7,431,737 and 7,896,927), Case No. SACV-01759 AN, 95 pages.
Defendant iWalk's First Amended Answer and Counterclaim to Plaintiffs' Complaint for Patent Infringement filed Jan. 26, 2012, *Össur hf v. iWalk, Inc.* (involving U.S. Pat. Nos. 7,431,737 and 7,896,927), Case No. SACV-01759 AN, 20 pages.
Defendant iWalk's Amended Answer and Counterclaim filed Feb. 3, 2012, *Össur hf v. iWalk, Inc.* (involving U.S. Pat. Nos. 7,431,737 and 7,896,927), Case No. SACV-01759 JST, 94 pages.
Ossur's Reply to iWalk's Amended Counterclaims and Demand for Jury Trial filed Feb. 9, 2012, *Össur hf v. iWalk, Inc.* (involving U.S. Pat. Nos. 7,431,737 and 7,896,927), Case No. SACV11-01759 JST, 8 pages.
Memorandum of Points and Authorities in Support of Defendant iWalk's Motion to Transfer Venue, filed Apr. 2, 2012, *Össur hf v. iWalk, Inc.* (involving U.S. Pat. Nos. 7,431,737 and 7,896,927), Case No. SACV-01759 JST, 19 pages.
Defendant iWalk's Reply in Support of Its Motion to Transfer Venue, filed Apr. 23, 2012, *Össur hf v. iWalk, Inc.* (involving U.S. Pat. Nos. 7,431,737 and 7,896,927), Case No. SACV 01759, 18 pages.
Redacted version of Plaintiff Ossur's Disclosure of Asserted Claims and Infringement Contentions, filed Jun. 11, 2012, *Össur hf v. iWalk, Inc.* (involving U.S. Pat. Nos. 7,431,737 and 7,896,927), Case No. SACV11-01759 JST (MLGx), 223 pages.
Ossur's Claim Construction and Prehearing Statement filed Oct. 1, 2012, *Össur hf v. iWalk, Inc.* (involving U.S. Pat. Nos. 7,431,737 and 7,896,927), Case No. 12-CV-11061-FDS, 17 pages.
Defendant iWalk's Preliminary Invalidity Contentions filed Nov. 30, 2012, *Össur hf v. iWalk, Inc.* (involving U.S. Pat. Nos. 7,431,737 and 7,896,927), Case No. 12-CV-11061 FDS, 157 pages.
Ossur's Opening Claim Construction Brief filed Feb. 8, 2013, *Össur hf v. iWalk, Inc.* (involving U.S. Pat. Nos. 7,431,737 and 7,896,927), Case No. 12-CV-11061 FDS, 48 pages.
iWalk's Opening Claim Construction Brief filed Feb. 8, 2013, *Össur hf v. iWalk, Inc.* (involving U.S. Pat. Nos. 7,431,737 and 7,896,927), Case No. 12-CV-11061 FDS, 33 pages.
Request for Ex Parte Reexamination of U.S. Pat. No. 7,431,737 (without Appendices A2-A10), Control No. 90/012,731, filed Dec. 5, 2012.
Request for Ex Parte Reexamination of U.S. Pat. No. 7,896,927 (without Appendices A1-A7), Control No. 90/012,732, filed Dec. 5, 2012.
Declaration of Diane Geraci dated Jun. 26, 2012, including Exhibits A, B, and C, submitted as Appendix A3 to the Request for Ex Parte Reexamination of U.S. Pat. No. 7,431,737, filed Dec. 5, 2012 (Reference No. 563, above), and submitted as Appendix A5 to the Request for Ex Parte Reexamination of U.S. Pat. No. 7,896,927, filed Dec. 5, 2012 (Reference No. 564, above).
Au, S.K., et al. Powered Ankle-Foot Prosthesis for the Improvement of Amputee Ambulation, Proceedings of the 29th Annual International Conference of the IEEE, Aug. 23-26, 2007.
Flowers, A Man-Interactive Simulator System for Above-Knee Prosthetics Studies, Aug. 1972.
Gard, Steven A., Ph.D., Use of Quantitative Gait Analysis for the Evaluation of Prosthetic Walking Performance, Journal of Prosthetics & Orthotics, vol. 18, Issue 6, pp. P93-P104, Jan. 2006.
McNealy, Lexyne L. and Steven A. Gard, Effect of Prosthetic Ankle Units on the Gait of Persons with Bilateral Trans-Femoral Amputations, Prosthetics and Orthotics International, 2008 32:111.
Murray, M. Pat, et al. Walking Patterns of Normal Men, The Journal of Bone and Joint Surgery, vol. 46-A, No. 2, Mar. 1964.
Perry, Jacquelin, MD, Gait Analysis: Normal and Pathological Function, 1992.
Sowell, T.T., A Preliminary Clinical Evaluation of the Mauch Hydraulic Foot-Ankle System, 5 Prosthetics and Orthotics International 87 (1981).
Plaintiff Ossur's Preliminary Proposed Claim Constructions, served Sep. 20, 2012, *Össur hf v. iWalk, Inc.* (involving U.S. Pat. Nos. 7,431,737 and 7,896,927), Case No. 12-CV-11061-FDS, 10 pages.
Redacted version of Defendant iWalk's Preliminary Non-Infringement Contentions filed Nov. 30, 2012, *Össur hf v. iWalk, Inc.* (involving U.S. Pat. Nos. 7,431,737 and 7,896,927), Case No. 12-CV-11061 FDS, 20 pages.
Ossur's Identification of Claim Terms and Proposed Constructions served Feb. 1, 2013, *Össur hf v. iWalk, Inc.* (involving U.S. Pat. Nos. 7,431,737 and 7,896,927), Case No. 12-CV-11061-FDS, 8 pages.
iWalk's Identification of Disputed Claim Terms and Proposed Constructions, served Feb. 1, 2013, *Össur hf v. iWalk, Inc.* (involving U.S. Pat. Nos. 7,431,737 and 7,896,927), Case No. 12-CV-11061-FDS, 5 pages.
Ossur and iWalk's Disputed Claim Terms and Proposed Constructions, exchanged Feb. 5, 2013, *Össur hf v. iWalk, Inc.* (involving U.S. Pat. Nos. 7,431,737 and 7,896,927), Case No. 12-CV-11061-FDS, 7 pages.
Ossur's Responsive Claim Construction Brief filed Feb. 19, 2013, *Össur hf v. iWalk, Inc.* involving U.S. Pat. Nos. 7,431,737 and 7,896,927), Case No. 12-CV-11061 FDS, 23 pages.
iWalk's Responsive Claim Construction Brief filed Feb. 19, 2013, *Össur hf v. iWalk, Inc.* (involving U.S. Pat. Nos. 7,431,737 and 7,896,927), Case No. 12-CV-11061 FDS, 19 pages.
Declaration of Steven A. Gard, Ph.D., in Support of Ossur's Responsive Claim Construction Brief Regarding Purported Indefiniteness of Three Disputed Claim Terms, filed Feb. 19, 2013, *Össur hf v. iWalk, Inc.* (involving U.S. Pat. Nos. 7,431,737 and 7,896,927), Case No. 12-CV-11061 FDS, 47 pages.
iWalk's Markman Tutorial and Presentation, Feb. 25, 2013, *Össur hf v. iWalk, Inc.* (involving U.S. Pat. Nos. 7,431,737 and 7,896,927), Case No. 12-CV-11061 FDS, 94 pages.
Ossur's Claim Construction Presentation, Feb. 25, 2013, *Össur hf v. iWalk, Inc.* (involving U.S. Pat. Nos. 7,431,737 and 7,896,927), Case No. 12-CV-11061 FDS, 81 pages.
Transcript of Markman Hearing held Feb. 25, 2013, *Össur hf v. iWalk, Inc.* (involving U.S. Pat. Nos. 7,431,737 and 7,896,927), Case No. 12-CV-11061 FDS, 120 pages.
Ossur's First Amended Preliminary Infringement Disclosures, served Jan. 2013, *Össur hf v. iWalk, Inc.* (involving U.S. Pat. Nos. 7,431,737 and 7,896,927), Case No. 12-CV-11061 FDS, 192 pages.
Memorandum and Order on Claim Construction, Aug. 8, 2013, *Össur hf v. iWalk, Inc.* (involving U.S. Pat. Nos. 7,431,737 and 7,896,927), Case No. 12-CV-11061 FDS, 51 pages.

(56) References Cited

OTHER PUBLICATIONS

Response to Office Action of Jun. 20, 2013 in the Ex Parte Reexamination of U.S. Pat. No. 7,431,737, U.S. Appl. No. 90/012,731, filed Sep. 19, 2013.
Declaration of Steven A. Gard dated Sep. 19. 2013 in Ex Parte Reexaminatin of U.S. Pat. No. 7,431,737, Control No. 90/012,731, with Exhibits 1, 2, 4, 5, and 6. Exhibit 3 is omitted as it is submitted separately as reference 19 in this Information Disclosure Statement.
Response to Office Action of Jun. 14, 2013 in the Ex Parte Reexamination of U.S. Pat. No. 7,896,927, Control No. 90/012,732, filed Sep. 16, 2013.
Declaration of Steven A. Gard dated Sep. 13, 2013 in Ex Parte Reexamination of U.S. Pat. No. 7,896,927, Control No. 90/012,732.
Office Action in the Ex Parte Reexamination of U.S. Pat. No. 7,431,737, Control No. 90/012,731, dated Jun. 20, 2013.
Office Action in the Ex Parte Reexamination of U.S. Pat. No. 7,896,927, Control No. 90/012,732, dated Jun. 14, 2013.
Office Action in the Ex Parte Reexamination of U.S. Pat. No. 7,896,927, Control No. 90/012,732, dated Oct. 25, 2013.
Martin, C.W., Otto Bock C-leg: A Review of Its Effectiveness, WCB Evidence Based Group, Nov. 27, 2003.
Mayagoitia et al., "Accelerometer and Rate Gyroscope Measurement of Kinematics: An Inexpensive Alternative to Optical Motion Analysis Systems," Journal of Biomechanics, vol. 35, 2002, pp. 537-542.
Moe-Nilssen, R.; "A New Method for Evaluating Motor Control in Gait Under Real-Life Environmental Conditions. Part 1: The Instrument" Clinical Biomechanics, vol. 13, 1998, pp. 320-327.
Otto Bock, Modular Knee Joints, http://www.healthcare.ottobock.com/technical_orthopedics/beinprothesen/sites/knee.htm, printed Jul. 10, 2002, 4 pages.
International Search Report and Written Opinion in PCT Application No. PCT/US2005/004878, dated Aug. 19, 2005.
International Search Report and Written Opinion in PCT Application No. PCT/US2006/005352, dated Dec. 28, 2006.
International Preliminary Report on Patentability in PCT Application No. PCT/US2009/037982, dated Oct. 7, 2010.
Dec. 26, 2012 Office Action in Chinese Patent Application No. 200980118523.3.
Jul. 30, 2013 Office Action in Chinese Patent Application No. 200980118523.3.
Jan. 28, 2014 Office Action in Chinese Patent Application No. 200980118523.3.
Benedetti, "Gait Analysis of Patients Affected by Post-Traumatic Ankle Arthrosis Treated with Osteochondral Allograft Transplantation," SIAMOC 2006 Congress Abstracts/Gait & Posture 24S, 2006, p. S17.
Bonivento et al., "Automatic Tuning of Myoelectric Prostheses", Journal of Rehabilitation Research and Development, Jul. 1998, vol. 35, No. 3, pp. 294-304.
DIGINFO TV, "Powered Prosthetic Thigh and Leg", uploaded Nov. 7, 2008 http://www.youtube.com/watch?v=lgitTzNEd54&feature=youtu.be%3E [Screenshots retrieved Oct. 23, 2014 in 9 pages].
"Extension Spring Design Theory, Spring Rate of Extension Springs," http://web.archive.org/web/20131209120508/http://springipedia.com/extension-design-theory.asp as archived Dec. 9, 2013 in 1 page.
Michael, John W., M.Ed., "Upper Limb Powered Components and Controls: Current Concepts", Clinical Prosthetics and Orthotics, 1986, vol. 10, No. 2, pp. 66-77.
Official Communication in European Application No. 09726166.3, dated Dec. 1, 2016.

* cited by examiner

| Possible Transits: From State to State | Stance | Level Ground Walking | Ascending Stairs | Descending Stairs | Incline (up) | Decline | Sitting Down | Sitting | Standing Up | Adjust Heel Height |
|---|---|---|---|---|---|---|---|---|---|---|
| Stance | N/A | Toe Clearance | -10° | -10° | -2.5°, -5° | +2.5°, +5° | No Action | | | Set Heel Height |
| Level Ground Walking | No Action | N/A | -10° | -10° | -2.5°, -5° | +2.5°, +5° | | | | |
| Ascending Stairs | User Setpoint | Toe Clearance | N/A | -10° | -2.5°, -5° | | | | | |
| Descending Stairs | User Setpoint | Toe Clearance | -10° | N/A | -2.5°, -5° | +2.5°, +5° | | | | |
| Incline (up) | No Action | Toe Clearance | -10° | | N/A | +2.5°, +5° | | | | |
| Decline | No Action | Toe Clearance | | -10° | -2.5°, -5° | N/A | | | | |
| Sitting Down | | | | | | | | Relax Ankle | N/A | |
| Sitting | | | | | | | N/A | | User Setpoint | N/A |
| Standing Up | User Setpoint | Toe Clearance | | | | | User Setpoint | N/A | | Set Heel Height |
| Adjust Heel Height | User Setpoint | | | | | | User Setpoint | User Setpoint | N/A | |

FIG. 10

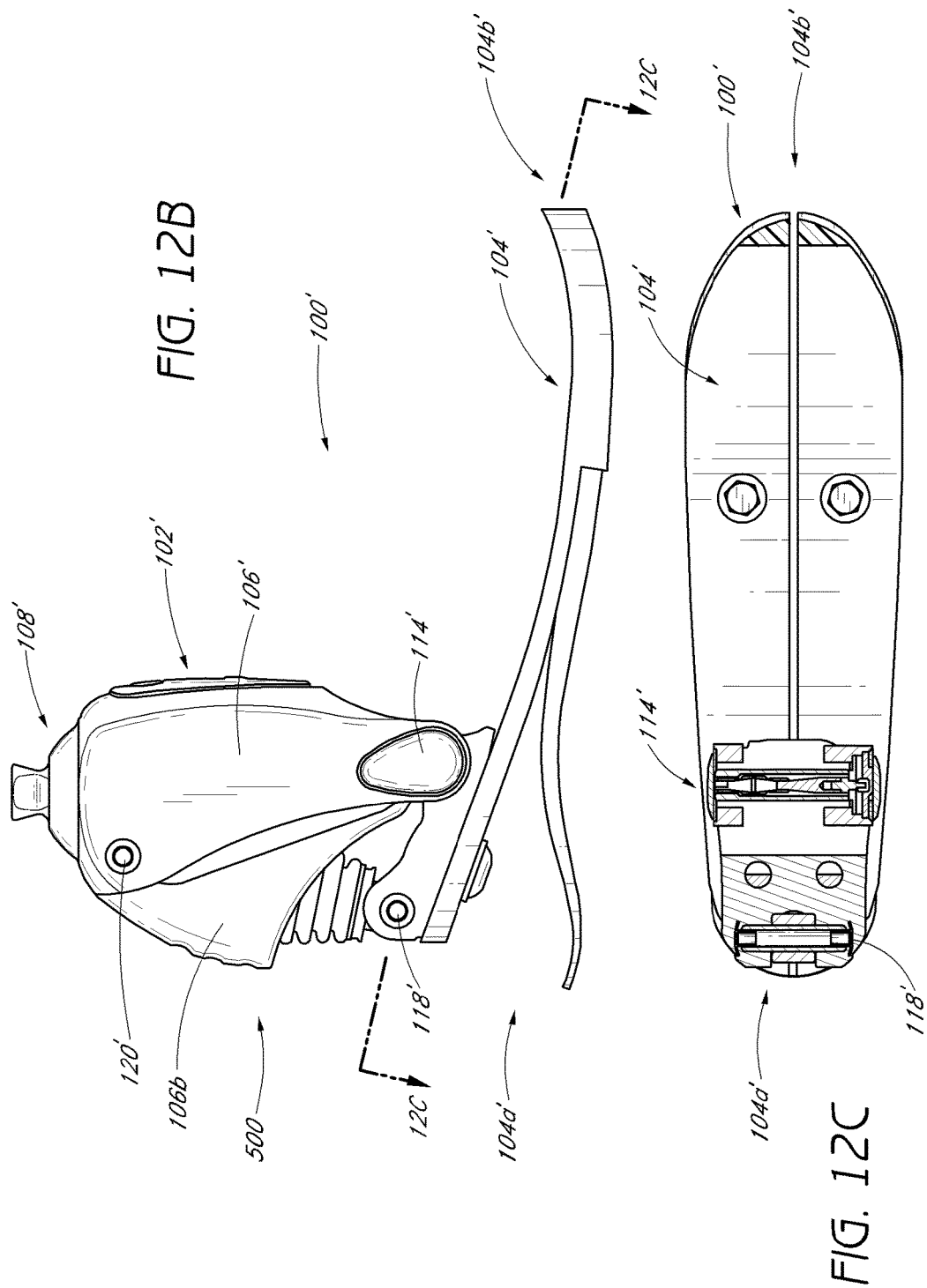

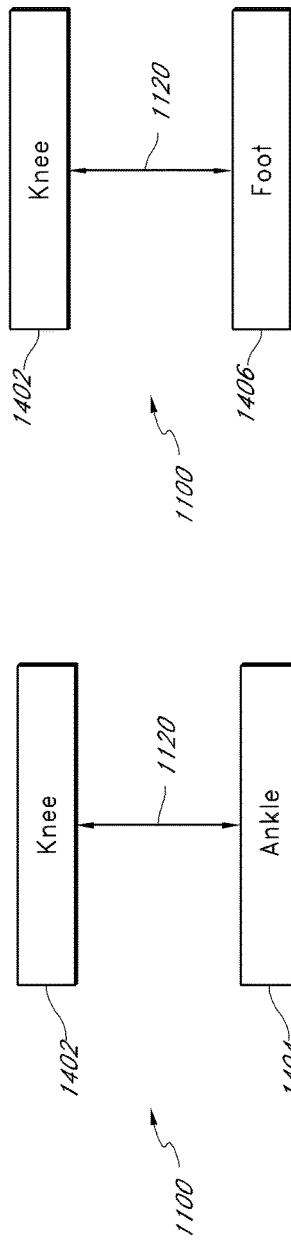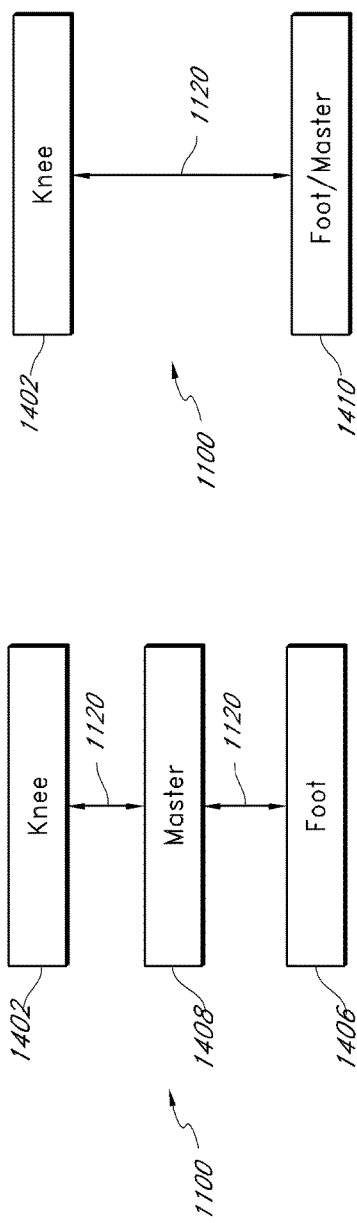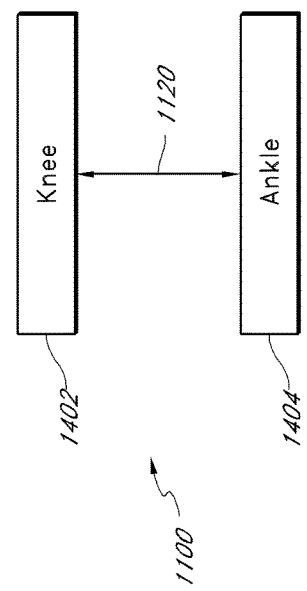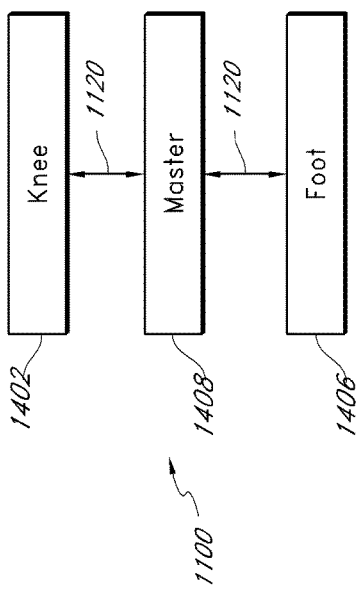

TRANSFEMORAL PROSTHETIC SYSTEMS AND METHODS FOR OPERATING THE SAME

RELATED APPLICATIONS

This application is a divisional of U.S. patent application Ser. No. 12/409,336, filed Mar. 23, 2009, which claims priority to U.S. Provisional Application No. 61/039,055, filed Mar. 24, 2008, and which is a continuation-in-part of U.S. patent application Ser. No. 11/355,047, filed Feb. 15, 2006, which claims priority to U.S. Provisional Application Nos. 60/653,717 and 60/679,953, filed Feb. 16, 2005 and May 10, 2005, respectively; U.S. patent application Ser. No. 12/409,336 is also a continuation-in-part of U.S. patent application Ser. No. 11/056,344, filed Feb. 11, 2005, which claims priority to U.S. Provisional Application Nos. 60/544,259 and 60/588,232, filed Feb. 12, 2004 and Jul. 15, 2004, respectively. Each of the above mentioned applications is incorporated herein by reference in its entirety and should be considered part of this specification.

BACKGROUND

Field of the Invention

The present invention relates to prosthetic and orthotic limbs in general and, in addition, to systems and methods for configuring, synchronizing, and optimizing the adaptive control systems of prosthetic and orthotic devices on a patient.

Description of the Related Art

Millions of individuals worldwide rely on prosthetic and/or orthotic devices to compensate for disabilities, such as amputation or debilitation, and to assist in the rehabilitation of injured limbs. Orthotic devices include external apparatuses used to support, align, prevent, protect, correct deformities of, or improve the function of movable parts of the body. Prosthetic devices include apparatuses used as artificial substitutes for a missing body part, such as an arm or leg.

The number of disabled persons and amputees is increasing each year as the average age of individuals increases, as does the prevalence of debilitating diseases such as diabetes. As a result, the need for prosthetic and orthotic devices is also increasing. Conventional orthoses are often used to support a joint, such as an ankle or a knee, of an individual, and movement of the orthosis is generally based solely on the energy expenditure of the user. Some conventional prostheses are equipped with basic controllers that artificially mobilize the joints without any interaction from the amputee and are capable of generating only basic motions. Such basic controllers do not take into consideration the dynamic conditions of the working environment. The passive nature of these conventional prosthetic and orthotic devices typically leads to movement instability, high energy expenditure on the part of the disabled person or amputee, gait deviations and other short- and long-term negative effects. This is especially true for leg orthoses and prostheses.

Prosthetic and orthotic devices, such as are attached to a human limb, have benefited from advances in electronics. Electronically controlled prosthetic or orthotic devices, which may be generally referred to as "mechatronic" devices, for example, prosthetic ankles or knees, can provide safer and more natural movement to patients who are equipped with such systems. However, advances in electronics appear to have outpaced the advances in control systems. Thus, control systems for prosthetic systems can benefit from intelligent architectures.

Further, the proliferation of electronic control systems for prosthetic and orthotic systems has created a need for systems and methods of synchronizing multiple devices which are worn by a single patient, e.g., a prosthetic knee and a prosthetic ankle. Operating in isolation from each other, multiple control systems may fail to provide the patient with stable, coordinated movement. In addition, independent configuration of multiple prosthetic devices can be inconvenient. Thus, it is desirable to have systems and methods of configuration, communication, and synchronization between such control systems. Further, it is desirable to have systems and methods of adding, replacing, or augmenting portions of the software in such control systems.

SUMMARY OF CERTAIN EMBODIMENTS

Accordingly, one embodiment of the invention includes a prosthetic or orthotic system that is self-powered and that mimics the natural movement of a healthy limb, and in particular, the movement of a healthy ankle. Another embodiment of the invention includes a sensor system and a control system that manage the motion of the prosthetic or orthotic system so as to facilitate movement by the disabled person or amputee.

One embodiment of the invention includes a system associated with the movement of a limb. In one embodiment, the system comprises a foot unit; an attachment member having an upper end and a lower end, wherein the lower end is pivotably attached to a first location on the foot unit; and an actuator operatively coupled to the foot unit and to the attachment member, wherein the actuator is configured to actively adjust an angle between the attachment member and the foot unit. For example, the foot unit may be a prosthetic or orthotic device.

Another embodiment of the invention includes a prosthetic system for mimicking the natural movement of an ankle. In one embodiment, the prosthetic system comprises a prosthetic foot; a pivot assembly attached to a first position on the prosthetic foot, wherein the first position is near a natural ankle location of the prosthetic foot; a lower limb member extending in a tibial direction, the lower limb member having an upper end and a lower end, wherein the lower end of the lower limb member is operatively coupled to the pivot assembly; and an actuator operatively coupled to the prosthetic foot and to the lower limb member, wherein the actuator is configured to actively adjust an angle between the lower limb member and the prosthetic foot about the pivot assembly.

One embodiment of the invention includes a method for controlling a device associated with the movement of a limb. In one embodiment, the method comprises monitoring with at least one sensor the movement of an actuatable device associated with a limb; generating data indicative of said movement; processing the data with a processing module to determine a current state of locomotion of the actuatable device; and adjusting the actuatable device based on the determined state of locomotion, wherein said adjusting comprises substantially mimicking the movement of a healthy ankle. For example, the actuatable device may be a prosthesis or an orthosis.

Another embodiment of the invention includes a method for controlling a prosthetic ankle device. In one embodiment, the method comprises monitoring with at least one sensor the movement of an actuatable prosthetic ankle device, wherein the at least one sensor generates data indicative of the movement of the prosthetic ankle device; receiving and processing the data with a control module to determine a current state of locomotion of the actuatable prosthetic ankle device; outputting with the control module at least one control signal based on the determined state of locomotion; and adjusting the actuatable prosthetic ankle device based at least upon the control signal, wherein said adjusting comprises substantially mimicking the movement of a healthy ankle.

In one embodiment, a prosthetic or orthotic system is provided having an ankle-motion-controlled foot. The prosthetic or orthotic system comprises, among other things, a lower limb member, an actuator, and a foot unit. The actuator is configured to mimic the motion of an ankle by adjusting the angle between the lower limb member and the foot unit. The prosthetic or orthotic system also comprises an attachment portion that facilitates coupling of the lower limb member to another prosthetic or orthotic member, to the stump of an amputee, or to another component. The prosthetic or orthotic system may also comprise a rechargeable battery to provide power to the actuator or other components of the system. Embodiments of the invention include systems for both transtibial and transfemoral amputees.

In another embodiment of the invention, the prosthetic or orthotic system comprises a sensor system that is used to capture information regarding the position and movement of the prosthetic or orthotic device. This information may be processed in real-time so as to predict appropriate movements for the prosthetic or orthotic device and to adjust the prosthetic or orthotic device accordingly.

In one embodiment of the invention, a system architecture is provided having a sensor module, a central processing unit, a memory, an external interface, a control drive module, an actuator, and an ankle device. The system architecture may receive instructions and/or data from external sources, such as a user or an electronic device, through the external interface.

In one embodiment, a control system may also be provided that manages the movement of the orthosis or the prosthesis. In one embodiment, the control system manages the movement of an actuator, such as a screw motor. Such motion control provides for movement by the user up inclined surfaces, down declines, or on stairs. In one embodiment, the control system may be configured to monitor through sensors the movements of a healthy limb and use the measurements to control the movement of the prosthesis or orthosis. The control system may also manage the damping of the actuator or other portions of the orthosis or prosthesis.

In one embodiment, a method is provided for controlling actuation of a prosthetic or orthotic device. The method comprises providing one or more sensors on an actuatable prosthetic or orthotic device. Data received from the sensors is processed and is used to determine the current state of locomotion for the prosthetic device. A processing unit, using at least a portion of the data received from the sensors, then predicts movement of the prosthetic or orthotic device. In one embodiment, a prosthetic ankle is provided that mimics the movement of a healthy ankle. The one or more sensors may comprise, for example, gyroscopes and/or accelerometers. In another embodiment of the invention, adjustments are not made to the actuatable prosthetic or orthotic device unless the locomotion type of the user is determined by the processing unit to have a security factor above a predetermined threshold value.

In another embodiment, a method is provided for identifying motion of an orthotic or prosthetic device. The method comprises receiving data from one or more sensors placed on an orthotic or prosthetic device while the device is moving. A waveform is generated from the data received by the sensors. A specific motion for the orthotic or prosthetic device is identified by correlating the waveform with known waveforms for particular types of motion. For example, known waveforms may be inputted by a user or downloaded from an external device or system. The waveforms may also be stored in a memory on the prosthetic or orthotic device.

In another embodiment, a method is provided for actuating an ankle-assisting device. The device is actuated by providing a computer control to provide relative motion between a first and a second portion of the device. In one embodiment, the device is an orthosis. In another embodiment, the device is a prosthesis. In one embodiment, the computer control predicts future motion of the device. In another embodiment, the computer control receives input from at least one sensor module that receives information regarding environmental variables and/or the movement or position of the prosthetic or orthotic device. In another embodiment, the computer control receives input from at least one sensor module that receives information regarding the movement or position of a healthy limb.

One embodiment of the invention includes a device configured to be attached to a limb. The device comprises a first portion and a second portion, the first and second portions being moveable relative to each other to mimic a natural human joint. The device also comprises an actuator coupling the first and second portions together and configured to adjust the angle between the first and second portions. The actuator comprises a rotor operatively coupled to a stator and a motor configured to rotate the rotor, wherein the actuator is selectively locked during a desired phase in a gait cycle.

Another embodiment of the invention includes a device configured to be attached to a limb. The device comprises a first portion and a second portion, the first and second portions being moveable relative to each other to mimic a natural human joint. The device also comprises an actuator coupling the first and second portions together and configured to adjust the angle between the first and second portions. The actuator comprises a rotor operatively coupled to a stator and a motor configured to rotate the rotor. The device also comprises means for minimizing friction against the rotor.

Still another embodiment of the invention includes a device configured to be attached to a limb. The device comprises a first portion and a second portion, the first and second portions being moveable relative to each other to mimic a natural human joint. The device also comprises an actuator coupling the first and second portions together and configured to adjust the angle between the first and second portions. The actuator comprises a rotor operatively coupled to a stator and a motor configured to rotate the rotor, wherein the motor is disposed about the rotor.

Another embodiment of the invention includes a prosthetic device configured to be attached to a limb. The device comprises a prosthetic foot and a pivot assembly attached to the prosthetic foot, the pivot assembly mimicking a natural human ankle joint. The device also comprises a support member having an upper end and a lower end, wherein the lower end of the support member is operatively coupled to the pivot assembly. The prosthetic device also comprises an actuator operatively coupled to the prosthetic foot and the support member, the actuator configured to adjust an angle between the support member and the prosthetic foot about the pivot assembly, wherein the actuator is selectively locked during a desired phase of a gait cycle of the prosthetic foot.

In still another embodiment, an actuator is provided, comprising an elongate member extending about a major axis of the actuator. The actuator also comprises a rotor rotatably coupled to the elongate member and a stator operatively coupled to the rotor. At least one magnet is disposed between the rotor and the stator, the magnet configured to apply a magnetic force between the rotor and the stator. The actuator also comprises a motor configured to rotate the rotor relative to the elongate member, wherein the at least one magnet is configured to minimize friction between the rotor and the stator.

In another embodiment of the invention, an actuator is provided, comprising an elongate member extending about a major axis of the actuator. The actuator also comprises a rotor rotatably coupled to the elongate member and a stator operatively coupled to the rotor. A ball bearing is disposed between the rotor and the stator. The actuator also comprises a motor configured to rotate the rotor relative to the elongate member, wherein the ball bearing is configured to minimize friction between the rotor and the stator.

In yet another embodiment of the invention, an actuator is provided, comprising an elongate member extending about a major axis of the actuator. A rotor is rotatably coupled to the elongate member and a stator operatively coupled to the rotor. The actuator also comprises a motor disposed about the rotor and configured to rotate the rotor relative to the elongate member.

In another embodiment, an actuator is provided, comprising an elongate member extending about a major axis of the actuator. The actuator also comprises a rotor rotatably coupled to the elongate member, a retainer disposed about the rotor, and a stator operatively coupled to the rotor. A motor is configured to rotate the rotor relative to the elongate member, wherein the rotor and the retainer selectively engage to inhibit rotation of the rotor.

In another embodiment, a method of operating a prosthetic device attached to a limb is provided. The method comprises providing a prosthetic device configured to attach to a limb, the device mimicking a natural human joint and having a first portion and a second portion, the portions moveable relative to each other about the joint. The method also comprises providing an actuator coupled to the first portion and the second portion, adjusting an angle between the first portion and the second portion and selectively locking the actuator during a desired phase of a gait cycle.

In still another embodiment, a method of operating a prosthetic device attached to a limb is provided. The method comprises providing a prosthetic device configured to attach to a limb, the device mimicking a natural human joint and having a first portion and a second portion, the portions moveable relative to each other about the joint. The method also comprises providing an actuator coupled to the first portion and the second portion, adjusting an angle between the first portion and the second portion and actively minimizing friction against a rotor of the actuator during a desired phase in a gait cycle.

In another embodiment, a system is disclosed for sensing a rotational movement of a lower-limb prosthetic device. The system includes a prosthetic foot and an attachment member having an upper end and a lower end. The system also includes a pivot assembly rotatably coupling the lower end of the attachment member to the prosthetic foot to allow for rotation of the prosthetic foot about a pivot axis extending through the pivot assembly, wherein the pivot assembly is configured to substantially mimic a natural ankle joint The system further includes a sensor assembly coupled to the pivot assembly and configured to detect the rotation of the prosthetic foot about the pivot axis, wherein at least a portion of the sensor assembly is configured to rotate about the pivot axis and is securely positioned along the pivot axis to substantially eliminate other movement.

In another embodiment, a system is disclosed for sensing a rotational movement of a device associated with a limb. The system includes a foot unit and an attachment member having an upper end and a lower end. The system also includes a pivot assembly rotatably coupling the lower end of the attachment member to the foot unit to allow for rotation of the foot unit about an axis extending through the pivot assembly, wherein the pivot assembly is configured to substantially mimic a natural ankle joint. The system further includes a sensor assembly coupled to the pivot assembly and configured to detect the rotation of the foot unit about the axis and to substantially neglect axial and radial movement of the foot unit with respect to the axis.

In another embodiment, a system is disclosed for sensing a rotational movement of a device associated with a lower limb. The system includes a foot means for contacting a ground surface and a means for attaching the foot means to a patient. The system also includes a means for pivotably coupling the foot means to a lower end of the means for attaching to allow for rotation of the foot means about an axis extending through the means for pivotably coupling, wherein the means for pivotably coupling substantially mimics an ankle joint. The system further includes a means for sensing coupled to the means for pivotably coupling, the means for sensing further configured to detect the rotation of the foot means about the axis and to substantially neglect axial and radial movement of the foot means with respect to the axis.

In another embodiment, a prosthetic system is disclosed that mimics the movement of a natural ankle in a relaxed position. The prosthetic system comprises a prosthetic ankle joint comprising a foot unit and an upper member moveably attached to the foot unit to simulate a natural human ankle joint. The system further comprises a controller configured to automatically adjust the state of the prosthetic ankle joint, wherein the controller is configured to automatically adjust the prosthetic ankle joint to a relaxed state upon receiving data indicative of a user's movement to a relaxed position.

In another embodiment, a prosthetic system is disclosed for mimicking the natural movement of an ankle in a relaxed position. The prosthetic system comprises a prosthetic foot. The prosthetic system further comprises a pivot assembly attached to a first location on the prosthetic foot, wherein the first location is near a natural ankle location of the prosthetic foot. The prosthetic system further comprises a lower limb member extending in a tibial direction, the lower limb member having an upper end and a lower end, wherein the lower end of the lower limb member is operatively coupled to the pivot assembly. The prosthetic system further comprises an actuator coupled to the prosthetic foot and to the lower limb member, wherein the actuator is configured to adjust an angle between the lower limb member and the prosthetic foot about the pivot assembly. The prosthetic system further comprises at least one sensor configured to detect a position of a user of the prosthetic system. The prosthetic system further comprises a controller configured to operate the actuator. With regards to the prosthetic system described, the at least one sensor is configured to transmit data to the controller indicative of when the user is in a relaxed position, said relaxed position determined by the user positioning the prosthetic system within a range of defined angles relative to a ground surface for a defined amount of time and the prosthetic system having an acceleration less than a maximum threshold value, and wherein the controller is configured to operate the actuator to cause an angle between the prosthetic foot and the lower limb assembly to increase about the pivot assembly such that the prosthetic foot becomes more plantarflexed relative to the lower limb assembly.

In another embodiment, a method is disclosed for adjusting a prosthetic ankle device. The method comprises monitoring with at least one sensor the movement of a user of a prosthetic ankle device. The method further comprises generating data indicative of the movement. The method further comprises processing the data with a processing module to determine whether the user is in a relaxed position. The method further comprises adjusting the prosthetic ankle device based on whether the user is in a relaxed position, wherein adjusting the prosthetic ankle device comprises automatically adjusting a configurable element of the prosthetic ankle device.

In another embodiment, a method is disclosed for adjusting a prosthetic ankle device comprising a prosthetic foot and a limb member moveably connected at a location about a natural human ankle joint. The method comprises measuring with at least one sensor the angle of the prosthetic ankle device relative to a ground surface and an acceleration of the device. The method further comprises determining whether the angle of the prosthetic ankle device relative to the ground surface falls within a defined range of angles. The method further comprises determining whether the acceleration of the device is above or below a threshold acceleration. The method further comprises adjusting an angle between the prosthetic foot and the limb member to a plantarflexed or dorsiflexed configuration upon determining that the angle of the ankle device relative to the ground surface falls within the defined range of angles and upon determining that the acceleration of the device is above or below the threshold acceleration.

In another embodiment, a method is disclosed for operating a prosthetic ankle worn by a user. The method comprises providing a prosthetic ankle comprising a foot unit and a lower limb member, the foot unit and lower limb member configured to rotate at about a location of a natural human ankle. The method further comprises detecting an incline or decline of a surface while the user moves with the prosthetic ankle. The method further comprises adjusting an angle between the foot unit and the lower limb member based on the detected incline or decline.

In another embodiment, a method is disclosed for operating a prosthetic ankle worn by a user. The method comprises providing a prosthetic ankle comprising a foot unit and a lower limb member, the foot unit and the lower limb member configured to rotate at about a location of a natural human ankle. The method further comprises measuring a terrain variable upon which the user moves with the prosthetic ankle. The method further comprises adjusting an angle between the foot unit and the lower limb member based on the measured terrain variable.

In another embodiment, a method is disclosed for operating a prosthetic ankle worn by a user. The method comprises providing a prosthetic ankle comprising a foot unit and a lower limb member, the foot unit and the lower limb member configured to rotate at about a location of a natural human ankle. The method further comprises measuring a surface angle of a surface upon which the user moves with the prosthetic ankle. The method further comprises calculating a desired angle between the foot unit and the lower limb member for moving upon the surface, wherein the calculation is based at least in part on the measured surface angle. The method further comprises adjusting an angle between the foot unit and the lower limb member to the desired angle.

One embodiment is a system for controlling motion of a human limb. The system may include a plurality of mechatronic devices. Each of the plurality of mechatronic devices is in communication with at least one other of the plurality of mechatronic devices. At least one of the mechatronic devices controls an actuator. In one such embodiment, at least one of the plurality of mechatronic devices is configured to generate a control state for at least one other of the plurality of mechatronic devices based on the communicated data. In one embodiment, the communicated data is used to synchronize the mechatronic devices. In one embodiment, each of the mechatronic devices comprises an artificial joint. In one embodiment, at least one of the plurality of mechatronic devices comprises a prosthetic knee and at least one of the mechatronic devices comprises a prosthetic ankle.

Another embodiment is a mechatronic device for controlling motion of a human limb in cooperation with at least one other mechatronic device. The mechatronic device includes a communication interface configured to communicate data with the at least one other mechatronic device, a sensor configured to obtain a value indicative of at least one motion parameter of the limb; an actuator configured to affect at least one motion parameter of the mechatronic device, and a processor configured to activate the actuator based on the received communicated data and the at least one motion parameter value. In one embodiment, the communicated data may include the parameter value obtained from the sensor. In another embodiment, the communicated data may include state machine data received from the other mechatronic devices. In yet another embodiment, the communicated data may include configuration data received from the other mechatronic devices.

Another embodiment is a mechatronic device for controlling motion of a human limb in cooperation with at least one other mechatronic device. The mechatronic device includes a communication interface configured to communicate data with the at least one other mechatronic device, and a processor configured to generate a control state of the at least one other mechatronic device. The processor is further configured to communicate data associated with the control state through the communication interface. The mechatronic device further includes an actuator controlled by the processor so as to effectuate movement of the human limb. In another embodiment, the communicated data may include software that when executed by the processor is configured to affect the selection of the control state. In one embodiment, the communicated data includes data obtained by the at least one sensor of the other mechatronic device. In one embodiment, the communicated data includes configuration data obtained by the at least one sensor of the other mechatronic device. In one embodiment, the processor is further configured to determine at least one actuator control command based on the control state, and wherein the communicated data includes the at least one actuator control command.

Another embodiment is a method of synchronizing a first mechatronic device with a second mechatronic device. The method includes communicating data from the second mechatronic device to the first mechatronic device. The method further includes generating a control state in response to the received data. The method further includes controlling an actuator on the second mechatronic device based at least in part on the control state. In one embodiment, the method further includes generating a command to control an actuator of the second mechatronic device in response to the control state. In one embodiment, the method further includes generating a command to control an actuator of the first mechatronic device in response to the communicated data. In one embodiment, the received data includes sensor data received from the second mechatronic device. In another embodiment, the received data includes at least a portion of information indicative of the control state. In yet another embodiment, the received data includes computer software and the control state is performed at least partly by executing the computer software.

Another embodiment is a system for controlling motion of a device associated with a limb. The system includes a mechatronic device. The system further includes a sensor associated with a human limb which provides motion parameter data to the mechatronic device. The mechatronic device uses the motion parameter data for synchronization. In one embodiment, the sensor receives signals from the human nervous system. In one embodiment, the sensor receives signals from a sensor associated with a sound limb. In one embodiment, the motion parameter data is used for synchronization with another mechatronic device. In one such embodiment, the other mechatronic device provides motion parameter data to the mechatronic device.

One embodiment is a method of synchronizing a computing device with a device associated with a limb. The method includes communicating data between the mechatronic system and the computing device, storing the data on the computing device, generating a control state on the mechatronic system in response to the data, and controlling an actuator on the second mechatronic system based at least in part on the control state.

Another embodiment is a mechatronic system attached to a human body. The device includes a sensor configured to provide data indicative of movement of the human body. An actuator is configured to control movement of at least a portion of the human body. A processor is configured to execute instructions configured to control the actuator based on the sensor data. A communication interface is configured to communicate data with a data source. The processor is further configured to receive at least a portion of the instructions from the data source. In one embodiment, the mechatronic system may include a separation of the processing, sensing, actuation, and communications in two or more mechatronic devices.

In one embodiment a transfemoral prosthetic device capable of mimicking the gait of a healthy leg is provided. The transfemoral prosthetic device has a foot unit, and a tibial member with an upper and lower end. The lower end of the tibial member is pivotably attached to a location on the foot unit. A first actuator is operatively coupled to the foot unit and to the tibial member, and configured to actively adjust an angle between the tibial member and the foot unit. The transfemoral prosthetic device also has a femoral member with an upper end and a lower end. The lower end of the femoral member is pivotably attached to the upper end of the tibial member. A second actuator is operatively coupled to the tibial member and to the femoral member, and is configured to actively adjust an angle between the femoral member and the tibial member.

In another embodiment, a method of controlling a transfemoral prosthetic device is provided. The method includes monitoring, with at least one sensor, at least one of position and movement of a transfemoral prosthetic device, where the device includes a foot unit, a tibial member pivotally attached to the foot unit, a first actuator operatively coupled to the foot unit and to the tibial member, a femoral member pivotally attached to the tibial member, and a second actuator operatively coupled to the tibial member and to the femoral member. The first actuator is configured to adjust an ankle angle between the foot unit and the tibial member and the second actuator is configured to adjust a knee angle between the tibial member and the femoral member. The method also includes generating data indicative of the at least one of position and movement and processing the data with a processing module to determine a gait cycle phase. In addition, the method includes actuating the first actuator during a swing phase to move the foot unit relative to the tibial member in a manner that substantially mimics the movement of a healthy ankle and actuating the second actuator during the swing phase to move the tibial member relative to the femoral member in a manner that substantially mimics the movement of a healthy knee joint attached to a healthy ankle joint.

In another embodiment, a method for controlling a transfemoral prosthetic device is provided. The method includes monitoring, with at least one sensor, at least one of position and movement of a transfemoral device associated with a limb throughout at least one gait cycle, where the device includes a foot unit, a tibial member pivotally attached to the foot unit, a first actuator operatively coupled to the foot unit and to the tibial member, a femoral member pivotally attached to the tibial member, and a second actuator operatively coupled to the tibial member and to the femoral member. The first actuator is configured to adjust an ankle angle between the foot unit and the tibial member and the second actuator is configured to adjust a knee angle between the tibial member and the femoral member. The method further includes generating data indicative of the at least one of position and movement throughout at least one gait cycle and processing the data with a processing module to determine if the data corresponds to one of a plurality of defined terrains, where the information defining the plurality of terrains is stored in memory of the device. The method further includes determining ankle-angle adjustments and knee-angle adjustments corresponding to a determined terrain and adjusting the device based on the determined ankle-angle adjustments and knee-angle adjustments corresponding to the determined terrain. The adjusting comprises actuating the first actuator to move the tibial member relative to the foot unit in a manner substantially mimicking movement of a healthy ankle. The ankle-angle adjustments are applied over a swing phase of subsequent gait cycles until a state transition is detected from the determined terrain to a different terrain. The adjusting further includes actuating the second actuator to move the femoral member relative to the tibial member in a manner substantially mimicking movement of a healthy knee attached to a healthy ankle.

In still another embodiment, a method of using a motion-controlled ankle device with a transfemoral prosthetic device to mimic natural transfemoral gait is provided. The method includes selecting a transfemoral device that is approximately the same length as a healthy leg and attaching a motion-controlled ankle device to the transfemoral prosthetic device, wherein the motion-controlled ankle device is capable of mimicking healthy ankle movement by providing toe clearance during swing. The method further includes walking with the transfemoral prosthetic device without substantially adjusting the hip movement necessary for normal, healthy walking.

In still another embodiment, a method of using a motion-controlled ankle device with a transfemoral prosthetic device to mimic natural transfemoral gait is provided. The method includes selecting a transfemoral device that is approximately the same length as a healthy leg, attaching a motion-controlled ankle device to the transfemoral prosthetic device, wherein the motion-controlled ankle device is capable of mimicking healthy ankle movement by adjusting to different terrains, and walking with the transfemoral prosthetic device without substantially adjusting the hip movement necessary for normal, healthy walking.

In yet another embodiment, prosthetic system for a transfemoral user is provided. The system includes a prosthetic knee device; and a prosthetic ankle device configured to lift a toe portion of the prosthetic ankle device during swing. The system may further include a single controller to actuate the prosthetic knee device and the prosthetic ankle device. Additionally and/or alternatively, the prosthetic ankle device may be further configured to optimize the functionality of the prosthetic knee device.

In another embodiment, a method of optimizing a prosthetic device for another prosthetic device is provided. The method includes providing a first prosthetic device; providing a second prosthetic device operable in conjunction with the first prosthetic device; and operating the second prosthetic device to optimize the operation of the first prosthetic device. The method further including synchronizing the movement of the first prosthetic device and the second prosthetic device.

In still another embodiment, a method for operating a prosthetic system for a transfemoral user is provided. The method includes providing a prosthetic knee, the knee having an upper leg portion and a lower leg portion that are articulatable about a knee joint; providing a prosthetic ankle to the prosthetic knee, the prosthetic ankle having a leg portion and a foot portion that are articulatable about an ankle joint; operating the prosthetic ankle to optimize the operation of the prosthetic knee for a transfemoral user. In some embodiments, a prosthetic ankle device is optimized for a transfemoral user by adjusting to terrain conditions more rapidly than for transtibial users by, for example, reducing the number of monitored steps before adjusting the device. In some embodiments, a prosthetic ankle device is optimized for a transfemoral user by reducing the minimum speed at which toe clearance is provided. In some embodiments, a prosthetic ankle device is optimized for a transfemoral user by enabling, disabling, or modifying a relaxed mode. In some embodiments, a prosthetic ankle device is optimized for a transfemoral user by calibrating the device, in a learn mode, for a transfemoral user. In some embodiments, a prosthetic ankle device is optimized for a transfemoral user by providing for toe clearance during steeper declines than would be provided for a transtibial user. In some embodiments, a prosthetic ankle device is optimized for a transfemoral user by enabling, disabling, or modifying a stairs mode.

In yet another embodiment, a method of optimizing a prosthetic device for a physiological condition is provided. The method includes providing a prosthetic device whose function affects a physiological condition, and optimizing the prosthetic device for the physiological condition.

In one embodiment, a transfemoral prosthetic device associated with a limb is provided that comprises a foot unit and a tibial member pivotally attached to the foot unit. A first actuator is operatively coupled to the foot unit and to the tibial member and is configured to adjust an ankle angle between the foot unit and the tibial member. A femoral member is pivotally attached to the tibial member to define a knee joint. A second actuator is operatively coupled to the tibial member and to the femoral member, and is configured to adjust a knee angle between the tibial member and the femoral member. At least one sensor is disposed on the transfemoral device and is configured to monitor at least one of position and movement of the transfemoral device throughout at least one gait cycle and to generate data indicative of the at least one of position and movement throughout the at least one gait cycle. The transfemoral prosthetic device also comprises a memory module. A processing module is configured to determine when the data corresponds to one of a plurality of defined terrains. The information defining the plurality of terrains is stored in the memory module. The processing module is further configured to determine ankle-angle adjustments and knee-angle adjustments corresponding to the defined terrain. Based on the determined ankle-angle adjustments and knee-angle adjustments, the processing module is further configured to actuate the first actuator to adjust the foot unit relative to the tibial member in a manner substantially mimicking movement of a healthy ankle and actuate the second actuator to adjust the femoral member relative to the tibial member in a manner substantially mimicking movement of a healthy knee. The ankle-angle adjustments are applied over a swing phase of subsequent gait cycles until a terrain transition is detected.

In another embodiment, a method of controlling a transfemoral prosthetic device is provided. The method comprises monitoring, with at least one sensor, at least one of position and movement of a transfemoral prosthetic device. The device comprises a foot unit, a tibial member pivotally attached to the foot unit, and a first actuator operatively coupled to the foot unit and to the tibial member. The first actuator is configured to actively adjust an ankle angle between the foot unit and the tibial member. A femoral member is pivotally attached to the tibial member. A second actuator is operatively coupled to the tibial member and to the femoral member and is configured to adjust a knee angle between the tibial member and the femoral member. The method further comprises generating data indicative of the at least one of position and movement. The data is then processed to determine a gait cycle phase. During a swing phase of the gate cycle phase, the first actuator is actuated to move the foot unit relative to the tibial member in a manner that substantially mimics the movement of a healthy ankle and the second actuator is actuated to move the tibial member relative to the femoral member in a manner that substantially mimics the movement of a healthy knee joint attached to a healthy ankle joint.

In another embodiment, a transfemoral prosthetic system capable of mimicking the gait of a healthy leg is provided. The system comprises a foot unit and a tibial member having an upper end and a lower end. The lower end is pivotably attached to the foot unit. A first actuator is operatively coupled to the foot unit and to the tibial member and is configured to actively adjust an angle between the tibial member and the foot unit. A femoral member has an upper end and a lower end. The lower end is pivotably attached to the upper end of the tibial member. A second actuator is operatively coupled to the tibial member and to the femoral member and is configured to actively adjust an angle between the femoral member and the tibial member.

After considering this discussion, and particularly after reading the section entitled "Detailed Description of Certain Embodiments" one will understand how the features of this invention provide advantages that include providing a prosthetic or orthotic control system that provides more natural and comfortable movement to its users and enabling a more convenient and intuitive configuration, addition, replacement, or augmentation of control system software.

For purposes of summarizing, certain aspects, advantages and novel features have been described herein. It is to be understood that not necessarily all such advantages may be achieved in accordance with any particular embodiment. Thus, the invention may be embodied or carried out in a manner that achieves one advantage or group of advantages as taught herein without necessarily achieving other advantages as may be taught or suggested herein.

BRIEF DESCRIPTION OF THE DRAWINGS

FIG. 10 is a table illustrating control signals usable to adjust the ankle angle of a prosthetic or orthotic system according to one embodiment of the invention.

FIG. 12B is a side view of the lower limb prosthesis of FIG. 12A.

FIG. 12C is a cross-sectional view of the lower limb prosthesis of FIG. 12B along plane M-M.

FIG. 26A is a schematic block diagram of an exemplary embodiment of the system of FIG. 1 that includes a prosthetic knee and a prosthetic ankle.

FIG. 26B is a schematic block diagram of an exemplary embodiment of the system of FIG. 1 that includes a prosthetic knee and a prosthetic foot.

FIG. 26C is a schematic block diagram of another exemplary embodiment of the system of FIG. 1 that includes a prosthetic knee, a prosthetic foot, and a master device.

FIG. 26D is a schematic block diagram of another exemplary embodiment of the system of FIG. 1 that includes a prosthetic knee and a prosthetic foot in which the prosthetic foot includes one or more state machines for controlling both devices.

DETAILED DESCRIPTION OF CERTAIN EMBODIMENTS

Figure 1:
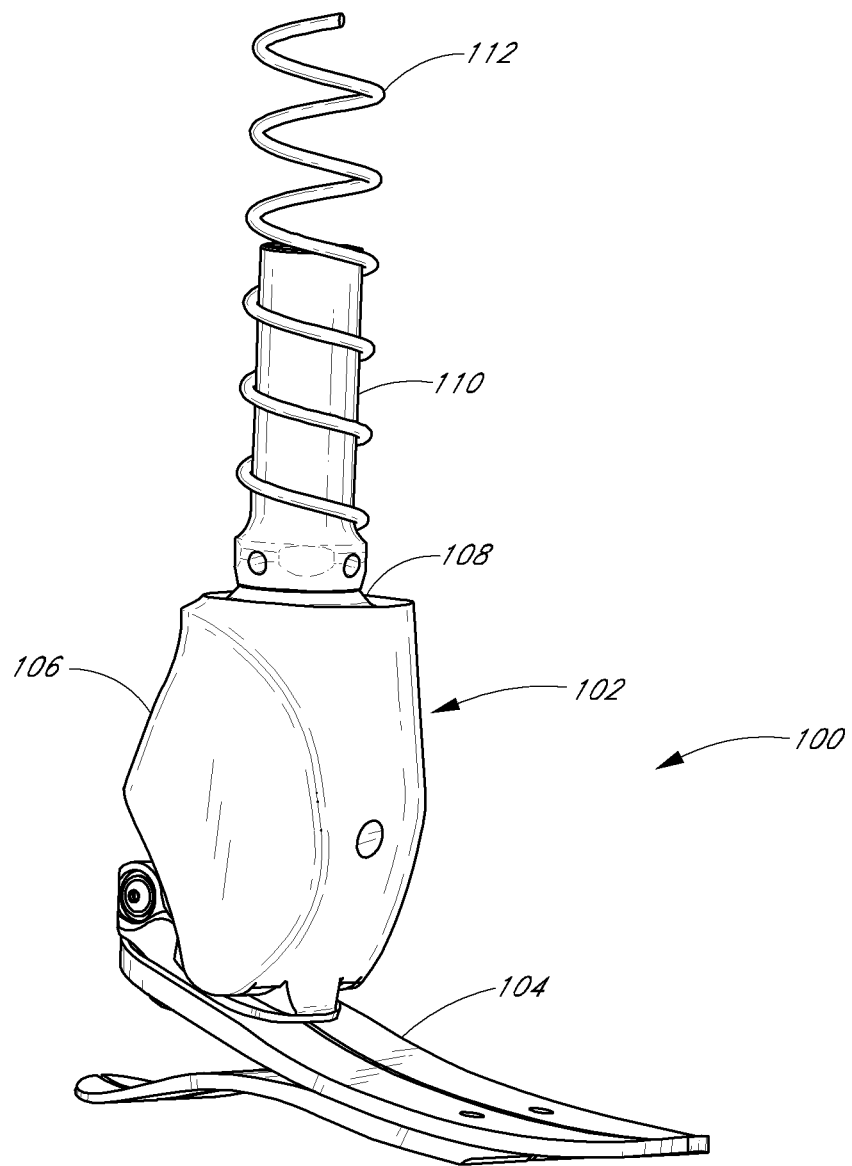
FIG. 1 is a perspective view of a lower limb prosthesis having an ankle-motion-controlled foot unit according to one embodiment of the invention.

Some preferred embodiments of the invention described herein relate generally to prosthetic and orthotic systems and, in particular, to operatively coupled prosthetic and orthotic devices, such as a prosthetic ankle and/or knee, that improve the function of the other prosthetic and/or orthotic devices. While the description sets forth various embodiment-specific details, it will be appreciated that the description is illustrative only and should not be construed in any way as limiting the invention. Furthermore, various applications of the invention, and modifications thereto, which may occur to those who are skilled in the art, are also encompassed by the general concepts described herein. The following U.S. patent applications are hereby incorporated herewith: U.S. App. No. 60/544,259, LOWER LIMB PROSTHESIS WITH ANKLE-MOTION CONTROLLED FOOT, filed Feb. 12, 2004; U.S. App. No. 60/588,232, PROSTHETIC OR ORTHOTIC SYSTEM WITH ANKLE- MOTION-CONTROLLED FOOT, filed Jul. 15, 2004; U.S. application Ser. No. 11/056,344, SYSTEM AND METHOD FOR MOTION-CONTROLLED FOOT UNIT, filed Feb. 11, 2005; U.S. application Ser. No. 11/057,391, SYSTEM AND METHOD FOR MOTION-CONTROLLED FOOT UNIT, filed Feb. 11, 2005; U.S. application Ser. No. 11/367,049, SYSTEMS AND METHODS FOR ACTUATING A PROSTHETIC ANKLE BASED ON A RELAXED POSITION, filed Mar. 1, 2006; U.S. application Ser. No. 11,367,048, SYSTEMS AND METHODS FOR ADJUSTING THE ANGLE OF A PROSTHETIC ANKLE BASED ON A MEASURED SURFACE ANGLE, filed Mar. 1, 2006; U.S. app. No. 60/653,717, SYSTEM AND METHOD OF SYNCHRONIZING AND COMMUNICATING WITH MECHATRONIC DEVICES, filed Feb. 16, 2005; U.S. application Ser. No. 11/355,047, SYSTEM AND METHOD OF SYNCHRONIZING MECHATRONIC DEVICES, filed Feb. 15, 2006; U.S. App. No. 60/679,953, SYSTEM AND METHOD FOR DATA COMMUNICATION WITH A MECHATRONIC DEVICE, filed May 10, 2005; and U.S. application Ser. No. 11/355,058, SYSTEM AND METHOD FOR DATA COMMUNICATION WITH A MECHATRONIC DEVICE, filed Feb. 15, 2006.

The features of the systems and methods will now be described with reference to the drawings summarized above. Throughout the drawings, reference numbers are re-used to indicate correspondence between referenced elements. The drawings, associated descriptions, and specific implementation are provided to illustrate embodiments of the invention and not to limit the scope of the invention.

The terms "prosthetic" and "prosthesis" as used herein are broad terms and are used in their ordinary sense and refer to, without limitation, any system, device or apparatus usable as an artificial substitute or support for a body part.

The term "orthotic" and "orthosis" as used herein are broad terms and are used in their ordinary sense and refer to, without limitation, any system, device or apparatus usable to support, align, prevent, protect, correct deformities of, immobilize, or improve the function of parts of the body, such as joints and/or limbs.

The term "ankle device" as used herein is a broad term and is used in its ordinary sense and relates to any prosthetic, orthotic or ankle-assisting device.

The term "transtibial" as used herein is a broad term and is used in its ordinary sense and relates to without limitation any plane, direction, location, or cross-section that is located at or below a knee joint of a body, including artificial knee joints.

The term "transfemoral" as used herein is a broad term and is used in its ordinary sense and relates to without limitation any plane, direction, location, or cross-section that is located at or above a knee joint of a body, including artificial knee joints.

The term "sagittal" as used herein is a broad term and is used in its ordinary sense and relates to any description, location, or direction relating to, situated in, or being in or near the median plane (i.e., the plane divides the body lengthwise into right and left halves) of the body or any plane parallel or approximately parallel thereto. A "sagittal plane" may also refer to any vertical anterior to posterior plane that passes through the body parallel or approximately parallel to the median plane and that divides the body into equal or unequal right and left sections.

The term "coronal" as used herein is a broad term and is used in its ordinary sense and relates to any description, location, or direction relating to, situated in, or being in or near the plane that passes through the long axis of the body.

A "coronal plane" may also refer to any plane that passes vertically or approximately vertically through the body and is perpendicular or approximately perpendicular to the median plane and that divides the body into anterior and posterior sections.

The term "mechatronic" as used herein is a broad term and is used in its ordinary sense and refer to, without limitation, any system, device, or apparatus that includes an electronically controlled device associated with a limb, including a prosthetic or orthotic device. Such devices may include one or more of a sensor, an actuator, or processor.

The term "bionic" as used herein is a broad term and is used in its ordinary sense and refer to, without limitation, any system, device, or apparatus that includes an electronically controlled device integrated to replace or enhance anatomical structures or physiological processes. Bionic may also include electronic or mechanical smart structures or systems integrated to replace or enhance anatomical structures or physiological processes. For example, a bionic may include a mechatronic device such as prosthetic or orthotic.

FIG. 1 illustrates one embodiment of a lower limb prosthesis 100 having an ankle-motion-controlled foot with an attachment member. The prosthesis 100 comprises an attachment member, in the form of a lower limb member 102, operatively coupled to a foot unit 104. As used herein, the term "attachment member" is a broad term and is used in its ordinary sense and in a prosthetic foot embodiment relates to, without limitation, any member that attaches either directly or indirectly to the foot unit 104 and is moveable in relation thereto, for example by a pivoting motion, and is used to attach the prosthesis 100 to a stump or intermediate prosthesis. As illustrated, the attachment member may take the form of a lower limb member in an ankle-prosthesis embodiment. In other embodiments, for example an orthotic embodiment, the attachment member may be used to attach to and support a body part, such as with a brace, which also is moveably connected to a second member, such as a foot unit, which would also attach to and support a body part, such as the foot. In one embodiment, the lower limb member 102 is a generally elongated member with a main longitudinal axis that extends in approximately a tibial direction, that is, a direction that extends generally along the axis of a natural tibia bone. For example, FIG. 1 depicts the lower limb member 102 as being a generally vertical orientation.

In another embodiment, the lower limb member 102 may comprise multiple sections. For example, the lower limb member 102 may comprise two elongated sections that extend approximately parallel in a tibial direction and that are connected together. In another embodiment, the lower limb member 102 comprises a two-sided chamber having two substantially symmetrical parts to form a partially enclosed housing. In another embodiment, the lower limb member 102 may comprise a hollow member, such as a tube-like structure. In other embodiments, the lower limb member 102 may comprise elongated flat portions or rounded portions. In yet other embodiments, the structure of the lower limb member 102 is not elongated. For example, the lower limb member 102 may comprise a generally circular, cylindrical, half-circular, dome-shaped, oval or rectangular structure. One example of a possible lower limb member is the ankle module and the structures described in U.S. patent application Ser. No. 10/742,455, filed Dec. 18, 2003, and entitled "PROSTHETIC FOOT WITH ROCKER MEMBER," the entirety of which is hereby incorporated herein by reference and is to be considered as part of this specification.

In one embodiment, the lower limb member 102 is generally formed of a machine metal, such as aluminum, or a carbon fiber material. In other embodiments of the invention, the lower limb member 102 may comprise other materials that are suitable for prosthetic devices. In one embodiment, the lower limb member 102 advantageously has a height between approximately 12 and 15 centimeters. In other embodiments of the invention, the lower limb member 102 may have a height less than 12 centimeters or height greater than 15 centimeters depending on the size of the user and/or the intended use of the prosthesis 100. For example, the lower limb member 102 may have a height of approximately 20 centimeters.

In one embodiment, the prosthesis 100 is configured such that the main longitudinal axis of the lower limb member 102 is substantially perpendicular to a lower surface of the foot unit 104 when the prosthesis 100 is in a resting position. In another embodiment, the lower limb member 102 may be substantially perpendicular to a level ground surface when the foot unit 104 rests on the ground. Such a configuration advantageously provides a user with increased support and/or stability.

As depicted in FIG. 1, the lower limb member 102 further comprises a cover 106. The cover 106 houses and/or protects the inner components of the lower limb member 102. In another embodiment, the cover 106 may be rounded or may be shaped in the form of a natural human leg.

The lower limb member 102 further comprises an attachment portion 108 to facilitate coupling of the lower limb member 102. For example, as depicted in FIG. 1, the attachment portion 108 of the lower limb member 102 couples the prosthesis 100 to a pylon 110. In other embodiments of the invention, the attachment portion 108 may be configured to couple the prosthesis 100 to a stump of an amputee or to another prosthetic device. FIG. 1 also depicts a control wire 112 usable to provide power to and/or communicate control signals to the prosthesis 100.

The foot unit 104 may comprise various types of prosthetic or orthotic feet. As illustrated in FIG. 1, the foot unit 104 incorporates a design described in Applicant's co-pending U.S. patent application Ser. No. 10/642,125, entitled "LOW PROFILE PROSTHETIC FOOT," and filed Aug. 15, 2003 the entirety of which is hereby incorporated by reference and is to be considered as part of this specification. For example, the foot unit 104 may comprise a standard LP VARI-FLEX® unit available from Össur.

In one embodiment, the foot unit 104 is configured to exert a proportional response to weight or impact levels on the foot unit 104. In addition, the foot unit 104 may comprise shock absorption for comfortable loading of the heel and/or for returning expended energy. The foot unit 104 may comprise a full-length toe lever with enhanced flexibility so as to provide a stride length for the prosthetic limb that mimics the stride length of the healthy limb. In addition, as depicted in FIG. 1, the foot unit 104 may comprise a split-toe configuration, which facilitates movement on uneven terrain. The foot unit 104 may also include a cosmesis or a foot cover such as, for example, a standard Flex-Foot cover available from Össur.

Figure 2:
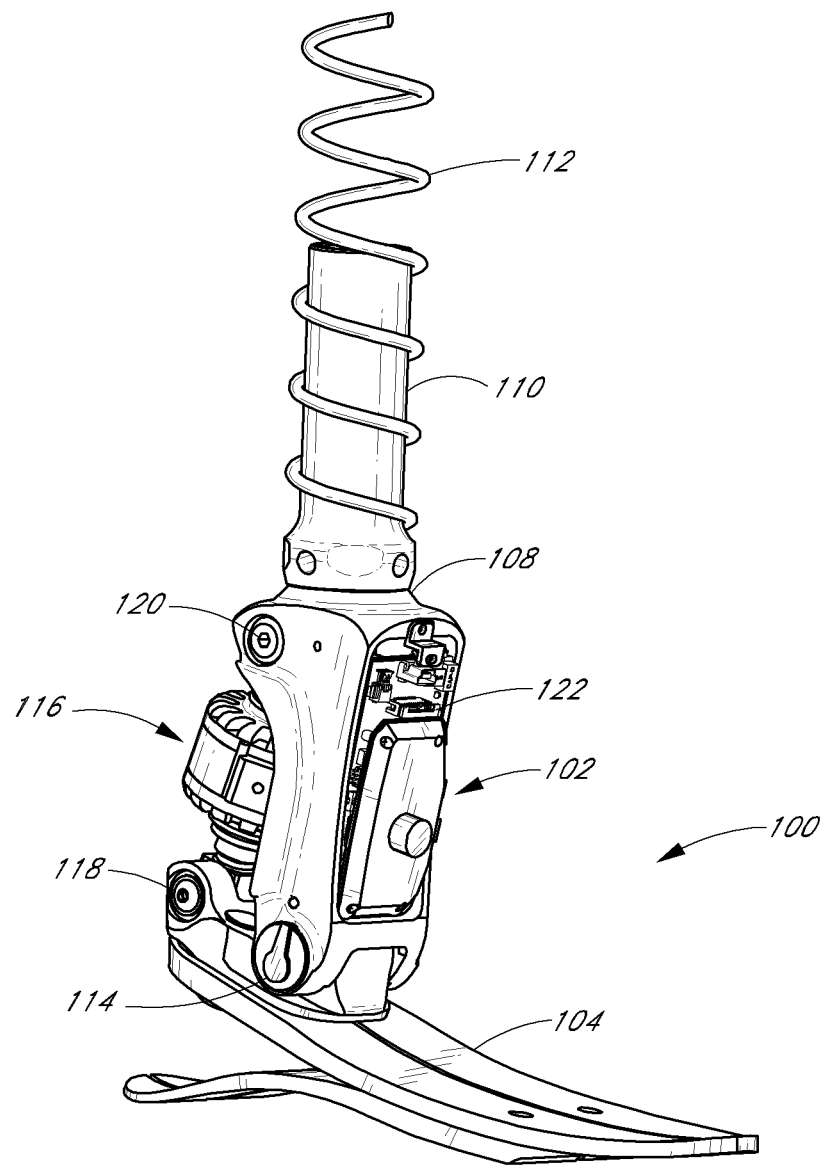
FIG. 2 is a perspective view of the lower limb prosthesis of FIG. 1, wherein a cover is removed to show inner components of the prosthesis.

FIG. 2 depicts the prosthesis 100 with the cover 106 removed. As shown, a lower end of the lower limb member 102 is coupled to the foot unit 104 at a pivot assembly 114. As illustrated, the lower limb member 102 is coupled to an ankle plate of the foot unit 104, which extends generally rearward and upward from a toe portion of the foot unit 104. The pivot assembly 114 allows for angular movement of the foot unit 104 with respect to the lower limb member 102. For example, in one embodiment, the pivot assembly 114 advantageously comprises at least one pivot pin. In other embodiments, the pivot assembly 114 comprises a hinge, a multi-axial configuration, a polycentric configuration, combinations of the same or the like. Preferably, the pivot assembly 114 is located on a portion of the foot unit 104 that is near a natural ankle location of the foot unit 104. In other embodiments of the invention, the pivot assembly 114 may be bolted or otherwise releasably connected to the foot unit 104.

FIG. 2 further depicts the prosthesis 100 having an actuator 116. In one embodiment, the actuator 116 advantageously provides the prosthesis 100 with the necessary energy to execute angular displacements synchronized with the amputee's locomotion. For example, the actuator 116 may cause the foot unit 104 to move similar to a natural human foot. In one embodiment, the lower end of the actuator 116 is coupled to the foot unit 104 at a first attachment point 118. As illustrated, the foot attachment point 118 is advantageously located on the upper surface of the foot unit 104 on a posterior portion thereof. The upper end of the actuator 116 is coupled to the lower limb member 102 at a second attachment point 120.

In one embodiment, the linear motion (or extension and contraction) of the actuator 116 controls, or actively adjusts, the angle between the foot unit 104 and the lower limb member 102. FIG. 2 depicts the actuator 116 comprising a double-screw motor, wherein the motor pushes or pulls a posterior portion of the foot unit 104 with respect to the lower limb member 102. In other embodiments, the actuator 116 comprises other mechanisms capable of actively adjusting an angle, or providing for motion between, multiple members. For example, the actuator 116 may comprise a single-screw motor, a piston cylinder-type structure, a servomotor, a stepper motor, a rotary motor, a spring, a fluid actuator, or the like. In yet other embodiments, the actuator 116 may actively adjust in only one direction, the angle between the lower limb member 102 and the foot unit 104. In such an embodiment, the weight of the user may also be used in controlling the angle caused by and/or the movement of the actuator 116.

FIG. 2 illustrates the actuator 116 in a posterior configuration, wherein the actuator 116 is located behind the lower limb member 102. In other embodiments, the actuator 116 may be used in an anterior configuration, wherein the actuator 116 is located in front of the lower limb member 102. In another embodiment of the invention, the actuator 116 comprises an auto adjusting ankle structure and incorporates a design, such as described in U.S. Pat. No. 5,957,981, the entirety of which is hereby incorporated by reference and is to be considered as a part of this specification. The particular configuration or structure may be selected to most closely imitate the movement and location of a natural human ankle joint and to facilitate insertion of the prosthesis 100 into an outer cosmesis.

Furthermore, the actuator 116 is advantageously configured to operate so as to not to emit loud noises, such as intermittent noises, perceptible by the user and/or others. The actuator 116 may also be configured to not operate or adjust if the prosthesis 100 experiences torque, such as in the sagittal plane, that exceeds a certain level. For example, if the torque level exceeds four Newton meters (Nm), the actuator 116 may cease to operate or may issue an alarm.

The actuator 116 may also be substantially enclosed within the cover 106 as shown in FIG. 1 such that the portions of the actuator 116 are not visible and/or exposed to the environment. In another embodiment, the actuator may be at least partially enclosed by the lower limb member 102.

FIG. 2 further depicts control circuitry 122 usable to control the operation of the actuator 116 and/or the foot unit 104. In one embodiment, the control circuitry 122 comprises at least one printed circuit board (PCB). The PCB may further comprise a microprocessor. Software may also reside on the PCB so as to perform signal processing and/or control the movement of the prosthesis 100.

In one embodiment, the prosthesis 100 includes a battery (not shown) that powers the control circuitry 122 and/or the actuator 116. In one embodiment, the battery comprises a rechargeable lithium ion battery that preferably has a power cycle of at least 12 to 16 hours. In yet other embodiments, the power cycle of the battery may be less than 12 hours or may be more than 16 hours. In other embodiments of the invention, the battery comprises a lithium polymer battery, fuel cell technology, or other types of batteries or technology usable to provide power to the prosthesis 100. In yet other embodiments, the battery is removably attached to a rear surface of the lower limb member 102, to other portions of the prosthesis 100, or is located remote the prosthesis 100. In further embodiments, the prosthesis 100 may be connected to an external power source, such as through a wall adapter or car adapter, to recharge the battery.

In one embodiment, the prosthesis 100 is configured to lock in a neutral position, such as the lower limb member 102 being aligned generally vertical relative to a level ground surface when the foot unit 104 is resting on the level ground surface, when the battery is out of power or enters a low power stage. Such locking provides for operational safety, reliability, and/or stability for a user. The prosthesis 100 may also provide a battery status display that alerts the user as to the status (i.e., charge) of the battery. In another embodiment, the prosthesis 100 locks into a substantially neutral position when the motion control functions of the prosthesis 100 are turned off or disabled by a user.

As discussed above, a cosmesis material or other dressings may be used with the prosthesis 100 so as to give the prosthesis 100 a more natural look or shape. In addition, the cosmesis, dressings, or other filler material may be used to prevent contaminants, such as dirt or water, from contacting the components of the prosthesis 100.

Figure 3:
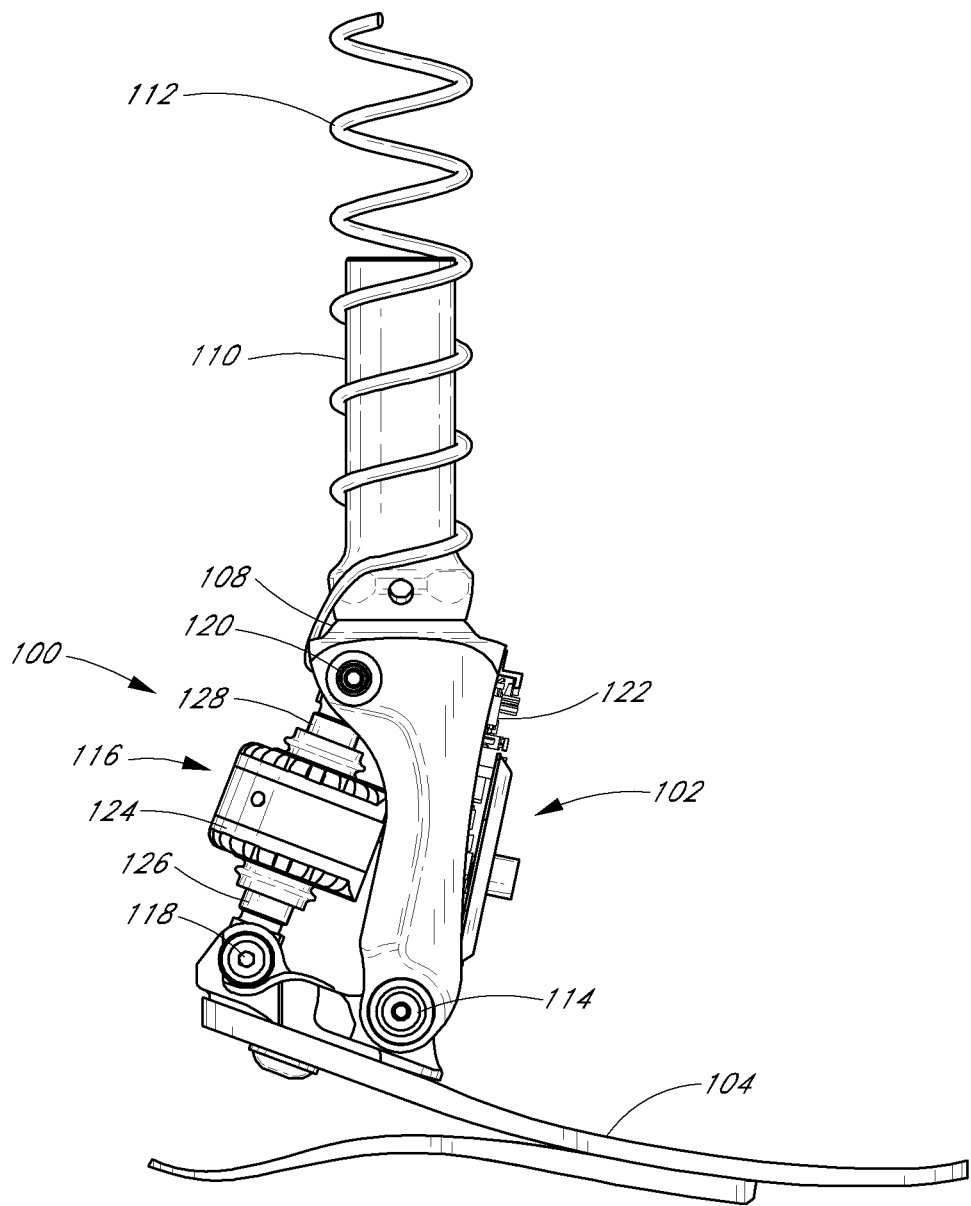
FIG. 3 is a side view of the lower limb prosthesis of FIG. 2.

FIG. 3 depicts a side view of the prosthesis 100 according to one embodiment of the invention. As depicted in FIG. 3, the actuator 116 further comprises a main housing 124, a lower extendable portion 126, and an upper extendable portion 128. The lower extendable portion 126 couples the main housing 124 of the actuator 116 to the foot unit 104 at the first attachment point 118. The upper extendable portion 128 couples the main housing 124 of the actuator 116 to the lower limb member 102 at the second attachment point 120. During operation and active adjustment of the prosthesis 100, the lower extendable portion 126 and/or the upper extendable portion 128 move into and/or out of the main housing 124 of the actuator 116 to adjust an angle between the foot unit 104 and the lower limb member 102.

For example, to increase an angle between the foot unit 104 and the lower limb member 102, the actuator 116 causes the lower extendable portion 126 and/or the upper extendable portion 128 to contract or withdraw into the main housing 124. For example, at least one of the extendable portions 126, 128 may have a threaded surface such that rotation in one direction (e.g., clockwise) causes the extendable portion to withdraw into the main housing 124 of the actuator. In other embodiments, at least one of the extendable portions 126, 128 comprises multiple telescoping pieces such that, upon contraction, one of the multiple pieces of extendable portion contracts into another of the multiple pieces without withdrawing into the main housing 124. Likewise, to decrease an angle between the foot unit 104 and the lower limb member 102, the lower extendable portion 126 and/or the upper extendable portion 128 may extend from the main housing 124.

In embodiments of the invention having an anterior configuration for the actuator 116, extension of the lower extendable portion 126 and/or the upper extendable portion 128 causes an increase in the angle between the lower limb member 102 and the foot unit 104. Likewise, a contraction of the lower extendable portion 126 and/or the upper extendable portion 128 causes a decrease in the angle between the foot unit 104 and the lower limb member 102.

Figure 4:
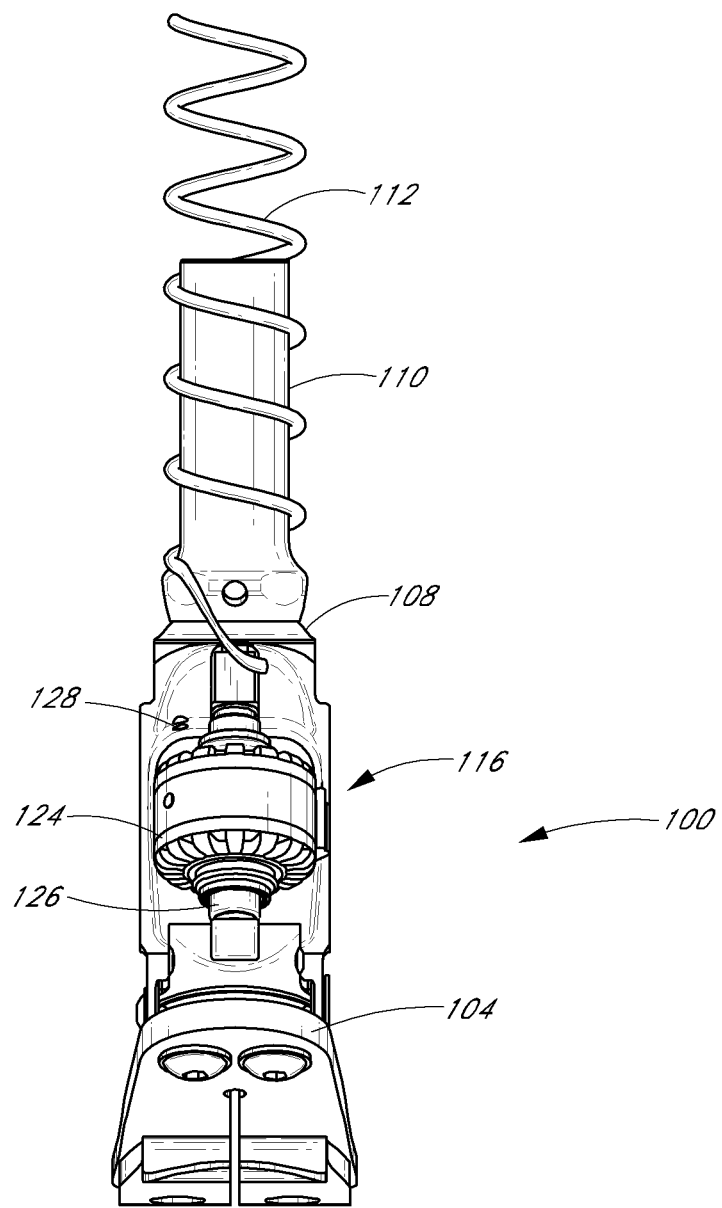
FIG. 4 is a rear view of the lower limb prosthesis of FIG. 2.

FIG. 4 illustrates a rear view of the prosthesis 100 depicted in FIGS. 1-3. In other embodiments of the invention, the cover 106 extends around the posterior portion of the prosthesis 100 to house at least a portion of the actuator 116 such that portions of the actuator 116 are not visible and/or not exposed to the environment.

Figure 5:
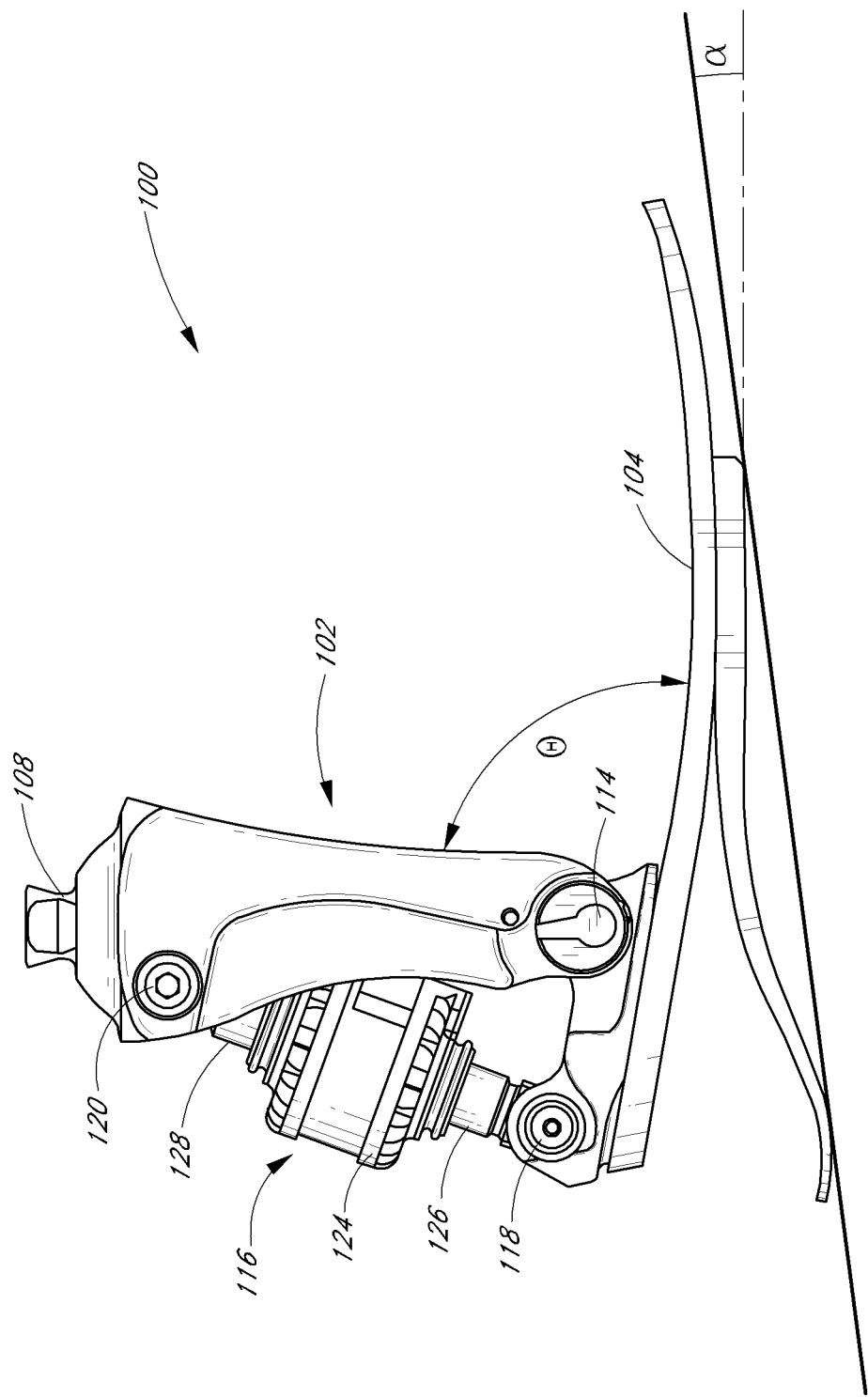
FIG. 5 is a side view of the lower limb prosthesis of FIG. 1 with the cover shown partially removed, wherein the ankle-motion-controlled foot is adjusted to accommodate an incline.
Figure 6:
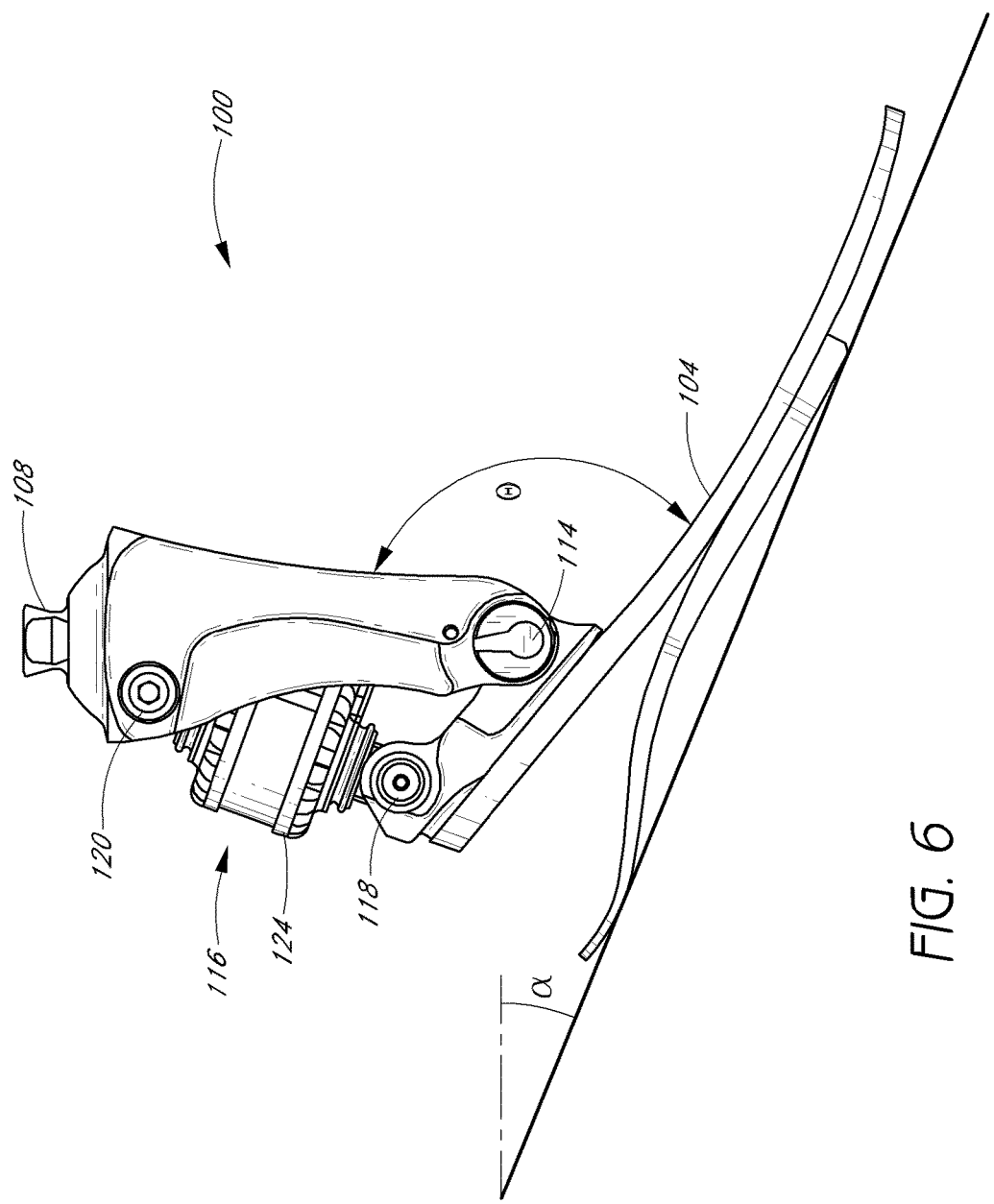
FIG. 6 is a side view of a lower limb prosthesis of FIG. 5, wherein the ankle-motion-controlled foot is adjusted to accommodate a decline.

FIGS. 5 and 6 illustrate one embodiment of the prosthesis 100 as it adjusts to inclines and declines. With reference to FIG. 5, the prosthesis 100 is depicted as adjusting to an incline. In this embodiment, the actuator 116 extends so as to decrease an angle θ between the lower limb member 102 and the foot unit 104 (or "dorsiflexion"). With respect to dorsiflexion, in one embodiment, the angular range of motion of the prosthesis 100 is from about 0 to 10 degrees from the neutral position. Other embodiments may also facilitate exaggerated dorsiflexion during swing phase.

FIG. 6 illustrates the prosthesis 100 as it adjusts to a decline. The actuator 116 extends so as to increase the angle θ between the lower limb member 102 and the foot unit 104 (or "plantarflexion"). With respect to plantarflexion, in one embodiment, the angular range of motion of the prosthesis 100 is from about 0 to 20 degrees from the neutral position. Such plantarflexion mimics natural ankle movement and provides for greater stability to an amputee or a user. In one embodiment, the total range of motion about the ankle pivot axis of the prosthesis 100, including both plantarflexion and dorsiflexion, is approximately 30 degrees or more.

In addition to operating on inclines and declines, the motion-controlled foot of the prosthesis 100 advantageously accommodates different terrain, operates while traveling up and down stairs, and facilitates level ground walking. In addition, the prosthesis 100 may provide for automatic heel height adjustability. Heel height may be measured, in one embodiment, from an ankle portion of the lower limb member 102 to a ground surface when the foot unit 104 is generally flat to the ground. For example, a user may adjust to various heel heights, such as through pressing one or more buttons, such that the prosthesis 100 automatically aligns itself to the appropriate heel height. In one embodiment, the prosthesis 100 includes a plurality of predetermined heel heights. In yet other embodiments, the prosthesis 100 may automatically adjust the heel height without the need for user input.

FIGS. 5 and 6 further illustrate one embodiment of the attachment portion 108. The attachment portion 108 provides alignment between the natural limb of the amputee and the prosthesis 100 and may be configured so as to decrease pressure peaks and shear forces. For example, the attachment portion 108 may be configured to attach to another prosthesis, to the stump of the amputee, or to another component. In one embodiment, the attachment portion 108 comprises a socket connector. The socket connector may be configured to receive a 32 mm-thread component, a male pyramid type coupler, or other components. In other embodiments, the attachment portion 108 may also comprise, or be configured to receive, a female pyramid adapter.

Figure 7:
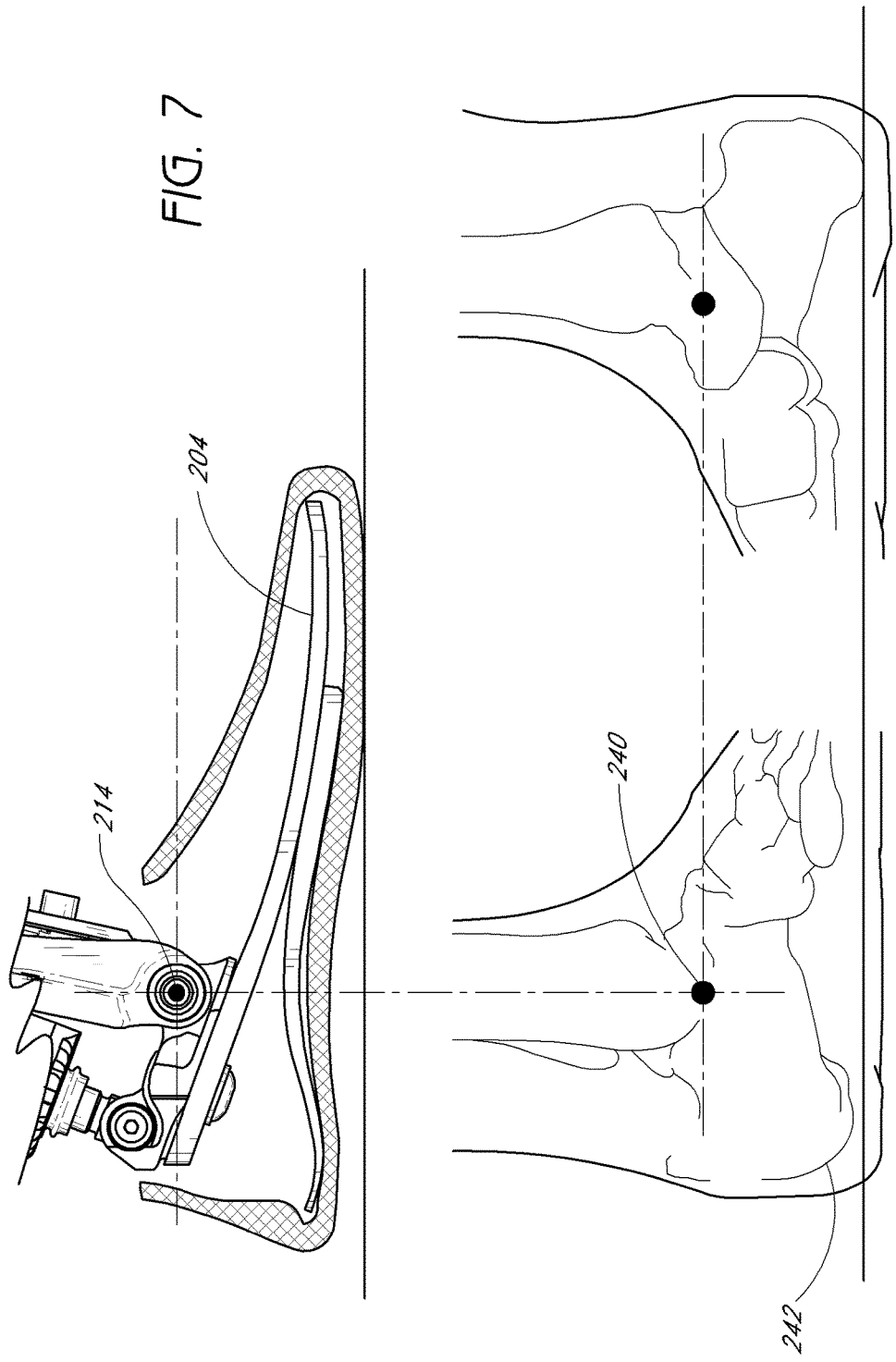
FIG. 7 is a schematic drawing indicating the correlation between an ankle pivot point on an exemplifying embodiment of a prosthetic foot unit with the natural ankle joint of a human foot.

As depicted in FIGS. 5 and 6, the pivot assembly 114 is positioned to mimic a normal human ankle axis. FIG. 7 further illustrates a schematic drawing indicating the correlation between an ankle pivot point on a prosthetic foot unit 204 with the natural human ankle joint of a foot. In particular, the prosthetic foot unit 204 comprises a pivot assembly 214 that corresponds to an ankle joint 240 of a human foot 242. For example, in one embodiment of the invention, the pivot assembly 114 is located near the mechanical ankle center of rotation of the prosthesis 100.

Figure 8:
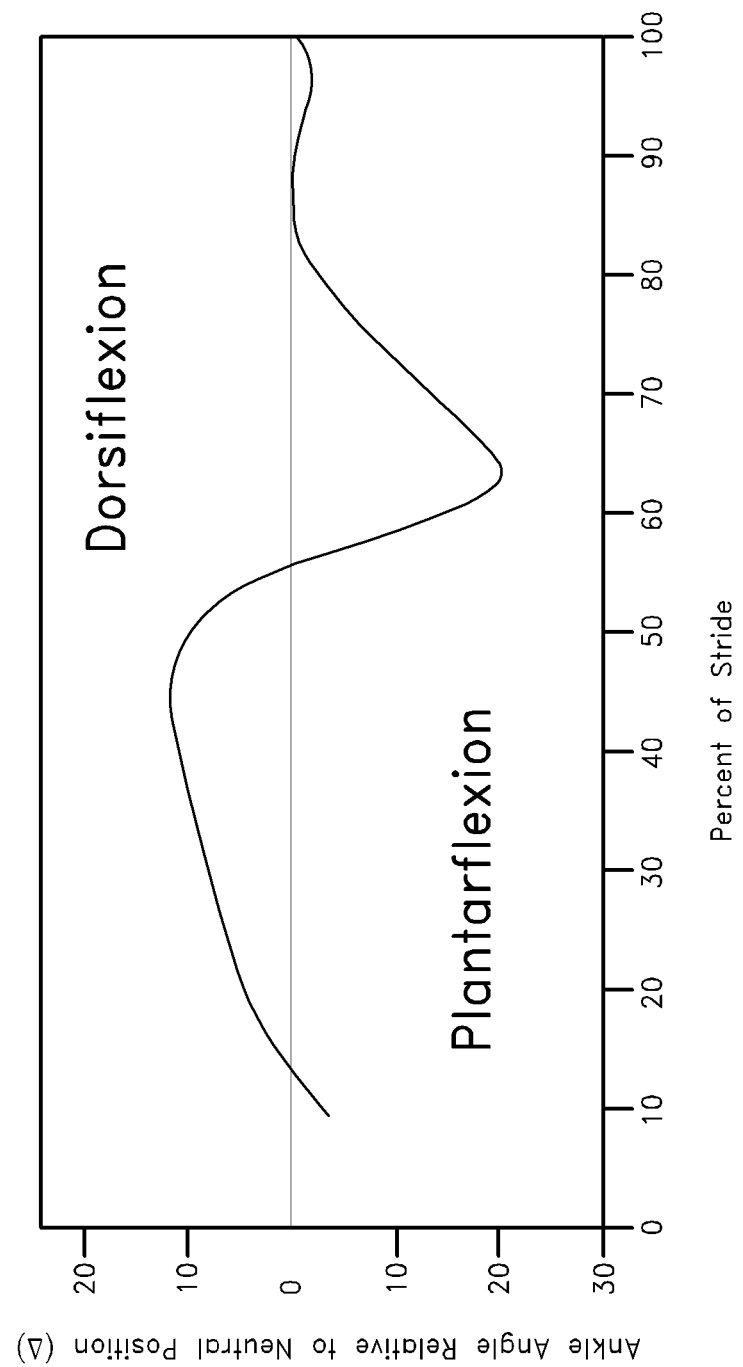
FIG. 8 is a graph depicting the range of ankle motion of an exemplifying embodiment of a prosthetic or orthotic system during one full stride on a level surface.

FIG. 8 illustrates a graph depicting the possible range of ankle motion of an embodiment of the prosthesis 100 during one full stride on a level surface. As shown, the x-axis of the graph represents various points during one full stride of a user (i.e., 0 to 100 percent). The y-axis represents the ankle angle (A) of the prosthesis 100 relative to the ankle angle when the prosthesis 100 is in a neutral position. During one full stride, the ankle angle (Δ) varies from approximately 20 degrees plantarflexion (i.e., neutral position angle +20 degrees) to approximately 10 degrees dorsiflexion (i.e., neutral position angle −10 degrees).

In embodiments as described above, no dampening is provided when adjusting the angular range of motion. In another embodiment of the invention, the prosthesis 100 is configured to provide dampening or passive, soft resistance to changes in the angle between the lower limb member 102 and the foot unit 104. An example of a system for controlling such dampening is disclosed in U.S. Pat. No. 6,443,993, which is hereby incorporated herein by reference and is to be considered as a part of this specification.

For example, when the user is in a standing position, the actuator 116 may provide for increased resistance, or dampening, so as to provide stability to the user. In one embodiment of the invention, dampening of the prosthesis 100 may be provided by hydraulic dampers. In other embodiments of the invention, other components or devices that are known in the art may be used to provide dampening for the prosthesis 100. In addition, in one embodiment of the invention, the dampers may be dynamically controlled, such as through an electronic control system, which is discussed in more detail below. In yet other embodiments, the dampers may be controlled through mechanical and/or fluid-type structures.

It is also recognized that, although the above description has been directed generally to prosthetic systems and devices, the description may also apply to an embodiment of the invention having an orthotic system or device. For example, in one embodiment of the invention, an orthotic system may comprise at least one actuator that actively controls the angle of an orthosis that is used with an injured or debilitated ankle. In addition, the orthotic system may, in addition to the electronic control of the orthotic system, provide for the user's control or natural movement of the injured ankle or leg.

In addition, the above-described systems may be implemented in prosthetic or orthotic systems other than transtibial, or below-the-knee, systems. For example, in one embodiment of the invention, the prosthetic or orthotic system may be used in a transfemoral, or above-the-knee, system, such as is disclosed in U.S. Provisional Application No. 60/569,512, filed May 7, 2004, and entitled "MAGNETORHEOLOGICALLY ACTUATED PROSTHETIC KNEE;" U.S. Provisional Application No. 60/624,986, filed Nov. 3, 2004, and entitled "MAGNETORHEOLOGICALLY ACTUATED PROSTHETIC KNEE;" and U.S. patent application Ser. No. 11/123,870, filed May 6, 2005, and entitled "MAGNETORHEOLOGICALLY ACTUATED PROSTHETIC KNEE;" each of which is hereby incorporated herein by reference in its entirety and is to be considered as part of this specification. For example, the prosthetic or orthotic system may include both a prosthetic or orthotic ankle and/or a prosthetic or orthotic knee.

Figure 9:
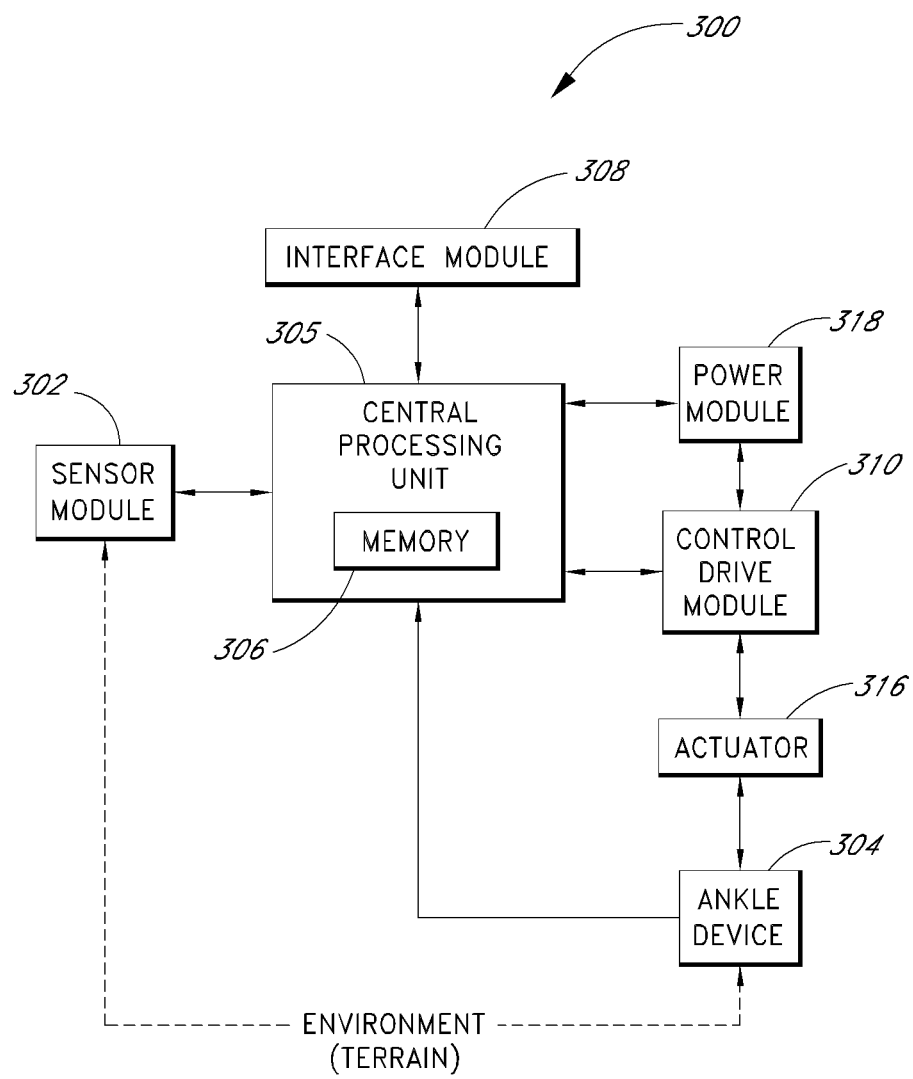
FIG. 9 is a block diagram of an exemplifying embodiment of a control system architecture of a prosthetic or orthotic system having an ankle-motion-controlled foot.

FIG. 9 illustrates a block diagram of one embodiment of a system architecture of a control system 300 for an ankle-motion-controlled foot. In one embodiment of the invention, the control system 300 is usable by the lower limb prosthesis 100 depicted in FIGS. 1-6. In other embodiments of the invention the control system 300 is usable by an orthotic system or a rehabilitation system having an ankle-motion-controlled foot, or other motion-controlled limb. In one embodiment, the control system 300 is based on a distributed processing system wherein the different functions performed by the prosthetic or orthotic system, such as sensing, data processing, and actuation, are performed or controlled by multiple processors that communicate with each other. With reference to FIG. 9, the control system 300 includes a sensor module 302, an ankle device 304 (such as, for example, the prosthesis 100 depicted in FIG. 1), a central processing unit ("CPU") 305, a memory 306, an interface module 308, a control drive module 310, an actuator 316 and a power module 318.

In one embodiment, the control system 300 depicted in FIG. 9 processes data received from the sensing module 302 with the CPU 305. The CPU 305 communicates with the control drive module 310 to control the operation of the actuator 316 so as to mimic natural ankle movement by the ankle device 304. Furthermore, the control system 300 may predict how the ankle device 304 may need to be adjusted in order to accommodate movement by the user. The CPU 305 may also receive commands from a user and/or other device through the interface module 308. The power module 318 provides power to the other components of the control system 300. Each of these components is described in more detail below.

In one embodiment, the sensor module 302 is used to measure variables relating to the ankle device 304, such as the position and/or the movement of the ankle device 304 throughout a gait cycle. In such an embodiment the sensor module 320 is advantageously located on the ankle device 304. For example, the sensor module 302 may be located near a mechanical ankle center of rotation of the ankle device 304, such as the pivot assembly 114 of the prosthesis 100 depicted in FIG. 2. In another embodiment, the sensor module 302 may be located on the user's natural limb that is attached to, or associated with, the ankle device 304. In such an embodiment, the sensors are used to capture information relating to the movement of the natural limb on the user's ankle-device side to adjust the ankle device 304.

In one embodiment, the sensor module 302 advantageously includes a printed circuit board housing, multiple sensors, such as accelerometers, which each measures an acceleration of the ankle device 304 in a different axis. For example, the sensor module 302 may comprise three accelerometers that measure acceleration of the ankle device 304 in three substantially, mutually perpendicular axes. Sensors of the type suitable for the sensor module 302 are available from, for example, Dynastream Innovations, Inc. (Alberta, Canada).

In other embodiments, the sensor module 302 may include one or more other types of sensors in combination with, or in place of, accelerometers. For example, the sensor module 302 may include a gyroscope configured to measure the angular speed of body segments and/or the ankle device 304. In other embodiments, the sensor module 302 includes a plantar pressure sensor configured to measure, for example, the vertical plantar pressure of a specific underfoot area. In yet other embodiments, the sensor module 302 may include one or more of the following: kinematic sensors, single-axis gyroscopes, single- or multi-axis accelerometers, load sensors, flex sensors or myoelectric sensors that may be configured to capture data from the user's natural limb. U.S. Pat. Nos. 5,955,667, 6,301,964, and 6,513,381, also illustrate examples of sensors that may be used with embodiments of the invention, which patents are herein incorporated by reference in their entireties and are to be considered as part of this specification.

Furthermore, the sensor module 302 may be used to capture information relating to, for example, one or more of the following: the position of the ankle device 304 with respect to the ground; the inclination angle of the ankle device 304; the direction of gravity with respect to the position of the ankle device 304; information that relates to a stride of the user, such as when the ankle device 304 contacts the ground (e.g., "heel strike"), is in mid-stride, or leaves the ground (e.g., "toe-off"), the distance from the ground of the prosthesis 100 at the peak of the swing phase (i.e., a particular height during the swing phase); the timing of the peak of the swing phase; and the like.

In yet other embodiments, the sensor module 302 is configured to detect gait patterns and/or events. For example, the sensor module 302 may determine whether the user is in a standing/stopped position, is walking on level ground, is ascending and/or descending stairs or sloped surfaces, or the like. In other embodiments, the sensor module 302 is configured to detect or measure the heel height of the ankle device 304 and/or determine a static shank angle in order to detect when the user is in a sitting position.

As depicted in FIG. 9, in one embodiment of the invention, the sensor module 302 is further configured to measure environmental or terrain variables including one or more of the following: the characteristics of the ground surface, the angle of the ground surface, the air temperature and wind resistance. In one embodiment, the measured temperature may be used to calibrate the gain and/or bias of other sensors.

In other embodiments, the sensor module 302 captures information about the movement and/or position of a user's natural limb, such as a healthy leg. In such an embodiment, it may be preferable that when operating on an incline or a decline, the first step of the user be taken with the healthy leg. Such would allow measurements taken from the natural movement of the healthy leg prior to adjusting the ankle device 304. In one embodiment of the invention, the control system 300 detects the gait of the user and adjusts the ankle device 304 accordingly while the ankle device 304 is in a swing phase of the first step. In other embodiments of the invention, there may be a latency period in which the control system 300 requires one or two strides before being able to accurately determine the gait of the user and to adjust the ankle device 304 appropriately.

In one embodiment of the invention, the sensor module 302 has a default sampling rate of 100 hertz (Hz). In other embodiments, the sampling rate may be higher or lower than 100 Hz or may be adjustable by a user, or may be adjusted automatically by software or parameter settings. In addition, the sensor module 302 may provide for synchronization between types of data being sensed or include time stamping. The sensors may also be configured so as to have an angular resolution of approximately 0.5 degrees, allowing for fine adjustments of the ankle device 304.

In one embodiment, the sensor module 302 is configured to power down into a "sleep" mode when sensing is not needed, such as for example, when the user is relaxing while in a sitting or reclining position. In such an embodiment, the sensor module 302 may awake from the sleep state upon movement of the sensor module 302 or upon input from the user. In one embodiment, the sensor module 302 consumes approximately 30 milliamps (mA) when in an "active" mode and approximately 0.1 mA when in a "sleep" mode.

FIG. 9 illustrates the sensor module 302 communicating with the CPU 305. In one embodiment, the sensor module 302 advantageously provides measurement data to the CPU 305 and/or to other components of the control system 300. In one embodiment, the sensor module 302 is coupled to a transmitter, such as, for example, a Bluetooth® transmitter, that transmits the measurements to the CPU 305. In other embodiments, other types of transmitters or wireless technology may be used, such as infrared, WiFi®, or radio frequency (RF) technology. In other embodiments, wired technologies may be used to communicate with the CPU 305.

In one embodiment, the sensor module 302 sends a data string to the CPU 305 that comprises various types of information. For example, the data string may comprise 160 bits and include the following information:

[TS; AccX; AccY; AccZ; GyroX, GyroY, GyroZ, DegX, DegY, FS, M];

wherein TS=Timestamp; AccX=linear acceleration of foot along X axis; AccY=linear acceleration of foot along Y axis; AccZ=linear acceleration of foot along Z axis; GyroX=angular acceleration of foot along X axis; GyroY=angular acceleration of foot along Y axis; GyroZ=angular acceleration of foot along Z axis; DegX=foot inclination angle in coronal plane; DegY=foot inclination angle in sagittal plane; FS=logic state of switches in the ankle device 304; and M=orientation of the sensors. In other embodiments of the invention, other lengths of data strings comprising more or less information may be used.

The CPU 305 advantageously processes data received from other components of the control system 300. In one embodiment of the invention, the CPU 305 processes information relating to the gait of the user, such as information received from the sensor module 302, determines locomotion type (i.e., gait pattern), and/or sends commands to the control drive module 310. For example, the data captured by the sensor module 302 may be used to generate a waveform that portrays information relating to the gait or movement of the user. Subsequent changes to the waveform may be identified by the CPU 305 to predict future movement of the user and to adjust the ankle device 304 accordingly. In one embodiment of the invention, the CPU 305 may detect gait patterns from as slow as 20 steps per minute to as high as 125 steps per minute. In other embodiments of the invention, the CPU 305 may detect gait patterns that are slower than 20 steps per minute or higher than 125 steps per minute.

In one embodiment of the invention, the CPU 305 processes data relating to state transitions according to the following table (TABLE 1). In particular, TABLE 1 shows possible state transitions usable with the control system 300. The first column of TABLE 1 lists possible initial states of the ankle device 304, and the first row lists possible second states of the ankle device 304. The body of TABLE 1 identifies the source of data used by the CPU 305 in controlling, or actively adjusting, the actuator 316 and the ankle device 304 during the transition from a first state to a second state; wherein "N" indicates that no additional data is needed for the state transition; "L" indicates that the CPU 305 uses transition logic to determine the adjustments to the ankle device 304 during the state transition; and "I" indicates the CPU receives data from an interface (e.g., interface module 308, external user interface, electronic interface or the like). Transition logic usable with embodiments of the invention may be developed by one with ordinary skill in the relevant art. Examples of transition logic used in similar systems and methods to embodiments of the present invention are disclosed in U.S. Provisional Application No. 60/572,996, entitled "CONTROL SYSTEM AND METHOD FOR A PROSTHETIC KNEE," filed May 19, 2004, and U.S. application Ser. No. 11/077,177, entitled "CONTROL SYSTEM AND METHOD FOR A PROSTHETIC KNEE," filed Mar. 9, 2005, each of which is hereby incorporated herein by reference in its entirety and is to be considered as a part of this specification.

304 to move into a particular plantarflexion position to facilitate putting the clothing on over the ankle device 304.

In other embodiments of the invention, other states are usable with the ankle device 304 in place of, or in combination with, the states identified in TABLE 1. For example, states may be defined that correspond to lying down, cycling, climbing a ladder or the like. Furthermore, in controlling the state transitions, the CPU 305 and/or control system 300 may process or derive data from sources other than those listed in TABLE 1.

In other embodiments, the CPU 305 may perform a variety of other functions. For example, the CPU 305 may use information received from the sensor module 302 to detect stumbling by the user. The CPU 305 may function as a manager of communication between the components of the control system 300. For example, the CPU 305 may act as the master device for a communication bus between multiple components of the control system 300. As illustrated, in one embodiment, the CPU 305 communicates with the power module 318. For example, the CPU 305 may provide power distribution and/or conversion to the other components of the control system 300 and may also monitor battery power or battery life. In addition, the CPU 305 may function so as to temporarily suspend or decrease power to the control system 300 when a user is in a sitting or a standing position. Such control provides for energy conservation during peri-

TABLE 1

| TRANSITIONS FROM STATE TO STATE | OFF | HEEL_HEIGHT_CAL | SENSOR_CAL | NEUTRAL | WALK | STAIRS_UP | STAIRS_DOWN | RELAX | PANTS |
|---|---|---|---|---|---|---|---|---|---|
| OFF | N | I | I | I | N | N | N | I | I |
| HEEL_HEIGHT_CAL | L | N | N | L | N | N | N | N | N |
| SENSOR_CAL | L | N | N | L | N | N | N | N | N |
| NEUTRAL | I | I | I | N | L | L | L | L | I |
| WALK | I | N | N | L | N | L | L | N | N |
| STAIRS_UP | I | N | N | L | L | N | L | N | N |
| STAIRS_DOWN | I | N | N | L | L | L | N | N | N |
| RELAX | I | N | N | L | N | N | N | N | I |
| PANTS | I | N | N | I | N | N | N | N | N |

In one embodiment, the above described states in TABLE 1 are predefined states of the ankle device 304. For example, the "OFF" state may indicate that the functions of the ankle device 304 and the actuator 316 are in an off or suspend mode. The "HEEL_HEIGHT_CAL" state relates to the measuring of a heel height from a static sensor angle such as, for example, when the ankle device 304 is not in motion. The "SENSOR_CAL" state relates to surface angle calibration when the user is walking on a level surface. The "NEUTRAL" state relates to when the ankle device 304 is locked in a substantially fixed position. The "WALK" state relates to when the user is walking, such as on a level or sloped surface. "The "STAIRS_UP" and "STAIRS_DOWN" states relate to when the user is walking, respectively, up and down stairs. The "RELAX" state relates to when the user is in a relaxed position. For example, in one embodiment, the "RELAX" state relates to when a user is in a sitting position with the limb having the ankle device 304 crossed over the other limb. In such an embodiment, the control system 300 may cause the ankle device 304 to move into a particular plantarflexion position and/or look of a healthy foot. The "PANTS" state relates to when a user is putting on pants, trousers, shorts or the like. In such a state, the control system 300 may, in one embodiment, cause the ankle device ods of decreased use. The CPU 305 may also process error handling, such as when communication fails between components, an unrecognized signal or waveform is received from the sensor module 302, or when the feedback from the control drive module 310 or the ankle device 304 causes an error or appears corrupt.

In yet other embodiments of the invention, the CPU 305 uses or computes a security factor when analyzing information from the sensor module 302 and/or sending commands to the control drive module 310. For example, the security factor may include a range of values, wherein a higher value indicates a higher degree of certainty associated with a determined locomotion type of the user, and a lower security factor indicates a lower degree of certainty as to the locomotion type of the user. In one embodiment of the invention, adjustments are not made to the ankle device 304 unless the locomotion type of the user is recognized with a security factor above a predetermined threshold value.

In one embodiment, the CPU 305 includes modules that comprise logic embodied in hardware or firmware, or that comprise a collection of software instructions written in a programming language, such as, for example C++. A software module may be compiled and linked into an executable program, installed in a dynamic link library, or may be written in an interpretive language such as BASIC. It will be appreciated that software modules may be callable from other modules or from themselves, and/or may be invoked in response to detected events or interrupts. Software instructions may be embedded in firmware, such as an EPROM or EEPROM. It will be further appreciated that hardware modules may be comprised of connected logic units, such as gates and flip-flops, and/or may be comprised of programmable units, such as programmable gate arrays or processors.

FIG. 9 further depicts CPU 305 including a memory 306 for storing instructions and/or data. For example, the memory 306 may store one or more of the following types of data or instructions: an error log for the other components of the control system 300; information regarding gait patterns or curves; information regarding past activity of the user (e.g., number of steps); control parameters and set points; information regarding software debugging or upgrading; preprogrammed algorithms for basic movements of the prosthetic or orthotic system; calibration values and parameters relating to the sensor module 302 or other components; instructions downloaded from an external device; combinations of the same or the like.

The memory 306 may comprise any buffer, computing device, or system capable of storing computer instructions and/or data for access by another computing device or a computer processor. In one embodiment, the memory 306 is a cache that is part of the CPU 305. In other embodiments of the invention, the memory 306 is separate from the CPU 305. In other embodiments of the invention, the memory 306 comprises random access memory (RAM) or may comprise other integrated and accessible memory devices, such as, for example, read-only memory (ROM), programmable ROM (PROM), and electrically erasable programmable ROM (EEPROM). In another embodiment, the memory 306 comprises a removable memory, such as a memory card, a removable drive, or the like.

In one embodiment, the CPU 305 may also be configured to receive through the interface module 308 user- or activity-specific instructions from a user or from an external device. The CPU 305 may also receive updates to already existing instructions. Furthermore, the CPU 305 may communicate with a personal computer, a personal digital assistant, or the like so as to download or receive operating instructions. Activity-specific instructions may include, for example, data relating to cycling, driving, ascending or descending a ladder, adjustments from walking in snow or sand, or the like.

In one embodiment, the interface module 308 comprises an interface that the user accesses so as to control or manage portions or functions of the prosthetic or orthotic system. In one embodiment, the interface module 308 is a flexible keypad having multiple buttons and/or multiple light emitting diodes (LEDs) usable to receive information from and/or convey information to a user. For example, the LEDs may indicate the status of a battery or may convey a confirmation signal to a user. The interface module 308 may be advantageously located on the ankle device 304. Furthermore, the interface module 308 may comprise a USB connector usable for communication to an external computing device, such as a personal computer.

In a further embodiment, the interface module 308 comprises an on/off switch. In another embodiment, the interface module 308 may receive input regarding the user-controlled heel height or a forced relaxed mode of the prosthetic or orthotic system. In other embodiments, the user may adjust the type of response desired of the prosthesis or enable/disable particular functions of the ankle device 304. The input from the user may be entered directly via the interface module 308, such as through actuating a button, or user input may be received via a remote control.

The interface module 308 may comprise a touch screen, buttons, switches, a vibrator, an alarm, or other input-receiving or output structures or devices that allow a user to send instructions to or receive information from the control system 300. In another embodiment of the invention, the interface module 308 comprises an additional structure, such as a plug, for charging a battery powering the control system 300, such as at home or in a vehicle. In other embodiments of the invention, the interface module 308 may also communicate directly or indirectly with components of the control system 300 other than the CPU 305.

The control drive module 310 is used to translate high-level plans or instructions received from the CPU 305 into low-level control signals to be sent to the actuator 316. In one embodiment, the control drive module 310 comprises a printed circuit board that implements control algorithms and tasks related to the management of the actuator 316. In addition, the control drive module 310 may be used to implement a hardware abstraction layer that translates the decision processes of the CPU 305 to the actual hardware definition of the actuator 316. In another embodiment of the invention, the control drive module 310 may be used to provide feedback to the CPU 305 regarding the position or movement of the actuator 316 or ankle device 304. The control drive module 310 may also be used to adjust the actuator 316 to a new "neutral" setting upon detection by the CPU 305 that the user is traveling on an angled surface.

In one embodiment of the invention, the control drive module 310 is located within the ankle device 304. In other embodiments, the control drive module 310 may be located on the outside of the ankle device 304, such as on a socket, or remote to the ankle device 304.

The actuator 316 provides for the controlled movement of the ankle device 304. In one embodiment, the actuator 316 functions similarly to the actuator 116 described with respect to FIGS. 1-6, which actuator 116 controls the ankle motion of the prosthesis 100. In other embodiments of the invention, the actuator 316 may be configured to control the motion of an orthotic device, such as a brace or other type of support structure.

The ankle device 304 comprises any structural device that is used to mimic the motion of a joint, such as an ankle, and that is controlled, at least in part, by the actuator 316. In particular, the ankle device 304 may comprise a prosthetic device or an orthotic device.

The power module 318 includes one or more sources and/or connectors usable to power the control system 300. In one embodiment, the power module 318 is advantageously portable, and may include, for example, a rechargeable battery, as discussed previously. As illustrated in FIG. 9, the power module 318 communicates with the control drive module 310 and the CPU 305. In other embodiments, the power module 318 communicates with other control system 300 components instead of, or in combination with, the control drive module 310 and the CPU 305. For example, in one embodiment, the power module 318 communicates directly with the sensor module 302. Furthermore, the power module 318 may communicate with the interface module 308 such that a user is capable of directly controlling the power supplied to one or more components of the control system 300.

The components of the control system 300 may communicate with each other through various communication links. FIG. 9 depicts two types of links: primary communication links, which are depicted as solid lines between the components, and secondary communication links, which are depicted as dashed lines. In one embodiment, primary communication links operate on an established protocol. For example, the primary communication links may run between physical components of the control system 300. Secondary communication links, on the other hand, may operate on a different protocol or level than the primary communication links. For example, if a conflict exists between a primary communication link and a secondary communication link, the data from the primary communication link will override the data from the secondary communication link. The secondary communication links are shown in FIG. 9 as being communication channels between the control system 300 and the environment. In other embodiments of the invention, the modules may communicate with each other and/or the environment through other types of communication links or methods. For example, all communication links may operate with the same protocol or on the same level of hierarchy.

It is also contemplated that the components of the control system 300 may be integrated in different forms. For example, the components can be separated into several subcomponents or can be separated into more devices that reside at different locations and that communicate with each other, such as through a wired or wireless network. For example, in one embodiment, the modules may communicate through RS232 or serial peripheral interface (SPI) channels. Multiple components may also be combined into a single component. It is also contemplated that the components described herein may be integrated into a fewer number of modules. One module may also be separated into multiple modules.

Although disclosed with reference to particular embodiments, the control system 300 may include more or fewer components than described above. For example, the control system 300 may further include an actuator potentiometer usable to control, or fine-tune, the position of the actuator 316. The user may also use the actuator potentiometer to adjust the heel height of the ankle device 304. In one embodiment, the actuator potentiometer communicates with the CPU 305. In other embodiments, the control system 300 may include a vibrator, a DC jack, fuses, combinations of the same, or the like.

Examples of similar or other control systems and other related structures and methods are disclosed in U.S. patent application Ser. No. 10/463,495, filed Jun. 17, 2003, entitled "ACTUATED LEG PROSTHESIS FOR ABOVE-KNEE AMPUTEES," now published as U.S. Publication No. 2004/0111163; U.S. patent application Ser. No. 10/600,725, filed Jun. 20, 2003, entitled "CONTROL SYSTEM AND METHOD FOR CONTROLLING AN ACTUATED PROSTHESIS," now published as U.S. Publication No. 2004/0049290; U.S. patent application Ser. No. 10/627,503, filed Jul. 25, 2003, entitled "POSITIONING OF LOWER EXTREMITIES ARTIFICIAL PROPRIOCEPTORS," now published as U.S. Publication No. 2004/0088057; U.S. patent application Ser. No. 10/721,764, filed Nov. 25, 2003, entitled "ACTUATED PROSTHESIS FOR AMPUTEES," now published as U.S. Publication No. 2004/0181289; and U.S. patent application Ser. No. 10/715,989," filed Nov. 18, 2003, entitled "INSTRUMENTED PROSTHETIC FOOT," now published as U.S. Publication No. 2005/0107889; each of which is herein incorporated by reference in its entirety and is to be considered as part of this specification. In addition, other types of control systems that may be used in embodiments of the present invention are disclosed in U.S. Provisional Application No. 60/551,717, entitled "CONTROL SYSTEM FOR PROSTHETIC KNEE," filed Mar. 10, 2004; U.S. Provisional Application No. 60/569,511, entitled "CONTROL SYSTEM AND METHOD FOR A PROSTHETIC KNEE," filed May 7, 2004; and U.S. Provisional Application No. 60/572,996, entitled "CONTROL SYSTEM AND METHOD FOR A PROSTHETIC KNEE," filed May 19, 2004, which are herein incorporated by reference in their entireties to be considered as part as this specification.

FIG. 10 is a table that depicts possible control signals that may be involved in adjusting the ankle angle of a prosthetic or orthotic device when a user is transitioning between different states, or types of locomotion, according to one embodiment of the invention. In particular, the states listed in a column 402 identify a first state of the user, and the states listed in a row 404 identify a second state of the user, or the state to which the user is transitioning. The remainder of the table identifies possible actions that may be taken by the prosthetic or orthotic device with respect to the ankle angle. "User set point" is the neutral, or default, value that may be set during shoe heel height adjustment. The angles specified are examples of changes to the ankle angle of the prosthetic or orthotic device. For example, when a user is transitioning from a "stance" state to an "ascending stairs" state, the ankle angle may be adjusted to the angle of the stairs, such as for example, −10 degrees (or 10 degrees dorsiflexion). Ankle angles given in the "Incline (up)" and "Decline" columns reflect threshold levels of ankle angle adjustment depending on the angle of the incline.

The following table (TABLE 2) illustrates possible ankle motion strategies for one embodiment of the invention. The first column of TABLE 2 lists different types of locomotion types or gait patterns that may be frequently detected. The second column of TABLE 2 identifies examples of ankle angle adjustment of the prosthetic or orthotic device during the swing phase of each of the identified locomotion types.

TABLE 2

| Locomotion Type/Gait Pattern | Ankle Motion During Swing Phase of Ankle Device |
| --- | --- |
| Level Ground Walking | Toe clearance during swing |
| Ascending Stairs | Ankle adjusts to dorsiflexion (e.g., 7.5°) |
| Descending Stairs | Ankle adjusts to dorsiflexion (e.g., 5°) |
| Incline (up) | Ankle adjust to dorsiflexion:<br>a) Two incline angle threshold levels (x°, y°)<br>b) Stepwise (2 steps) angle adjustment (z°, w°)<br>Example: If incline angle > x°, ankle will adjust to −z°; if incline angle > y°, ankle will adjust to −w°, wherein x = 2.5° and y = 5°. |
| Decline | Ankle adjusts to plantarflexion:<br>a) Two decline angle threshold levels (x°, y°)<br>b) Stepwise (2 steps) angle adjustment (z°, w°)<br>Example: If decline angle > x°, ankle will adjust to z°; if decline angle > y°, ankle will adjust to w°, wherein x = 2.5° and y = 5°. |
| Sitting/Relaxed | Set Heel Height |
| Adjust Heel Height | Stepless heel height adjustment up to 20° plantarflexion |

Figure 11:
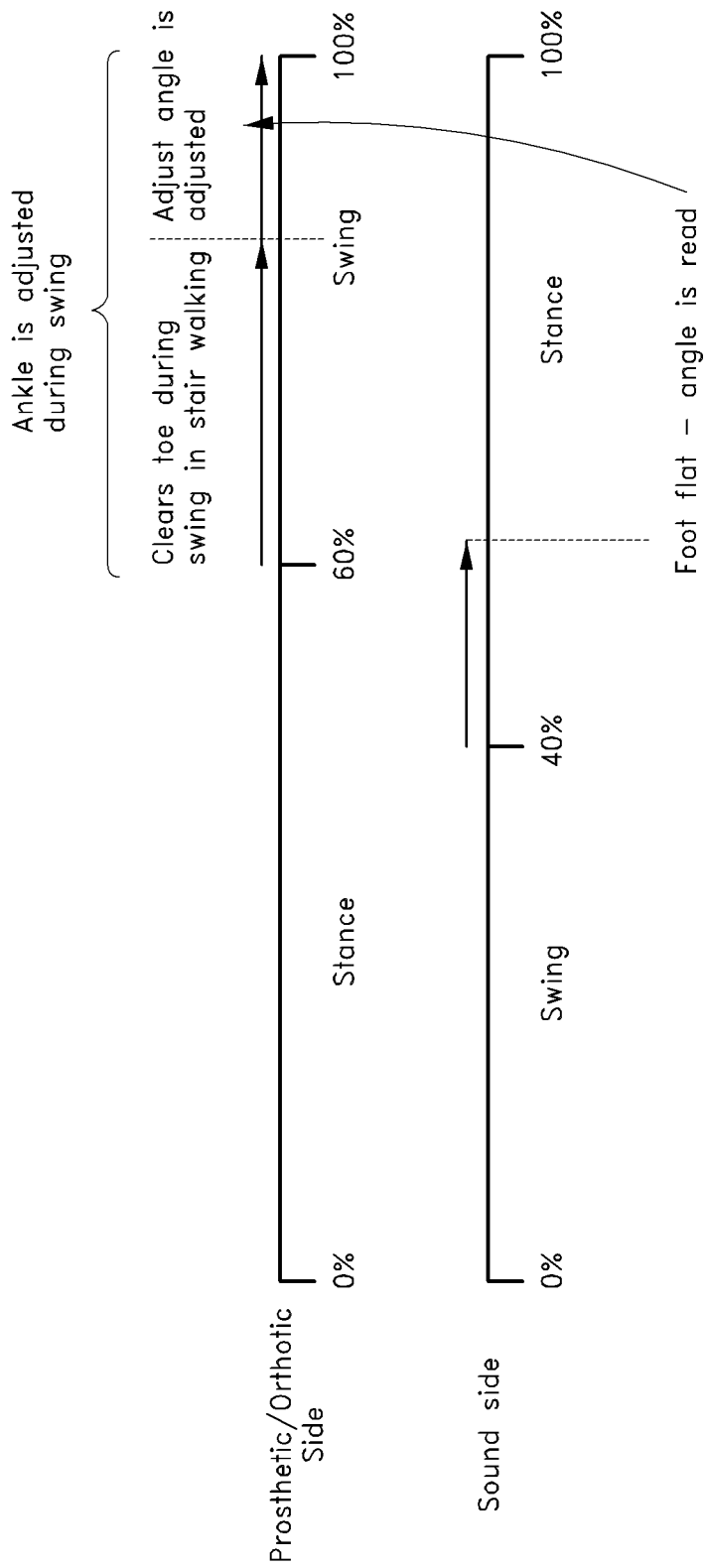
FIG. 11 is a graph depicting an exemplifying embodiment of the relationship between the control of a prosthetic or orthotic system and the motion of a corresponding sound limb.

FIG. 11 depicts a graph that illustrates the interaction and relationship between the control of a prosthetic or orthotic leg and the measurements taken from a healthy, sound leg. In particular, FIG. 11 depicts the movement of a prosthetic or orthotic leg and a healthy leg during one full stride of a user. For example, during approximately the first 60% of the stride, the graph shows the prosthetic or orthotic leg as being in a "stance" position or being planted on a surface, such as the ground. In one embodiment, during the beginning portion of the stance phase the ankle angle of the prosthetic or orthotic leg may decrease (dorsiflexion). Toward the end of the stance phase the ankle angle of the prosthetic or orthotic leg may then increase (plantarflexion) to facilitate natural stride movements. In other embodiments of the invention, the ankle angle of the prosthetic or orthotic leg is not actively adjusted during the stance phase. During a portion of this same period, up to approximately point 40%, the healthy leg may be in a swinging position, wherein the healthy leg is not in contact with the ground. Between the points of approximately 40% and 60%, both legs are in contact with the ground.

From approximately point 60% to 100% (the end of the stride), the prosthetic or orthotic leg is in a swinging position, and the healthy leg is in contact with the ground. The graph in FIG. 11 shows that the ankle angle of the prosthetic or orthotic leg is adjusted during the swing phase. This angle adjustment may be based on previous measurements of the healthy leg during the swing phase of the healthy leg. In one embodiment, during the beginning portion of the swing phase of the prosthetic or orthotic leg, the ankle angle of the prosthetic or orthotic leg may decrease. This allows, for example, a toe portion of the prosthetic or orthotic leg to clear stairs. Toward the latter portion of the swing phase of the prosthetic or orthotic leg, the ankle angle of the prosthetic or orthotic leg may then increase before contacting the ground. In other embodiments, the angle adjustment is based on readings taken by sensors on the prosthetic side.

It is to be understood that FIG. 11 is illustrative of the functioning of one embodiment of the invention under certain conditions. Other embodiments or circumstances may require a longer or shorter stance or swing phase and require other adjustments to the angle of the ankle portion of the prosthetic leg.

Figure 12A:
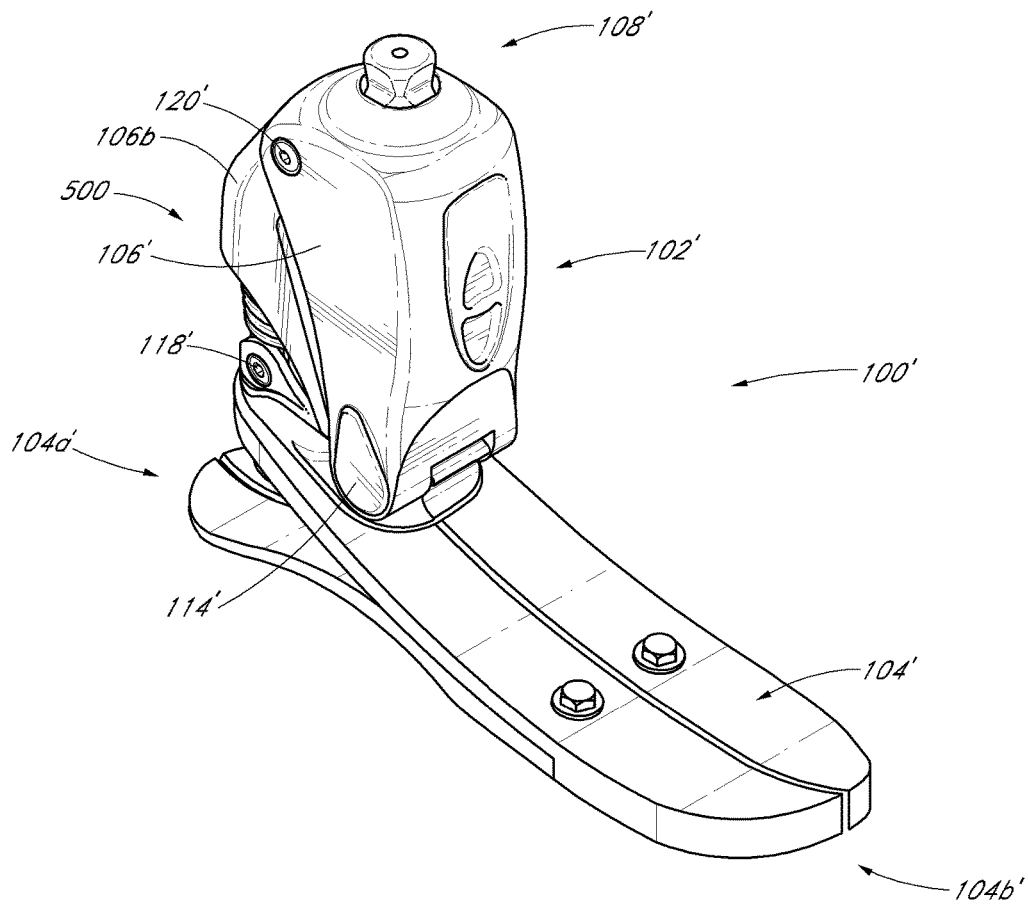
FIG. 12A is a perspective view of another embodiment of a lower limb prosthesis.
Figure 13:
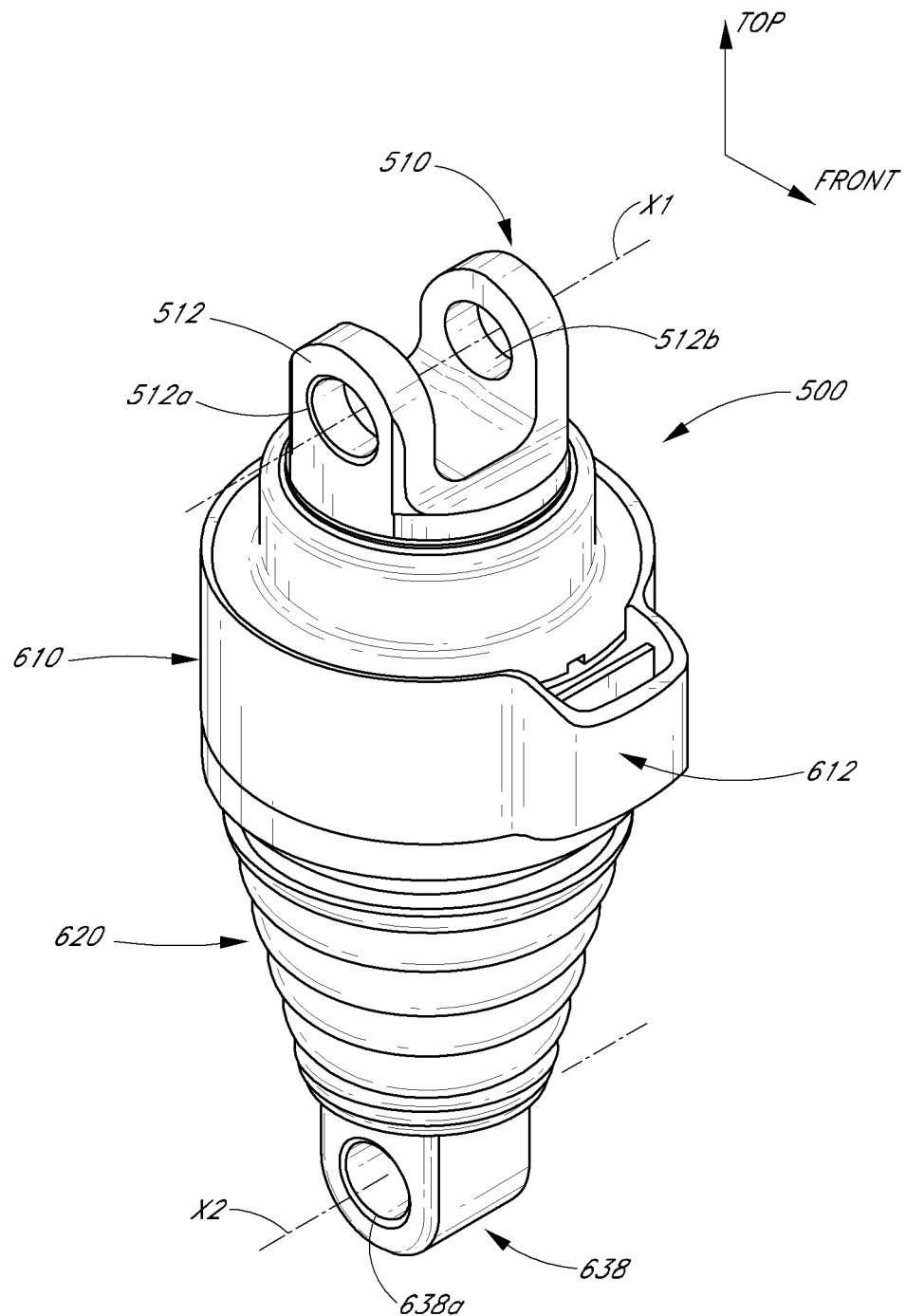
FIG. 13 is a perspective view of one embodiment of an actuator which may be used with the lower limb prosthesis of FIG. 12A.
Figure 15:
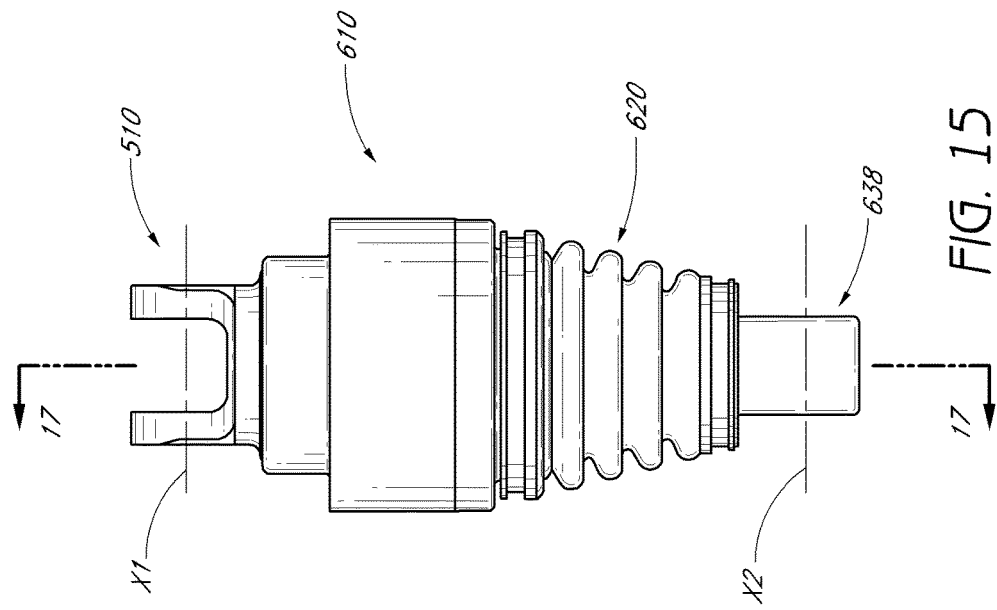
FIG. 15 is a rear view of the actuator of FIG. 13.
Figure 14:
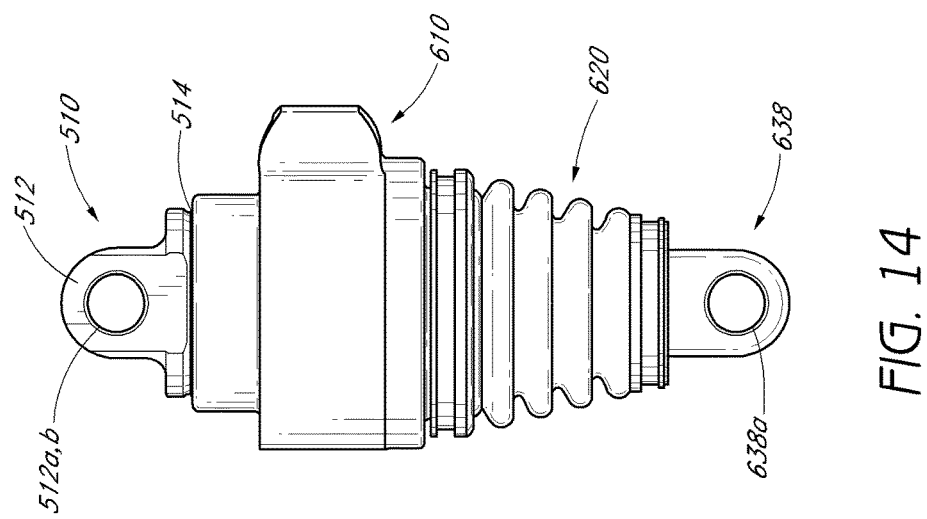
FIG. 14 is a side-view of the actuator of FIG. 13.

FIGS. 12A-12C illustrate another embodiment of a lower limb prosthesis 100' configured to be attached to a human limb. The lower limb prosthesis 100' is similar to the lower limb prosthesis 100 illustrated in FIG. 2, except as noted below. Thus, the reference numerals used to designate the various components of the lower limb prosthesis 100' are identical to those used for identifying the corresponding components of the lower limb prosthesis 100 in FIG. 2, except that a "'" has been added to the reference numerals.

The lower limb prosthesis 100' comprises a first portion 102' coupled to a second portion 104', wherein the portions 102', 104' are moveable relative to each other to mimic a natural human joint. In the illustrated embodiment, the first portion is a lower limb member 102' and the second portion is a prosthetic foot unit 104' operatively coupled to the lower limb member 102' to mimic a natural human ankle joint. The foot unit 104' includes a heel portion 104a' at a rear end of the foot unit 104' and a toe portion 104b' at a front end of the foot unit 104'. In one embodiment, the heel and toe portions 104a', 104b' can be unitary. In another embodiment, the heel and toe portions 104a', 104b' can be separate components fastened to each other via, for example, bolts, screws, adhesives and the like. In the illustrated embodiment, the prosthetic foot unit 104' is an LP VARI-FLEX® prosthetic foot commercially available from Össur. However, the foot unit 104' can have other configurations or designs. In another embodiment (not shown), the first and second portions can be an upper leg member and a lower leg member, respectively, which are coupled to mimic a natural human knee joint.

As shown in FIG. 12A, the lower limb prosthesis 100' may also comprise a frame 106' extending between the foot unit 104' and the lower limb member 102'. As shown in FIGS. 12A and 12B, an attachment portion 108' of the lower limb member 102' facilitates the coupling of the lower limb member 102' to another member, such as, for example, the pylon 110 depicted in FIGS. 1-4. In the illustrated embodiment, the attachment portion 108' is a pyramid. Additionally, the lower limb member 102', or support member, couples to the foot unit 104' at its lower end via a pivot assembly 114', which is attached to the prosthetic foot unit 104'. In the illustrated embodiment, the pivot assembly 114' is attached at about the rear ⅓ of the foot unit 104'. However, the pivot assembly 114' can be attached at other locations on the foot unit 104'. Preferably, the pivot assembly 114' mimics a natural human ankle joint. Additionally, a cover 106b' is disposed about an actuator 500 of the lower limb prosthesis 100' to substantially protect the actuator 500 and inhibit the intrusion of foreign matter. In certain embodiments, the lower limb prosthesis 100' may also include a control wire, such as the control wire 112 depicted in FIGS. 1-4, to provide power to and/or communicates control signals to the prosthesis 100'.

With continued reference to FIGS. 12A-12C, the actuator 500 provides the prosthesis 100' with the necessary energy to execute angular displacements synchronized with an amputee's locomotion. The actuator 500 couples the first and second portions 102', 104' of the prosthesis 100' together, which in the illustrated embodiment correspond to the lower limb member 102' and the prosthetic foot unit 104'. As discussed further below, the actuator is configured to adjust an angle between the lower limb member 102' and the foot unit 104'. The actuator 500 couples to the foot unit 104' and the lower limb member 102' at first and second attachment points 118', 120', respectively. In one embodiment, the prosthesis can include control circuitry to control the operation of the actuator 500, such as, for example, the control circuitry 122 depicted in FIGS. 2 and 3.

FIGS. 13-18 illustrate one embodiment of an actuator 500 that may be used with the lower limb prosthesis 100' discussed above. The actuator 500 preferably comprises a stator or top unit 510 having an attachment end 512 and a bottom end 514. In the illustrated embodiment, the attachment end 512 is a C-shaped clamp (see FIG. 15) having a first opening 512a and a second opening 512b aligned along a first axis X1 that extends generally perpendicular to a longitudinal axis Y of the actuator 500. However, the attachment end 512 can have other suitable configurations. The openings 512a, 512b are preferably sized to receive a fastener therethrough, such as a bolt, screw, or pin (not shown), to allow the top unit 510 to be fastened to, for example, the upper end of the lower limb member 102' at the second attachment point 120'.

Figure 17:
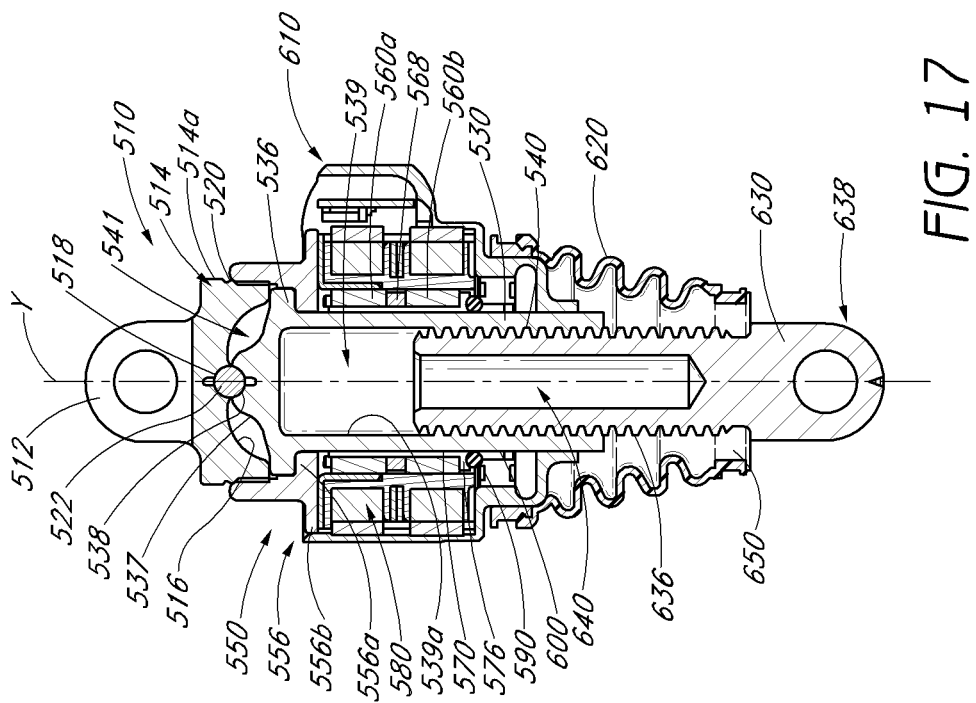
FIG. 17 is a cross-sectional side view of the actuator of FIG. 13.
Figure 16:
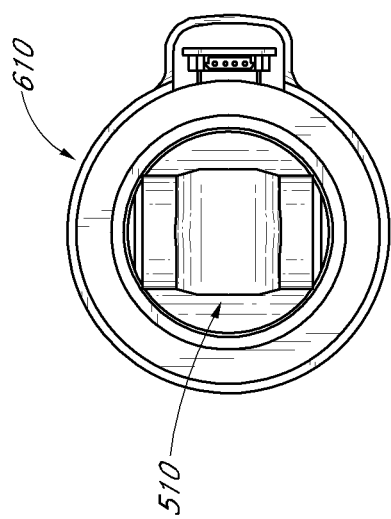
FIG. 16 is a top view of the actuator of FIG. 13.

The bottom end 514 of the top unit 510 preferably has a circumferential wall 514a and a bottom surface 516. In the illustrated embodiment, as shown in FIG. 17, the bottom surface 516 curves from the circumferential wall 514a toward a center of the bottom surface 516. The bottom surface 516 preferably includes a recess portion 518 located generally at the center of the bottom surface 516. The recess portion 518 on the bottom surface 516 of the top unit 510 is preferably sized to receive a ball bearing 522 therein, as further discussed below.

As illustrated in FIG. 17, the circumferential wall 514a includes a protrusion 520 that extends outward from the wall 514a. In one embodiment, the protrusion 520 extends substantially along the entire circumference of the wall 514a. In another embodiment, the protrusion 520 can be a plurality of protrusions positioned at discrete locations about the circumference of the wall 514a.

The actuator 500 also comprises a first elongate member or rotor 530 with a body extending from a top end 530a to a bottom end 530b along a length 532, and having a diameter 534. In one embodiment, the length 532 is between about 25 mm and about 70 mm. In one embodiment, the diameter 534 is between about 12 mm and about 40 mm. More preferably, the diameter 534 is about 17 mm. The rotor 530 has a circumferential flange 536 at the top end 530a, the flange 536 having a diameter greater than the diameter 534 of the body. The top end 530a has an outer surface 537 that curves generally upward from the circumferential flange toward a center 537a of the surface 537. The surface 537 defines a recessed portion 538 generally disposed at the center 537a thereof. The recessed portion 538 is preferably contoured to receive the ball bearing 522 therein, such that the ball bearing 522 couples the top unit 510 to the rotor 530. In one preferred embodiment, the top unit 510 and the rotor 530 couple to each other solely via the ball bearing 522. In the illustrated embodiment, the ball bearing 522 is a single ball bearing. However, other suitable bearings can be used. In one embodiment (not shown) a thrust bearing is disposed between the top unit 510 and the rotor 530. As shown in FIG. 17, the rotor 530 is preferably an elongate nut defining a hollow central portion 539, which defines a wall 539a with threads 540 disposed along at least a portion the length of the wall 539a.

As discussed above, the ball bearing 522 preferably couples the top unit 510 to the first elongate member 530. Preferably, the curvature of the surface 537 of the rotor 530 and the curvature of the bottom surface 516 of the top unit 510 define a gap 541 therebetween. The gap 541 extends preferably circumferentially about the center 537a of the surface 537. In a preferred embodiment, at least one magnet 542 is disposed in the gap 541 and attached to the surface 537 via, for example, an adhesive. In the embodiment illustrated in FIG. 18, a plurality of magnets 542 are disposed about the center 537a of the surface 537. In another embodiment, an annular magnet (not shown) can be disposed on the surface 537, with the annulus of the magnet aligned with the center 537a. The magnets 542 are preferably configured to exert a magnetic force on the top unit 510 and the rotor 530, so that the force draws the top unit 510 and the rotor 530 toward each other.

Figure 18:
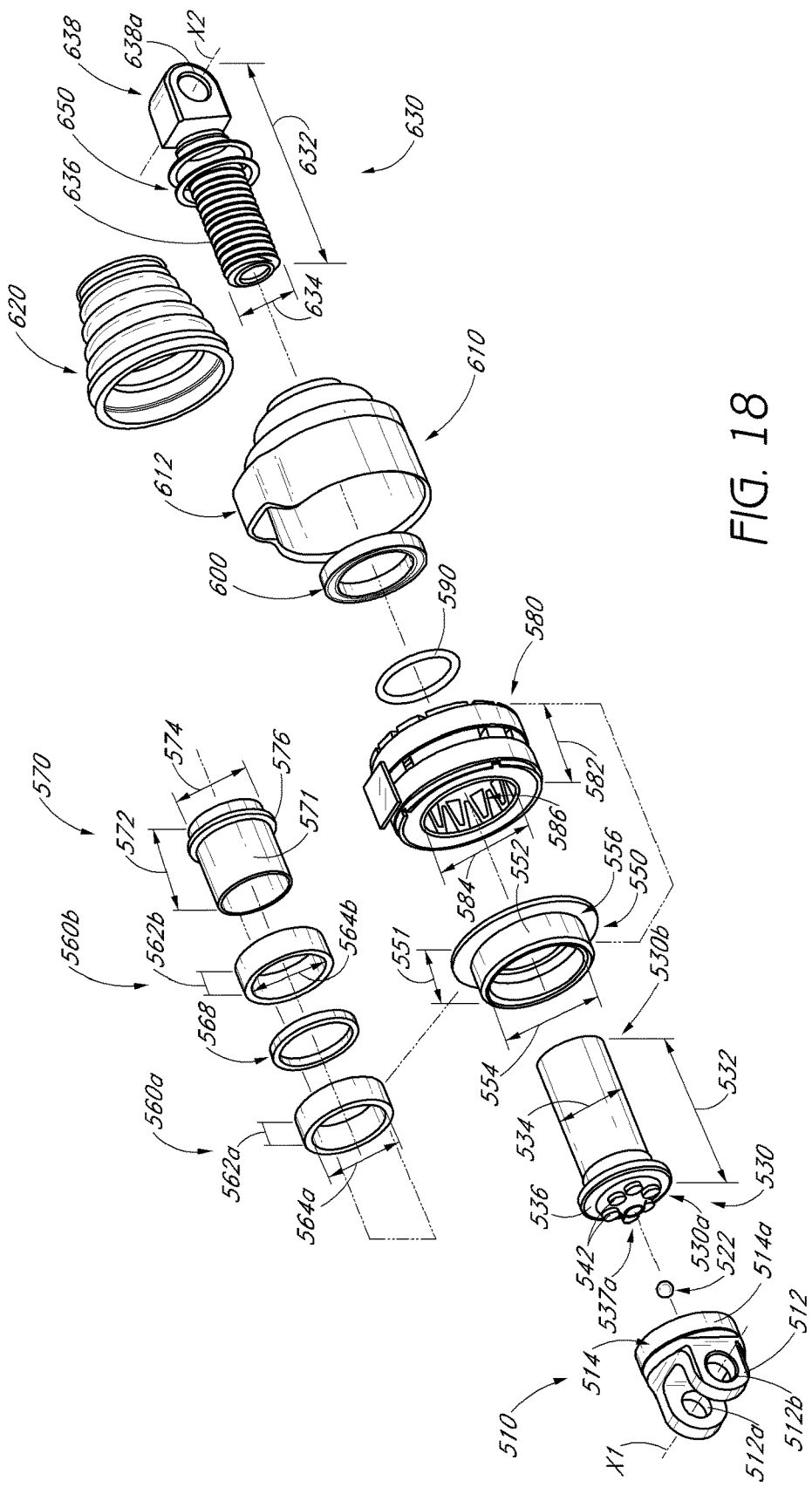
FIG. 18 is an exploded view of the actuator of FIG. 13.

As best seen in FIGS. 17 and 18, the actuator 500 also includes a retainer 550 having a height 551 and a wall 552 defining an inner diameter 554. The retainer 550 includes a flange 556 having an inner portion 556a extending radially inward from the wall 552 and an outer portion 556b extending radially outward from the wall 522, wherein the inner and outer portions 556a, 556b are preferably disposed at a bottom end of the wall 552. Though the illustrated embodiment shows the flange 556 as being continuous around the circumference of the retainer 550, one of ordinary skill in the art will recognize that the flange 556 can instead be a plurality of flange members disposed at discrete locations about the circumference of the retainer 556. The inner diameter 554 of the retainer 550 is sized to receive the rotor 530 and the top unit 510 therein.

In the illustrated embodiment, the inner diameter 554 of the retainer 550 is preferably at least slightly greater than the diameter of the flange 536 of the rotor 530, so that the flange 536 of the rotor 530 does not engage the wall 552 of the retainer 550. Similarly, the inner diameter 554 of the retainer 550 is preferably at least slightly greater than the diameter of at least a portion of the circumferential wall 514a of the top unit 510. The protrusions 520 on the circumferential wall 514a of the top unit 510 preferably engage a portion of the wall 552 of the retainer 550, such that the top unit 510 and the retainer 550 are coupled to each other.

Preferably, rotor 530 rotates about, and translates along, the longitudinal axis Y, as further discussed below. In one embodiment, the rotor 530 remains coupled to the top unit 510 via the ball bearing 522, but selectively moves in and out of contact with the retainer 550 via the inner flange 556a, as further described below. In another embodiment, the rotor 530 moves between contact with the top unit 510, via the ball bearing 522, and contact with the retainer 550 via the inner flange 556a.

As best shown in FIGS. 17 and 18, a first magnet 560a and a second magnet 560b are disposed about a portion of the rotor 530. The first and second magnets 560a, 560b preferably have a height 562a, 562b and an inner diameter 564a, 564b larger than the diameter 534 of the rotor 530, so that the magnets 560a, 560b fit about the rotor 530. In one embodiment, the inner diameters 564a, 564b of the first and second magnets 560a, 560b are between about 12 mm and about 40 mm, and more preferably about 17 mm. In one embodiment, the magnets 560a, 560b are magnetized rings with 24 poles. Additionally, as shown in FIG. 17-18, a spacer 568 is disposed between the first and second magnets 560a, 560b. Preferably, the spacer 568 also has a diameter greater than the diameter 534 of the rotor 530, so that the spacer 568 fits about the rotor 530. Though the illustrated embodiment depicts two magnets 560a, 560b and one spacer 568, one of ordinary skill in the art will recognize that any number of magnets and spacers can be used.

The actuator 500 also comprises a sleeve 570 with a cylindrical body 571 having a length 572 and a diameter 574 such that the sleeve 570 fits about the rotor 530. In one embodiment, the length 572 is between about 10 mm and about 70 mm, and more preferably about 20 mm. The diameter 574 is preferably between about 12 mm and about 40 mm, and more preferably about 17 mm. Preferably, as shown in FIG. 17, the sleeve 570 has an inner diameter greater than the diameter 534 of the first elongate member 530, and has an outer diameter that is smaller than the inner diameter of the first and second magnets 560a, 560b and the spacer 568. Accordingly, the first and second magnets 560a, 560b and the spacer 568 fit about the sleeve 570, which in turn fits about the rotor 530. In a preferred embodiment, the rotor 530, sleeve 570, magnets 560a, 560b are disposed substantially adjacent each other.

As best illustrated in FIGS. 17 and 18, the sleeve 570 also has a lip 576 that extends circumferentially about the sleeve 570. In a preferred embodiment, the lip 576 extends continuously around the sleeve 570 at a radial distance away from a surface of the sleeve 570 substantially equal to a thickness of at least one of the first and second magnets 560a, 560b. The lip 576 is preferably positioned a distance away from a top end of the sleeve 570 so as to support the first and second magnets 560a, 560b and the spacer 568 about the sleeve 570 so that the first and second magnets 560a, 560b and the spacer 568 do not extend past the top end of the sleeve 570.

The actuator 500 also comprises a motor 580. In the illustrated embodiment, the motor 580 has a height 582 and an inner surface 586 with an inner diameter 584, such that the motor 580 can be disposed about the rotor 530. In one embodiment, the motor has a length of between about 10 mm and about 60 mm, and more preferably about 25 mm. the inner diameter 584 of the motor 580 is preferably between about 15 mm and about 50 mm. In a preferred embodiment, the diameter 584 of the motor 580 is about 22 mm. As illustrated in FIG. 17, the motor 580 extends about the rotor 530, such that the sleeve 570, the first and second magnets 560a, 560b and the spacer 568 are disposed between the rotor 530 and the inner diameter 584 of the motor 580. The motor 580 preferably comprises windings configured to rotate the rotor 530 via the magnets 560a, 560b. In the illustrated embodiment, the motor 580 is a stepper motor. However, other suitable motor types can be used. For example, the motor 580 can be a DC motor, a piezo-electric motor, a DC brushless motor, and a servo motor.

As best shown in FIG. 18, the actuator also comprises an o-ring 590 and a roller bearing 600 disposed between the motor 580 and a cover portion 610 having a protruding portion 612. The cover 610 preferably houses the motor 580 therein when the actuator 500 is fully assembled. A bellows 620 is preferably disposed adjacent a bottom end of the cover 610. The bellows 620 advantageously inhibits the entry of foreign particles, such as dust and water, into contact with the motor 580 and a second elongate member 630 of the actuator 500.

The second elongate member 630 extends along a length 632 and has a diameter 634. In the illustrated embodiment, the second elongate member 630 is a screw with threads 636 along a portion of the length 632. In the illustrated embodiment, the screw 630 has an attachment portion 638 at a bottom end thereof with an opening 638a that extends therethrough along an axis X2 generally orthogonal to the longitudinal axis Y of the actuator 500. The opening 638a is preferably sized to receive a fastener therethrough, such as a bolt, a screw or a pin. Accordingly, the attachment portion 638 can be fastened to, for example, the prosthetic foot unit 104' at the first attachment point 118'.

In one preferred embodiment, the threads 636 of the screw 630 are adapted to threadingly engage the threads 540 on the nut 530. Preferably, the threads 636, 540 on the screw 630 and the nut 530, respectively, are designed to be on the boundary of a self-locking coupling. In one preferred embodiment, the threads 636, 540 of the nut 530 and the screw 630, respectively are trapezoidal threads. For example, the threads 636, 540 can be ACME centralized threads with a working diameter of about 14 mm, a pitch of about 2 mm, and about two leads. However, any suitable thread type can be used. In one embodiment, the threads 636, 540 are made of Aluminum Bronze and Stainless Steel. However, other suitable metals and alloys can be used. In one preferred embodiment, the threads 540 in the nut 530 are cut, while the threads 636 in the screw 630 and ground and coated with a coating, such as a permanent oil coating. Advantageously, the thread lengths in the nut 530 are configured to provide a particular level of friction during operation of the actuator 500, while delivering increased support and strength to the actuator 500. However, one of ordinary skill in the art will recognize that the threads 540, 636 of the nut 530 and the screw 630 can have other configurations and be made of other materials to provide a desired performance characteristic. For example, the material and coating of the threads, as well as the pitch, working diameter, and number of leads can be varied to provide a different interface friction between the threads 636, 540. In one embodiment, the pitch and configuration of the threads 636, 530 can be chosen so that a load applied (e.g., along the longitudinal axis Y) to the screw 630 and/or nut 530 assembly will not initiate a self-generated movement of the actuator 500. That is, the pitch and configuration of the threads 636, 530 generate a friction force therebetween that is large enough to inhibit the relative rotation of the nut 530 and the screw 630. In another embodiment, the pitch and configuration of the threads 636, 530 can be chosen so that a load applied to the screw 630 and/or nut 530 along the longitudinal axis Y will initiate a self-generated movement of the actuator 500.

As shown in FIG. 17, the screw 630 preferably has a hollow portion 640 extending along a portion of the length 632. Advantageously, the hollow portion 640 reduces the weight of the screw 630, thereby reducing the weight of the actuator 500 as a whole. As shown in FIG. 18, an adoption ring 650 is disposed about the screw 630, wherein the ring 650 couples with the bottom end of the bellows 620.

Advantageously, the actuator 500 has a compact assembly. As discussed above, the motor 580 is disposed about the rotor 530, which is disposed about the elongate member or screw 630. Accordingly, the actuator 500 takes up less space and can have a lower height than other designs. In one preferred embodiment, the actuator 500 has a height of between about 40 mm to about 70 mm in a collapsed configuration, and a height of between about 65 mm to about 130 mm in a fully extended configuration. Additionally, the hollow portion 640 of the screw 630 advantageously reduces the weight of the actuator 500.

In operation, the actuator 500 advantageously decreases friction between the stator or top unit 510 and the rotor or nut 530. The ball bearing 522 disposed between the top unit 510 and the nut 530 inhibits the generation of a friction force between the top unit 510 and the nut 530, thereby allowing the nut 530 to rotate generally freely relative to the top unit 510. Additionally, the magnets 542 draw the nut 530 toward the top unit 510, as discussed above. Such a magnetic force lifts the nut 530 from engagement with the inner flange 556a of the retainer 550, thereby inhibiting the generation of friction between the retainer 550 and the nut 530, as further discussed below. In a preferred embodiment, the magnetic force is strong enough to lift the rotor 530 from engagement with the inner flange 556a of the retainer in one desired phase of a gait cycle. In another embodiment, the magnetic force of the magnets 542 is strong enough to lift the rotor 530 from engagement with the inner flange 556a of the retainer 550 in more than one desired phase of a gait cycle.

The actuator 500 can also advantageously be selectively locked during a desired phase of a gait cycle. As illustrated in FIG. 17, the flange 536 of the rotor or nut 530 can engage the inner flange 556a of the retainer 550, generating a friction force between the rotor 530 and the retainer 550 to inhibit the rotation of the rotor 530. Thus, the friction force that is generated is effectively a locking force that locks the actuator 500. In one preferred embodiment, the flanges 536, 556a engage when the actuator 500 is in tension. Additionally, as discussed above, the interaction of the threads 636, 540 of the screw 630 and the nut 530 can also generate a friction force to inhibit the rotation of the screw 630 and the nut 530 relative to each other. Thus, the interaction of the threads 636, 540 also generates a locking force that contributes to the locking of the actuator 500.

Figure 19:
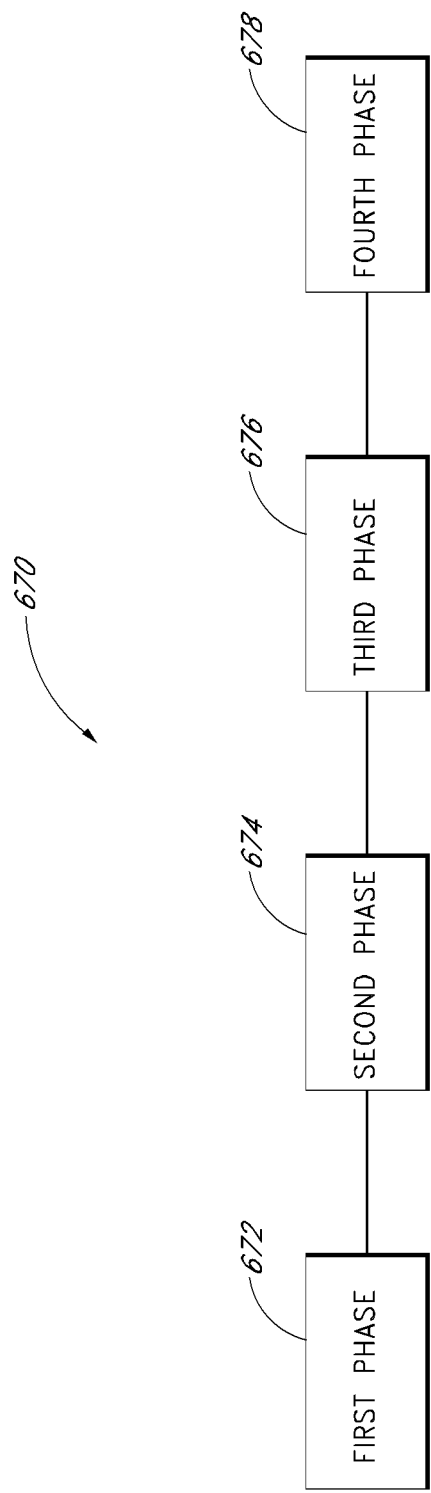
FIG. 19 is a flow chart illustrating different phases of motion of the prosthesis shown in FIG. 12A.

The operation of the actuator 500 during the operation of the lower limb prosthesis 100' by a user will now be described. FIG. 19 illustrates a flow chart showing the different phases of a gait cycle 670 of the lower limb prosthesis 100' illustrated in FIGS. 12A-12C. In a first phase 672 of the gait cycle 670, during heel strike of the foot unit 104', the actuator 500 is initially in a state of compression, wherein the flange 536 on the rotor 530 is displaced relative to the inner flange 556a on the retainer 550.

The state of compression in the first phase arises from the operating relationship between the lower limb member 102' and the prosthetic foot unit 104'. During heel strike, a load is applied on the heel portion 104a' of the foot unit 104' (e.g., due to the weight or locomotion force of the user). Said load applies an upward force on the heel portion 104a' of the foot unit 104', causing the toe portion 104b' to move away from the lower limb member 102' by rotating about the main pivot axis of the pivot assembly 114', which in turn applies a compression force on the second elongate member 630 via the first attachment point 118'. The compression force is transferred from the second elongate member 630 onto the rotor 530, so that the flange 536 of the rotor 530 moves away from the inner flange 556a of the retainer 550.

In one preferred embodiment, the actuator 500 is not actuated during the first phase 672. However, to inhibit the rotation of the rotor 530 relative to the second elongate member 630 during the first phase 672 due to the applied load, the pitch of the threads 540, 636 between the rotor 530 and the second elongated member 630 advantageously generate an interface friction force between the threads 540, 636.

The lower limb prosthesis 100' transitions into a second phase 674 where the foot unit 104' is in a stance phase. During said transition, the actuator 500 transitions from a state of compression to a state of tension, so that a friction force is generated between the flange 536 of the rotor 530 and the inner flange 556a of the retainer 550, as discussed above.

The state of tension in the stance phase is generated by the movement of the lower limb member 102' relative to the prosthetic foot member 104' as the prosthesis 100' transitions into the second phase 674. As the prosthesis 100' moves through the second phase 674, the locomotion of the user (e.g., due to forward movement) applies a load on the lower limb member 102', urging the lower limb member 102' toward the toe portion 104b' of the prosthetic foot unit 104', thus placing a load on the toe portion 104b'. Said load causes a rear portion of the foot unit 104' to move downward, away from the lower limb member 102', which in turn applies a tension force on the second elongate member 630 via the first attachment point 118'. The tension force is transferred from the second elongate member 630 onto the rotor 530, so that the flange 536 of the rotor 530 moves toward, and into engagement with, the inner flange 556a of the retainer 550. As discussed above, said engagement between the flange 536 of the rotor 530 and the inner flange 556a of the retainer 550 generates a friction force to inhibit the rotation of the rotor 530. In one preferred embodiment, the friction force is high enough to act as a brake to prevent the rotation of the rotor 530. Furthermore, in one preferred embodiment, the actuator 500 is not actuated during the second phase 674.

In a third phase 676, the foot unit 104' transitions from a stance phase to a toe-off phase. In toe-off, the toe portion 104b' continues to be under load, as in the second phase. Accordingly, the actuator remains substantially in a state of tension, so that the rotor 530 is inhibited from rotating, as discussed above. In one embodiment, the load on the toe portion 104b' is greater in the third phase than in the second phase of the gait cycle. In one preferred embodiment, the actuator 500 is not actuated during the third phase 676.

In a fourth phase 678, the prosthetic foot unit 104' is in a swing phase between toe-off and heel-strike, wherein the foot 104' is not in contact with a support surface. In the fourth phase 678, the actuator 500 is in a compression position. As discussed above, while in compression the flange 536 on the rotor 530 is separated from the inner flange 556a of the retainer 550, thereby allowing the rotor 530 to rotate generally freely relative to the retainer 550.

The state of compression during the swing phase arises from the operating relationship between the lower limb member 102' and the prosthetic foot unit 104'. During the swing phase, a load is applied to the prosthetic foot unit 104' due to the configuration of the foot unit 104' (e.g., the weight of the foot unit 104'), which pulls the toe portion 104b' downward, away from the lower limb member 102'. The downward force on the toe portion 104b' in turn applies a compression force on the second elongate member 630 via the first attachment point 118'. The compression force is transferred from the second elongate member 630 onto the rotor 530, so that the flange 536 of the rotor 530 moves away from the inner flange 556a of the retainer 550. The rotor 530 is thus able to rotate generally freely relative to the retainer 550. In one embodiment, the movement of the flange 536 of the rotor 530 away from the inner flange 556a of the retainer 550 is facilitated by the magnets 542, which draw the rotor 530 toward the top unit or stator 510 and away from the retainer 550, thus inhibiting the generation of friction during the swing phase.

In one preferred embodiment, the actuator 500 is actuated during the swing phase to adjust the angle between the lower limb member 102' and the prosthetic foot unit 104'. Advantageously, the ball bearing 522 disposed between the stator 510 and the rotor 530 also inhibit the generation of friction between the rotor 530 and the retainer 550. Therefore, the actuator 500 is actuated while under a light load, which advantageously reduces the wear and tear on the actuator 500, providing for an extended operating life.

As discussed above, in one embodiment the actuator 500 inhibits the rotation of the rotor 530 relative to the second elongate member 630 when in a state of tension. However, one of ordinary skill in the art will recognize that in another embodiment the actuator 500 can be operated to inhibit the rotation of the rotor 530 relative to the second elongate member 630 while in compression. Moreover, in another embodiment the actuator 500 can also be arranged so as to allow for the rotation of the rotor 530 relative to the second elongate member 630 when in a tension position. For example, in one embodiment the magnets 542 can generate a magnetic force sufficient to draw the rotor 530 away from the inner flange 556a of the retainer 550 while the actuator 500 is in a state of tension. Additionally, as discussed above, the actuator 500 is actuated during the swing phase 678 of a gait cycle. However, one of ordinary skill in the art will recognize that the actuator 500 can be actuated during more than one phase of a gait cycle.

Though the operation of the actuator 500 is discussed above in relation to a lower limb prosthesis 100', one of ordinary skill in the art will recognize that the actuator 500 can also be used with an orthotic device to adjust the angle of a first portion and a second portion of the orthotic device. Additionally, the actuator 500, as described in the embodiments above, can advantageously be used to selectively lock the orthotic device during a desired phase of locomotion, as well as to decrease friction between the rotor 530 and the retainer 550 during the actuation of the actuator 500 to facilitate the operation of the orthotic device.

In certain embodiments of the invention, a lower limb prosthesis or orthosis includes at least one sensing device coupled thereto and that is substantially isolated from negative external effects or loads. For example, in certain embodiments, the sensing device is capable of measuring angular movement of a prosthetic foot in a single direction while disregarding or filtering out movement and/or loads of the prosthetic foot in other directions.

Figure 20:
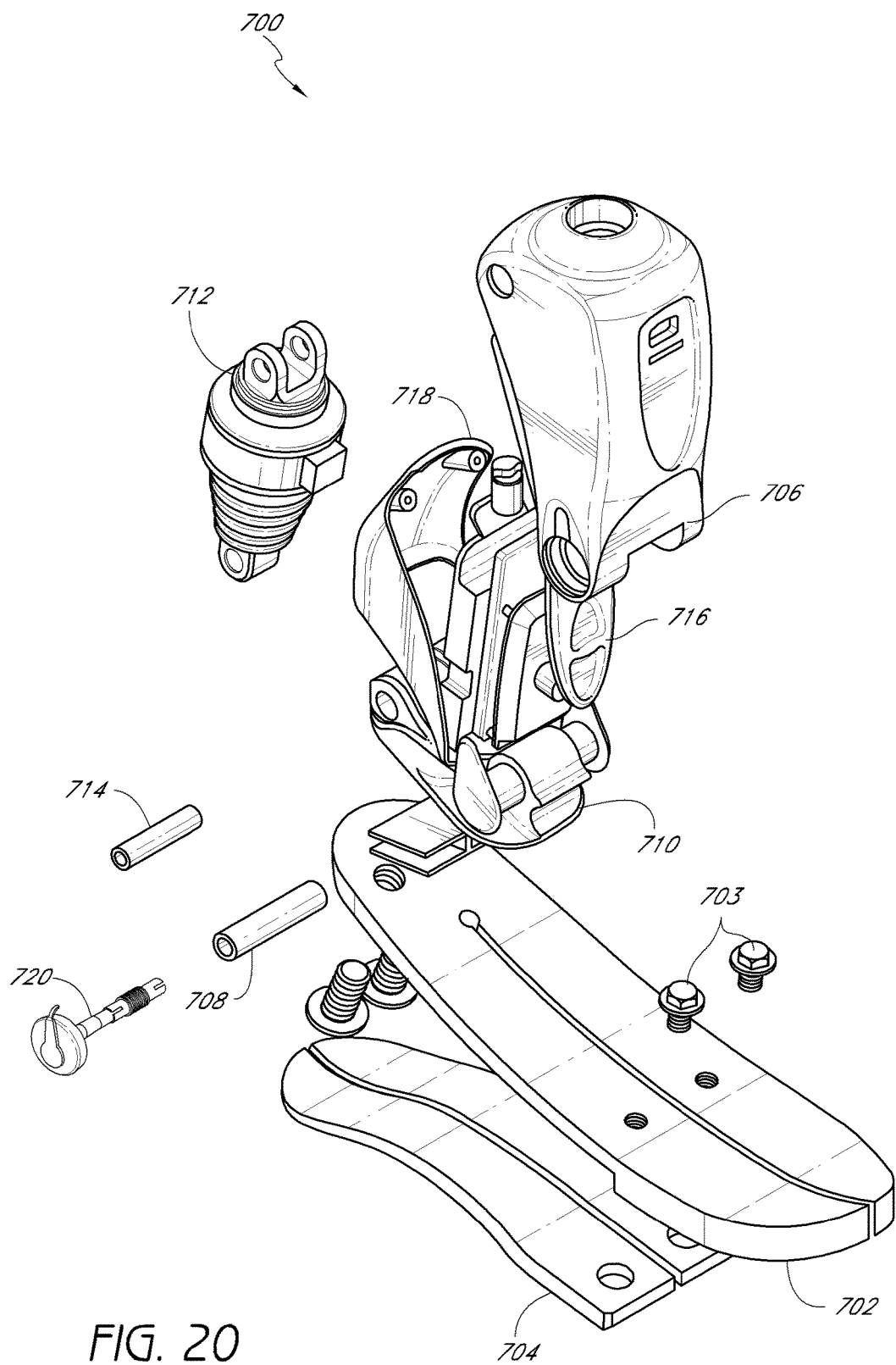
FIG. 20 is a disassembled view of a lower limb prosthesis having an ankle-motion-controlled foot unit according to another embodiment of the invention.

For example, FIG. 20 illustrates a disassembled view of a lower limb prosthesis 700 having an ankle-motion-controlled foot unit. For ease of reference and depiction, certain components, such as certain bolts, washers, bearing plugs and the like, are not shown and described with reference to the illustrated prosthesis 700. A skilled artisan would recognize however, from FIG. 20 and the disclosure herein which components, or equivalents thereof, may be used with the depicted components of the illustrated prosthesis 700.

In certain embodiments, the prosthesis 700 includes at least one sensor assembly that advantageously detects rotation of the foot unit about a single axis and substantially neglects axial and radial movement of the foot unit with respect to the axis. For example, such a sensor assembly may be coupled to and or located near an axis of rotation of the prosthesis 700.

With reference to FIG. 20, the illustrated lower limb prosthesis 700 comprises a foot member 702 connectable by screws 703 to a heel member 704. As shown, the foot member 702 and heel member 704 may comprise a foot unit, such as an LP VARI-FLEX® prosthetic foot commercially available from Össur. In yet other embodiments, the foot member 702 and/or heel member 704 may take on other configurations, or the lower limb prosthesis 700 may operate without a heel member 704.

As illustrated, the foot member 702 is configured to rotatably attach to a main frame 706, or attachment member, about a main pivot pin 708 extending through a base part 710. In certain embodiments, the main pivot pin 708 and the base part 710 form a pivot assembly that is configured to substantially mimic the natural motion of a healthy human ankle. For example, the main pivot pin 708 may allow for dorsiflexion and plantarflexion of the foot member 702, as is described in more detail previously with respect to the prosthesis 100 of FIGS. 1-6.

The prosthesis 700 further includes an actuator 712 operatively coupled to the foot member 702 through the base part 710. In particular, the actuator 712 couples to a lower pin 714 that allows for rotation of a bottom portion of the actuator 712 with respect to the base part 710 secured to a top, rear portion of the foot member 702. In certain embodiments, the actuator 712 is advantageously capable of adjusting at least one angle between the main frame 706 and the foot member 702, such that the foot member 702 rotates about the main pivot pin 708 of the pivot assembly. In certain embodiments, the actuator 712 comprises any one of the various types of actuators disclosed herein and is capable of actively adjusting the angle between the main frame 706 and the foot member 702 based on one or more signals received from an electronic control system.

As shown in FIG. 20, the lower limb prosthesis 700 optionally further includes a keypad 716 to receive user input and a rear cover 718 that partially covers the actuator 712. The prosthesis 700 may also include other devices and/or couplings to facilitate attachment of the prosthesis 700 to a limb, such as a stump, of an amputee.

The illustrated lower limb prosthesis 700 further includes a sensor assembly 720 configured to couple to and extend through the base part 710 of the pivot assembly. In certain embodiments, the sensor assembly 720 is configured to measure movement of at least one portion of the prosthesis 700 in at least one direction. In certain preferred embodiments, the sensor assembly 720 is configured and positioned to measure movement of a portion of the prosthesis 700 in a single direction.

For example, as illustrated in FIG. 20, at least a portion of the sensor assembly 720 is positioned within the main pivot pin 708 and extends along an axis (e.g., a pivot axis) substantially perpendicular to a longitudinal, or vertical, axis of the main frame 706. The illustrated sensor assembly 720 is capable of detecting, or measuring, rotation of the foot member 702 about the axis of the main pivot pin 708. Furthermore, in certain embodiments, the sensor assembly 720 is secured to the pivot assembly of the prosthesis 700 such that the sensor measurements are not affected by loads or forces in directions other than rotation about the main pivot pin 708. For example, in certain embodiments, axial or radial movements with respect to the axis of the main pivot pin 708 do not affect the measurements of the sensor assembly 720.

Figure 21:
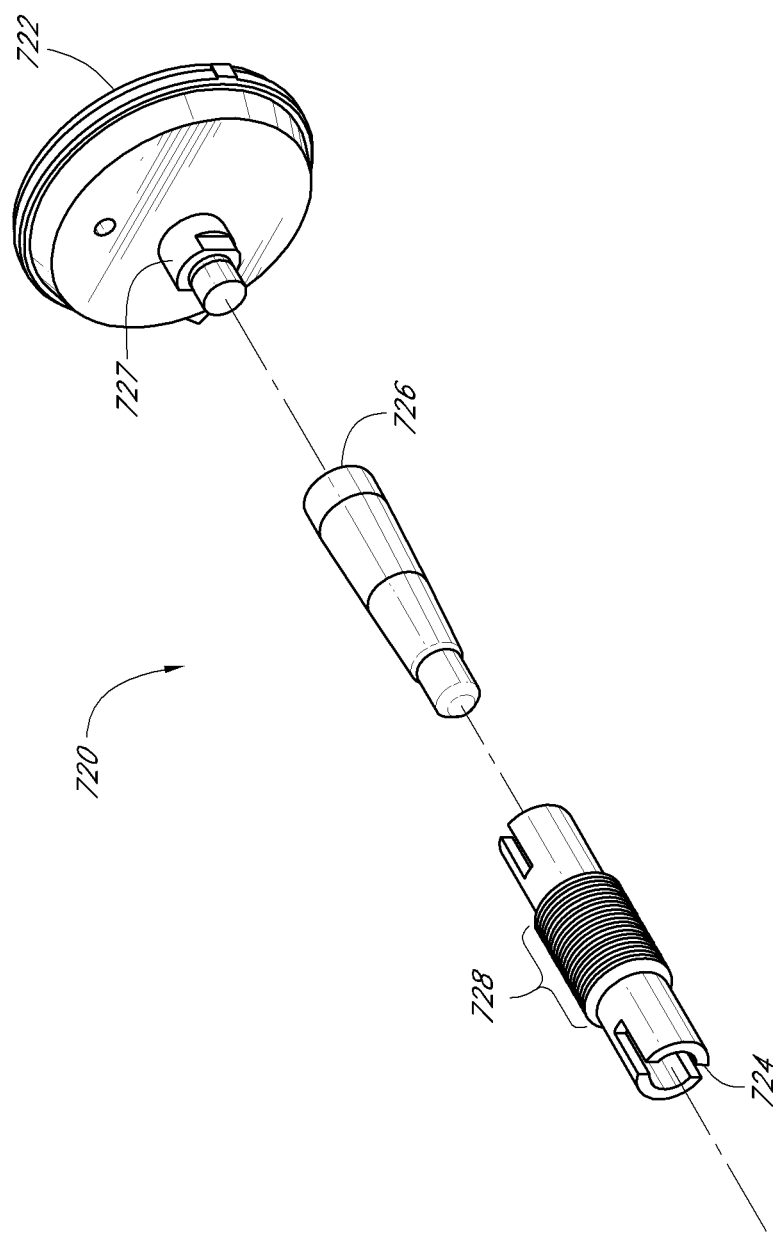
FIG. 21 is a disassembled view of a sensor assembly usable with the lower limb prosthesis of FIG. 20.

FIG. 21 illustrates a disassembled view showing further details of the components of the sensor assembly 720 of FIG. 20. As shown, the sensor assembly 720 includes a displacement measurement sensor 722 coupled to an elongated bellow portion 724 through an extender portion 726. In certain embodiments, relative rotation of the foot member 702 with respect to the main frame 706 is measured by the displacement measurement sensor 722.

Measurements of such rotation may be performed by the sensor assembly 720 in several ways. In certain embodiments, the main pivot pin 708 is rigidly attached to the base part 710, and the elongated bellow portion 724 is positioned at least partially within the main pivot pin 708. In such embodiments, relative movement of the foot member 702 (and attached base part 710) with respect to the main frame 706 causes relative rotation between the elongated bellow portion 724 (and attached extender portion 726) with respect to the displacement measurement sensor 722. For instance, rotation of the foot member 702 may cause rotation of the elongated bellow portion 724 with respect to the displacement measurement sensor 722, which may be fixed with respect to the main frame 706. In other embodiments, rotation of the foot member 702 may cause rotation of the displacement measurement sensor 722 with respect to the elongated bellow portion 722, which may be fixed with respect to the main frame 706.

In certain embodiments, the displacement measurement sensor 722 comprises a potentiometer, such as, for example, a linear or logarithmic potentiometer. In such embodiments, rotation of the elongated bellow portion 724 causes a corresponding rotation of the extender portion 726 and a rotatable input 727 of the potentiometer. In yet other embodiments, other types of displacement measurement sensors may be used, such as, for example, rotational position transducers, optical or mechanical encoders, combinations of the same or the like, to measure movement and/or rotation of a component of the prosthesis 700.

As illustrated in FIG. 21, the elongated bellow portion 724 further includes a plurality of ridges 728 around an outside surface of the bellow portion 724. In certain embodiments, the ridges 728 advantageously eliminate or substantially reduce the effects of axial (e.g., along the axis of the bellow portion 724) and/or radial (e.g., a direction perpendicular to the axis of the bellow portion 724) movements and/or loads on measurements by the displacement measurement sensor 722. For instance, at least some of the ridges 728 may be located within a component housing at least a portion of the elongated bellow portion 724. In certain preferred embodiments, such a component may include the main pivot pin 708 depicted in FIG. 20. In such embodiments, the ridges 728 may advantageously isolate movement of the elongated bellow portion 724 to rotation about the axis of the elongated bellow portion 724 and the main pivot pin 708.

In yet other embodiments, the elongated bellow portion 724 may include a plurality of grooves or other surface features that isolate movement of the elongated bellow portion 724 to a single direction. In yet other embodiments, the sensor assembly 720 may function without the extender portion 726 or the ridges 728. For example, the sensor assembly 720 may include a flexible compression membrane that couples the displacement measurement sensor 722 to the main pivot pin 708 and that absorbs unwanted movement (e.g., axial and/or radial movement).

Although the sensor assembly 720 has been described with reference to particular embodiments, other configurations for the sensor assembly 702 may be used with the prosthesis 700. For example, the main pivot pin 708 may be rigidly attached to the main frame 706. In such embodiments, either the displacement sensor 722 or the elongated bellow portion 724 may also be affixed to the main frame 706 such that relative movement of the foot member 702 with respect to the main frame 706 is detected by the displacement measurement sensor 722.

In yet other embodiments of the invention, the prosthesis 700 may include other types of sensor assemblies usable to detect movement of at least one component of the prosthesis 700. For example, the prosthesis 700 may comprise a ball joint assembly that has its movement constrained in at least one direction by geometric constraints surrounding the ball joint, which constraints may include, for example, one or more pins or flat surfaces that engage one or more surfaces of the ball joint. In yet other embodiments, the sensor assembly 720 may include a flexible material that is stiff against twisting forces but allows for longitudinal compression and/or radial movement.

Furthermore, it will be understood that the sensor assembly and/or prosthesis 700 may advantageously used with a variety of motion-controlled prosthetic and/or orthotic devices, examples of which are described in more detail herein and in U.S. patent application Ser. No. 11/056,344, filed on Feb. 11, 2005, and entitled "SYSTEM AND METHOD FOR MOTION-CONTROLLED FOOT UNIT," which is hereby incorporated by reference herein in its entirety and is to be considered a part of this specification.

As mentioned above with reference to TABLE 1 and FIG. 9, in some embodiments of the invention, there are certain defined states of the ankle device 304. One of these states is the "RELAX" state. In one embodiment, when the sensor module 302 detects that the user has moved to a relaxed position, the control device 300 may initiate the "RELAX" state.

In one embodiment of the invention, the sensor module 302 detects when the user has moved to a relaxed position, such as sitting, crossing legs, reclining, lying down, crawling, leaning, etc. The sensor module 302 may detect these relaxed positions by measuring combinations of vertical acceleration (from which it may determined, for example, whether the overall ankle device 304, particularly the foot unit 104 (with reference to FIG. 1), is in a tilted position with respect to the ground, such as resting on the heel with legs outstretched in a sitting or lying down position), horizontal/lateral acceleration, and time. For instance, the sensor module 302 may comprise an accelerometer capable of measuring acceleration in the y-axis. In one embodiment, the measured vertical acceleration corresponds to the force of gravity. The accelerometer may be placed on the ankle device 304. In one embodiment, the accelerometer may be placed on the lower limb member 102 (with reference to FIG. 1), though the accelerometer may be placed anywhere on the ankle device 304. When placed on the lower limb member 102, the accelerometer may be used to measure an angle of the lower limb member 102 relative to vertical, which may then be used to determine an angle of the overall ankle device relative to the ground. As the ankle device 304 rotates from the upright, vertical position, the corresponding force of gravity will vary relative to the degree of rotation. For instance, when the ankle device 304 is in an upright, vertical position, the accelerometer may measure the standard force of gravity, 9.8 m/s$^2$. As the ankle device 304 rotates from the vertical position, the accelerometer may measure a fraction of the Earth's global force of gravity relative to the changing angle of the ankle device 304 with respect to the ground. Thus, a sensor module 302 configured to measure acceleration in the vertical plane may be used to determine the stationary angle of the ankle device 304 with respect to the ground. For example, the sensor module 302 may indicate that the ankle device 304 is tilted at an angle of 90° with respect to the ground. This might indicate, for example, that the user is lying completely flat on the back. Alternatively, the sensor module 302 may indicate that the ankle device 304 is at an angle of 45° with respect to the ground, indicating perhaps that the user is sitting down with legs outstretched in such a manner as to form a 45° angle with respect to the ground.

In addition to the vertical acceleration, the sensor module 302 may also comprise an accelerometer configured to measure acceleration in the horizontal, or lateral, plane. This accelerometer may measure the ground acceleration of the ankle device 304 as the user moves in horizontal directions. Moreover, the control device 300 may also comprise a timer (not shown) that may be used to measure the amount of time during which the sensor module 302 detects certain conditions of acceleration.

To detect certain relaxed positions, the control device 300 may be configured to monitor the measurements of acceleration by the sensor module 302 over a period of time. In one embodiment, a range of angles of the ankle device 304 compared to the ground is defined that indicates the movement of the user to a relaxed position. To enter into the "RELAX" state, the control device 300 may determine that the angle between the ankle device 304 and the ground, as detected by the sensor module 302, is within the defined range. Additionally or alternatively, a range of lateral/horizontal acceleration of the ankle device 304 may be defined. To enter into the "RELAX" state, the control device 300 may determine that the lateral/horizontal acceleration of the ankle device 304, as detected by the sensor module 302, falls within the defined range. Additionally or alternatively, a range of time may be defined during which the above-mentioned conditions may be met. In other words, to enter the "RELAX" state, the control device 300 may determine that the ankle device, for a specified period of time, is at angle with respect to ground within the defined range and/or is accelerating within the defined range indicative of a user's movement to a relaxed position. Thus, an algorithm that triggers execution of the "RELAX" state might define the variables: start acceleration delta (e.g., the upper limit of possible acceleration of the ankle device 304 that triggers the "RELAX" state), the start angle (e.g., the lower limit of the angle of the ankle device 304 with respect to ground that triggers the "RELAX" state), and start time (the amount of time that a combination of the other variables may be satisfied to trigger the "RELAX" state).

In one embodiment, used for example when a user is sitting down, reclining or crawling, the start acceleration delta may be about 1 m/s$^2$, indicating a threshold such that movement artifacts from the user should be less than about 1 m/s². Alternatively, the acceleration delta may be between about 0.1 m/s² and 50 m/s². The start angle of the foot member relative to the ground may be between about 30 degrees and about −90 degrees, for example, representing that a user is lying down on the stomach. Alternatively, the range of angles may be between about −90° and +90°, the latter representing, for example, that a user is lying down on the back. The start time may for example be about 1 second or more. When each of these variables is satisfied, the ankle device will move to a relaxed state, as described below.

In other embodiments, the control device 300 may detect conditions indicative of a user's movement out of a relaxed position and may initiate an "EXIT" state. The determination of a user's movement out of a relaxed position may be similar to the determination of a user's movement into a relaxed position. Thus, an algorithm that triggers execution of the "EXIT" state might define the variables: end acceleration delta (e.g., the lower limit of possible acceleration of the ankle device 304 that triggers the "EXIT" state) and the end angle (e.g., the lower limit of the angle of the ankle device 304 with respect to ground that triggers the "EXIT" state). In some embodiments, the "EXIT" state may be initiated regardless of whether the "RELAX" state is initiated first. Thus, the "EXIT" state may adjust the device for a preferred configuration for exiting a relaxed position, even if the relaxed position is never detected and/or the "RELAX" state is never initiated. For instance, the control device 300 may detect that the user is in a sitting position without causing the device to adjust to a particular "RELAX" state. It may be advantageous, however, to adjust the device to an "EXIT" state even though a "RELAX" state is not initiated. For example, the "EXIT" state may cause the device to be adjusted to a particular configuration that is advantageous when a user stands up from a sitting position, such as causing the device to dorsiflex in order to help shift the user's center of momentum to be over his/her feet to facilitate standing. This "EXIT" state may be advantageous regardless of whether the device ever initiated a corresponding "RELAX" state.

In one embodiment, to execute the "EXIT" state, the end acceleration delta may be about 25 m/s², allowing the user to exit the "RELAX" state by moving the ankle device greater than about 25 m/s², such as by kicking the ankle device to the ground. Alternatively, the end acceleration delta may be between about 0.1 m/s² and 50 m/s². The "EXIT" state may also be defined by an end angle of the ankle device relative to the ground being between about −80 degrees and about 10 degrees. Alternatively, the range of angles may be between about −90° and 90°.

In one embodiment, the "RELAX" state specifies a particular angle between the foot unit 104 and lower limb member 102 to which the ankle device 304 should be adjusted. For instance, when the control device 300 initiates the "RELAX" state, the control drive module 310 may cause the actuator 316 to adjust the ankle device 304, for example, to a plantarflexion position of at least 10°, more preferably about 15°. (With respect to FIG. 1, a plantarflexion position of about 15° is when the lower limb prosthesis 100 is adjusted such that the angle between the foot unit 104 and the lower limb member 102 is about 15° more than the angle between the foot unit 104 and the lower limb member 102 in the neutral position. At the neutral position, there is 0° of plantarflexion and dorsiflexion. Generally, the "neutral position" is when the lower limb member 102 is vertical relative to a horizontal plane, such as the ground. This neutral position will translate to any range of actual ankle angle depending on the heel height of the foot unit 104.) The plantarflexion of the ankle device 304 may mimic the natural plantarflexion of a human foot, may be functionally advantageous, may be aesthetically appealing, etc. Similarly, when the control device initiates the "EXIT" state, the control drive module 310 may cause the actuator 316 to adjust the ankle device 304, for example, to a dorsiflexion position of at least 5°. In one embodiment, the range of angles may be between about 1° and 15° of dorsiflexion, and as discussed above, may be used either when the ankle is exiting from a "RELAX" state, a neutral position where there is 0° of plantarflexion and dorsiflexion, or any other desired configuration. (Again with reference to FIG. 1, a dorsiflexion position of 10° is when the lower limb prosthesis 100 is adjusted such that the angle between the foot unit 104 and the lower limb member 102 is 10° less than the angle between the foot unit 104 and the lower limb member 102 in the neutral position.)

In other embodiments, the "RELAX" state may specify a certain power mode, such as a low power mode, to which the control device 300 should automatically adjust. For instance, the control device 300 might instruct the power module 318 to enter a low power mode, such as a hibernation mode, when the control device 300 determines to initiate the "RELAX" state. Similarly, the "EXIT" state may specify another power mode, such as a normal power mode, to which the control device 300 should automatically adjust. In yet other embodiments, the "RELAX" state and the "EXIT" state may specify certain heel heights, to which the control device should automatically adjust. In still other embodiments, it may be advantageous not to initiate the "RELAX" state or "EXIT" state for a certain period of time after the conditions for initiating these states have been detected.

In addition to defining certain states, some embodiments of the invention may define certain beneficial adjustments for particular terrain variables. For instance, in some embodiments, there are beneficial adjustments made while the user is ascending an incline or descending a decline. Thus, embodiments of the invention may define beneficial adjustments for responding to changes in inclination and declination, such as adjusting the angle of the ankle device with respect to the ground. FIGS. 5 and 6 illustrate embodiments of the invention engaging an inclining slope and declining slope, respectively. In FIG. 5, angle alpha ($\alpha$) indicates the relative slope of the incline. Similarly, in FIG. 6, angle alpha ($\alpha$) indicates the relative slope of the decline. In FIGS. 5 and 6, the angle theta ($\theta$) indicates the angle between the lower limb member 102 and the foot unit 104 of a lower limb prosthesis 100 having an ankle-motion-controlled foot. When the lower limb prosthesis 100 is in its neutral, unadjusted state, the angle theta ($\theta$) may be described as the neutral angle, or the angle of the lower limb prosthesis 100 on level ground. As the user maneuvers on inclined or declined slopes, the lower limb prosthesis 100 adjusts itself to engage the ground by contracting, for inclines, and by expanding, for declines, the angle theta ($\theta$) between the lower limb member 102 and the foot unit 104. In FIGS. 5 and 6, the lower limb prosthesis 100 has been adjusted such that the angle theta ($\theta$) between the lower limb member 102 and the foot unit 104 increases or decreases a desired amount based on the angle alpha ($\alpha$), which is the measurement of the relative slope. Thus, in FIG. 5, for instance, the angle theta ($\theta$) reflects the neutral angle, measured when the lower limb prosthesis is on level ground, minus the degree of inclination, reflected by the angle alpha ($\alpha$). Similarly, the angle theta ($\theta$) in FIG. 6 reflects the neutral angle plus the degree of declination. For some slopes, it may be desirable not to adjust the lower limb prosthesis 100 to reflect the entire degree of inclination/declination, or may even be desirable to adjust the lower limb prosthesis 100 to reflect more.

Thus, in some embodiments, it is advantageous to adjust the angle of the foot unit 104 to the lower limb member 102 to account for the relative incline and/or decline of the terrain. For example, the angle may decrease by about 0 to 30 degrees when adjusting to an incline, or may increase by about 0 to 30 degrees when adjusting to a decline. When the user is on level ground and the lower limb member 102 is vertical with respect to the horizontal ground surface, the angle between the lower limb member 102 and the foot unit 104 is said to be the neutral angle, or the angle of the device in the neutral position. As described in more detail below, when the device detects that the user is maneuvering on an incline and/or decline, then the device may adjust the changing relative position of the foot unit 104 to the lower limb member 102 during the user's gait according to a response angle based on the detected degree of incline and/or decline. In a sense, the device defines an adjusted neutral angle relative to the incline and/or decline. In other words, when the lower limb member 102 is in the vertical position while the foot unit 104 flatly engages an inclined and/or declined surface, then the angle between the lower limb member 102 and the foot unit 104 may be defined as the adjusted neutral angle for the device with respect to the degree of incline and/or decline.

Subsequent adjustments to the ankle angle between the lower limb member 102 and the foot unit 104 may be made relative to this adjusted neutral angle. In some embodiments, the adjustment may occur only during the swing phase, such that during stance, the angle of the ankle between the lower limb member 102 and the foot unit 104 remains substantially constant at the adjusted neutral angle. Alternatively, the adjustment relative to the adjusted neutral angle may occur during both swing and stance phases. As the user leaves the stance phase and the device moves through the air without contact to the ground, the device may be adjusted as described above relative to the adjusted neutral angle (such as described by FIGS. 8 and 11). In other embodiments, the adjustments may also occur during the stance phase, when the foot unit 104 at least partially engages the ground. In some embodiments, for example on an incline, the foot unit 104 may be adjusted relative to the lower limb member 102 so as to dorsiflex at the heel strike and midstance phase and then at toe off may be adjusted to a plantarflexion angle to provide natural push off. In other embodiments, for example on a decline, the foot unit 104 may be adjusted relative to the lower limb member 102 so as to plantarfex at the heel strike phase and then during late stance and toe off may be adjusted to a dorsiflexion angle to aid roll over. It will be appreciated that these adjustments made during stance may also be utilized when walking on level ground. It will be further appreciated that the adjustments described above for inclined surfaces may be used for declined surfaces, and vice versa.

In some embodiments, the sensor module 302 (with reference to FIG. 9) may be configured to determine if the user is walking up an incline or down a decline. This may be accomplished via dynamic analysis that traces the path of the ankle device 304 in the vertical plane. In one embodiment, two acceleration sensors with two axes measure the relative position of the ankle device to ground (gravity) during the stance phase. In one embodiment, these sensors are located on the lower limb member 102 (with respect to FIG. 1). In other embodiments, the sensors may be located in the soles of shoes, in foot covers, on braces, etc. By measuring the gait from heel strike to toe off and how the foot is lifted in swing, the relative angle of incline and decline may be measured. This is because a user's gait exhibits different characteristics when walking on an incline, on a decline, and on level ground. For instance, there is more toe function than heel strike during incline. Additionally, while walking on an incline, the user lifts the foot more than on level ground and shortens the swing of the gait. Other characteristics may be observed for gait patterns while walking on a decline. Based on an understanding of the differences in gait patterns, the measurements of acceleration may be used to determine the surface angle. Sensors capable of determining the surface angle are available from Dynastream Innovations, Inc. (Alberta, Canada). In some embodiments, the surface angle may be filtered by averaging a number of measurements, such as five measurements.

In some embodiments, the surface angle (or the filtered surface angle) may be applied to a formula that yields an ankle response angle. The ankle response angle is a particular angle by which the lower limb prosthesis 100 (with respect to FIG. 1) should be adjusted for the specified surface angle, thereby configuring the lower limb prosthesis 100 to an adjusted neutral angle. The ankle response angle may be measured with respect to level surface ground. By way of example, if the response angle is 10°, then lower limb prosthesis 100 should be adjusted such that the toe end of the foot member 104 is rotated 10° toward the lower limb member 102, making a 10° angle between the foot member 104 and the ground, assuming that the lower limb member 102 remains fixed with respect to level ground. If the lower limb prosthesis 100 were adjusted 10° in response to the detection of an incline of 10°, then the foot unit 104 of the lower limb prosthesis 100 would completely engage the ground, as illustrated in FIG. 5, for example. If, on the other hand, the response angle is −10°, then lower limb prosthesis 100 should be adjusted such that the toe end of the foot member 104 is rotated 10° away from the lower limb member 102, making a −10° angle between the foot member and the ground, assuming that the lower limb member 102 remains fixed with respect to level ground. If the lower limb prosthesis 100 were adjusted −10° in response to the detection of a decline of 10°, then the foot unit 104 of the lower limb prosthesis 100 would completely engage the ground, as illustrated in FIG. 6, for example.

Figure 22:
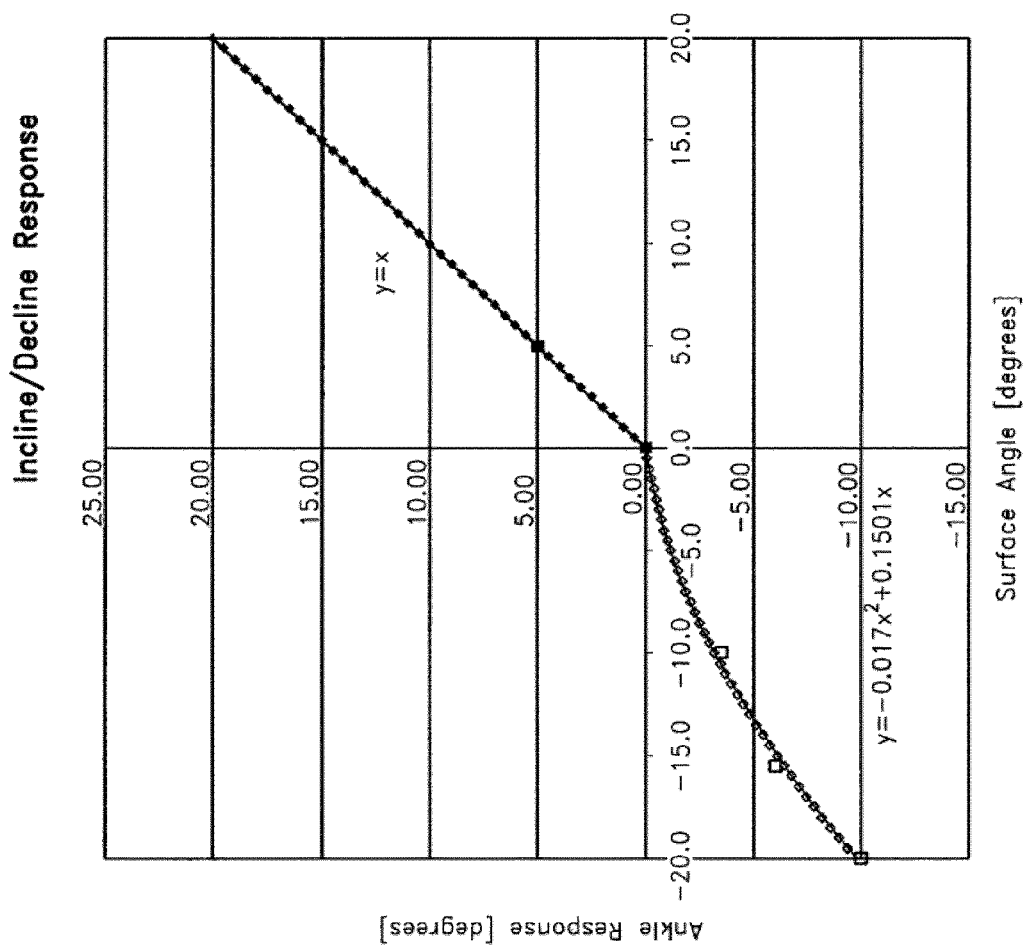
FIG. 22 is a graph illustrating preferred ankle response angles for respective degrees of incline/decline.

In one embodiment, the ratio between the surface angle and the response angle for inclined slopes is 1:1. In another embodiment, the ratio between the surface angle and the response angle for declined slopes is nonlinear, and in one embodiment is given by the formula: $y = -0.017x^2 + 0.1501x$, where y is the ankle response angle and x is the detected (and possibly filtered) surface angle. Other embodiments may result in the response angle for declined slopes being between about 10% and 100% of the measured surface angle, more preferably between about 10% and 50%. FIG. 22 illustrates an x-y graph depicting above-defined ratios between surface angles and ankle response angles for inclines and declines, respectively. Thus, if it is detected that the surface angle of the incline is 5°, then the corresponding response angle is also 5°, representing a 1:1 ratio for inclined surfaces. For declined surfaces, however, the ankle response angles correspond to the above-identified formula. Thus, if it is detected that the surface angle of the decline is −10°, then the corresponding response angle is approximately −2.5°. According to the illustrated embodiment, the response angle for declining surfaces is a fraction of the angle of decline. This result is intuitively understood. As a user walks down a decline, the momentum created by the pull of gravity causes the user to roll through the gait pattern, resulting in less need for the foot unit 104 to automatically rotate downward to engage the ground. While walking up inclines, however, it is desirable for the foot unit 104 to automatically engage the ground without forcing the user to roll over the unbent lower limb prosthesis 100.

Users of prosthetic or orthotic devices often may need more than one device. For example, a trans-femoral amputee may require a combination of a mechatronic knee and a mechatronic ankle or foot. Typically, more natural movement may be achieved when these devices are coordinated. Where two or more of these devices are electronically controlled devices, improved coordination, e.g., from a more natural motion, can be achieved by electronic interface and coordination between devices.

Figure 23:
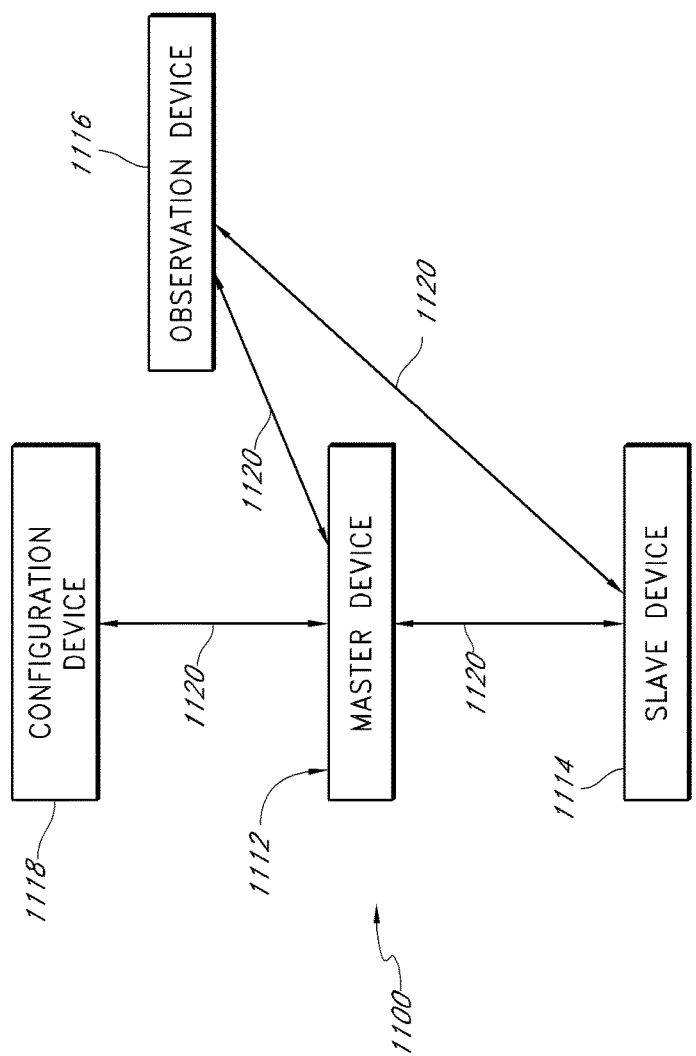
FIG. 23 is a block diagram that illustrates one embodiment of a system including a number of mechatronic devices.

FIG. 23 is a block diagram that illustrates one embodiment of a system 1100 which includes multiple mechatronic devices. In one embodiment, a particular mechatronic device includes one or more sensors, a controller, and one or more actuators. However, it is to be recognized that in other embodiments a particular mechatronic device may include, for example, only sensors, sensors and a controller, one or more actuators, actuators and a controller, or only a controller. In one embodiment, the system may include a master device 1112. In one embodiment, the master device 1112 directs control of the entire system 1100. In one embodiment, the master device 1112 is a mechatronic device that has a control system which incorporates a state machine. The master device 1112 may fully or partially control a slave device 1114. Information on state changes or direct actuation commands may be sent to components of the system 1100, such as the slave device 1114. Embodiments of each of the devices in the system 1100 may include prosthetic knees, prosthetic ankles, or other electronically controlled prosthetic or orthotic devices. For example, an orthotic device such as a brace may include a sensor for measuring knee motion.

In one embodiment, the slave device 1114 may only include a portion of the software or hardware needed to control the slave device 1114. The slave device 1114 may thus be wholly or partially dependent on receiving state information and commands from the master device 1112. In one embodiment, the slave device 1114 may receive sensor data from the master device 1112, or another slave device 1114. The slave device 1114 may also send sensor data to other devices 1112, 1114, 1116, or 1118. In one such embodiment, the slave device 1114 includes one or more sensors but does not include an actuator.

The system 1100 may include an observation device 1116 that is configured to monitor or control one or more of the other devices in the system 1100. In one embodiment, the observation device includes a wristwatch, or arm mounted device, that provides status or other information regarding the operation of devices in the system 1100. In one embodiment, the status information is updated in real-time. In another embodiment, the observation device 1116 may have controls configured to affect the operation of the system 1100. In one such embodiment, the observation device 116 includes only a controller that is configured to receive sensor data and/or send control data to other mechatronic devices in the system 1100. For example, in one embodiment, the master device 1112 may be a prosthetic knee and the observation device 1116 may be used for activation or to provide hints as to different use modes, e.g., walking, bicycling, etc.

The system 1100 may also include a configuration device 1118 that is adapted to control one or more of the other devices in the system. In one embodiment, the configuration device 1118 is in direct communication with the master device 1112. The master device 1112 coordinates communication of configuration data with other devices, e.g., the slave device 1114 or the observation device 1116. In other embodiments, the configuration device 1118 may be in direct communication with all or any subset of the devices 1112, 1114, 1116.

Each of the devices 1112, 1114, 1116, and 1118 of the system 1110 may communicate using a bionic data bus (BDB) 1120. The BDB 1120 may comprise any data communications physical layer, including those known in the art. For example, the BDB 1120 may include one or more of the following communications layers: a remote modem, Ethernet (IEEE 802.3), Token Ring (IEEE 802.5), Fiber Distributed Datalink Interface (FDDI) Asynchronous Transfer Mode (ATM), Wireless Ethernet (IEEE 802.11), Bluetooth (IEEE 802.15.1), or infrared interfaces including IRDA. The BDB bus may also include a peripheral interface bus including Universal Serial Bus (USB), IEEE 1394, Peripheral Component Interconnect (PCI), or other peripheral buses such as those known in the art. In addition, the BDB 1120 may include networks such as an Intranet, a Local Area Networks (LAN), a Wide Area Network (WAN), or the Internet. The BDB 1120 may include additional protocols such as internet protocol (IP) or transmission control protocol (TCP).

It will be recognized that while, in one embodiment, a mechatronic device may operate as one of the devices 1112, 1114, 1116, and 1118, in other embodiments of the system 1100, a particular mechatronic device may be configured to operate in different modes or roles as one or more of the devices 1112, 1114, 1116, and 1118. In one embodiment, the particular mechatronic device may be configured to automatically act as a particular type of device based on data exchange with other devices in the system 1100. For example, one embodiment of the system 100 may include a prosthetic knee, a prosthetic ankle, and a wrist-attached monitor. Embodiments of prosthetic knees may include those illustrated in U.S. Pat. No. 6,610,101, filed Mar. 29, 2001, and issued on Aug. 26, 2003; U.S. patent application Ser. No. 11/123,870, filed May 6, 2005; and U.S. Patent Publication No. 2005-0283257, filed on Mar. 9, 2005; each of which is incorporated by reference in its entirety. Embodiments of prosthetic ankles may include those illustrated in U.S. Patent Publication No. US 2005-0197717, filed Feb. 11, 2005, and which is incorporated by reference in its entirety.

After exchanging identifying data over the BDB 1120, the knee may configure itself to operate as the master device 1112, the ankle may configure itself to operate as a slave device 1114, and the monitor to configure itself as an observation device 1116. In another embodiment of the system 100 that includes only the ankle and the wrist monitor, the ankle may configure itself as the master device 1112 and the monitor as the observation device 1116.

In one embodiment, devices may include a configuration database. The database may contain data relating configurations of the system 1100 with the role of the device. For example, the ankle device may include data indicating that the ankle should configure itself as the slave device 1114 when the system 1100 includes a knee prosthetic, but should configure itself as the master device 1112 in other configurations.

It will be further recognized that in some embodiments, the system 1100 may include one or more of each of the slave device 1114, observation device 1116, and configuration device 1118. Further, in some embodiments, multiple master devices may be configured such that the devices each control groups of prosthetics, e.g., one master device 1112 for a group of arm based mechatronic devices and a second master device 1112 for a group of leg based mechatronic devices. In such an embodiment, the observation device 1116 may display information related to some of the master and slave devices 1112 and 1114. In another embodiment, each observation device 1116 may display information related only to a single master or slave device 1112 or 1114.

The master devices 1112 may communicate over the BDB 1110 to share data or otherwise coordinate operation of the system 1100. In one such embodiment, each of, e.g., arm and leg mechatronic devices may operate as the master device 1112 with respect to a group of devices. For instance, the knee may operate as the master device 1112 with respect to an ankle prosthesis and a shoulder mechatronic device may act as a master device 1112 to an elbow slave device 1114. Continuing with this exemplary embodiment, with respect to knee master device 1112, the ankle may operate as a slave device 1114.

It will be recognized that the devices 1112, 1114, 1116, 1118 as described herein refer to roles or functional descriptions of one mode of operation of a mechatronic device. In some embodiments, a mechatronic device may be a hybrid device, e.g., one that acts as a slave device 1112 under the influence or direction by another master device 1112, but which also maintains a distinct state machine. Further, other embodiments may include mechatronic devices that operate as combinations of any of the devices described herein.

Figure 24:
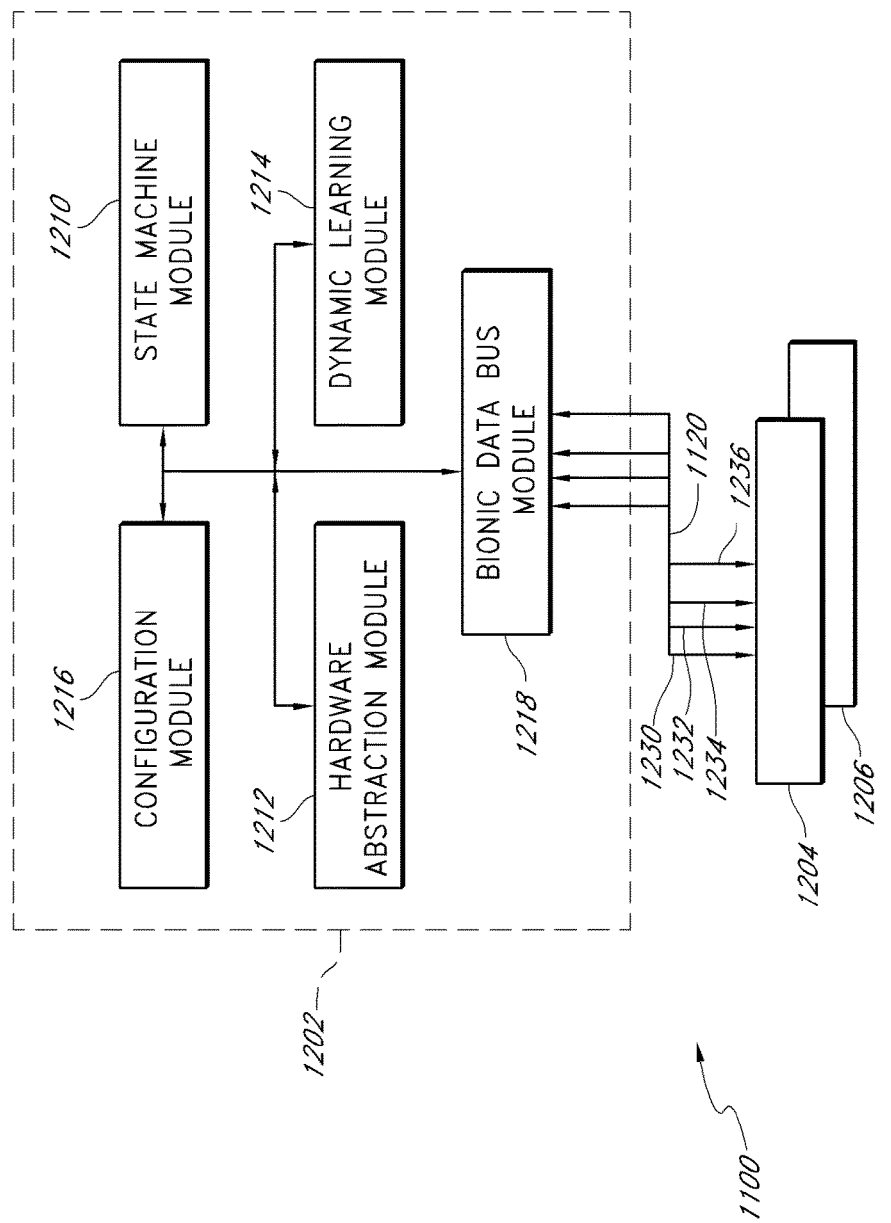
FIG. 24 is a block diagram illustrating in more detail one embodiment of a mechatronic device in communication with additional devices in one embodiment of the system of FIG. 23.

FIG. 24 is a block diagram illustrating in more detail one embodiment of a mechatronic device 1202 in communication with additional devices 1204 and 1206 in one embodiment of the system 1100 via the BDB 1120. The device 1202 may include a processor and memory configured to execute software for controlling the operation of the device.

In one embodiment, the software includes a state machine module 1210, a hardware abstraction module 1212, a dynamic learning module 1214, a configuration module 1216, and a BDB module 1218. It will be recognized that each of the modules 1210, 1212, 1214, 1216, and 1218 may include various sub-routines, procedures, definitional statements and macros. Each of the modules may be separately compiled and linked into a single executable program. The description of each of the modules is used for convenience to describe the functionality of one embodiment of a system. Thus, the processes that are performed by each of the modules may be redistributed to one of the other modules, combined together in a single module, or made available in, for example, a shareable dynamic link library. In some embodiments, the modules may be executed concurrently or in parallel as distinct threads or processes. The modules may be produced using any suitable computer language or environment, including general-purpose languages such as C, C++, Java, or FORTRAN.

Each of the modules 1210, 1212, 1214, 1216, and 1218 may communicate via any suitable method such as are known in the art. In one embodiment, the modules may communicate using shared data structures such as are described in U.S. Patent Publication No. 2005-0283257, filed on Mar. 9, 2005, which was previously incorporated herein. In one embodiment, the shared data structure may include portions that are available for access through the bionic data bus module 1218 to other devices 1204 and 1206 in the system 1100. In such an embodiment, portions of the data in the shared structure may be communicated on the BDB 1120.

In one embodiment, the observation device 1116 may be a personal or server computer system configured to perform diagnostic functions of other devices in the system 1100. In one embodiment, the observation device 1116 may be configured to receive and update the contents of shared data structures, such as described above, through the bionic data bus module 1218.

The state machine module 1210 typically includes high level, application or device specific instructions. The state machine module 1210 may be generally described as having the intelligence of the device. The state machine module 1210 of a particular embodiment of a mechatronic device may be configured to operate as the master device 1112, the slave device 1114, the observation device 1116, or the configuration device 1118 in various embodiments of the system 1100. An embodiment of the state machine module 1210 may be configured so as to be loaded into different mechatronic devices, e.g., different knee hardware, without modification by using the hardware abstraction module 1212 to interface with specific hardware on a particular mechatronic device. One exemplary embodiment of a state machine module 1210 is described in U.S. Pat. No. 6,610,101, filed Mar. 29, 2001, and issued on Aug. 26, 2003, incorporated above.

In one embodiment, portions of the state machine module 1210 may be replaced or augmented to provide customized, e.g., activity based, control of the mechatronic system 1100. For example, software for a specific activity, e.g., bicycling or jogging, may be installed into the state machine module 1210 to improve or customize the functionality of the mechatronic device, e.g., a prosthetic knee, for the specific activity. In one embodiment, the customized control software is installed via download. In one embodiment, the downloaded data may be received from the configuration device 1118. In another embodiment, the master device 1112 may include a network interface over which the customized control software may be received from any other networked computing device. The network interface may comprise a wireless network, e.g., a mobile telephone network, or any other suitable computer network, such as those discussed above in connection with the BDB 1120.

The hardware abstraction module 1212 typically includes low level, hardware specific code that provides a standardized interface to the hardware by other software modules. The hardware abstraction layer 1212 may abstract hardware such as sensors and actuators. The hardware abstraction module 1212 thus allows other software, such as the state machine module 1210 to be reused with different sensors so long as the sensors each provide data that the hardware abstraction module 1212 can represent in a standardized form. For example, a particular sensor may provide data via setting the value of a hardware register. Another sensor for producing equivalent data may signal the processor via an interrupt when the data is updated. The hardware abstraction layer 1212 can be configured to read either sensor and provide the data using a uniform interface so that other software layers do not need to be modified if the particular sensor changes. This may be particularly desirable in the system 100 having multiple mechatronic devices 1202, 1204, 1206. For example, an ankle mechatronic device 1202 may be configured to receive a sensor value, e.g., a knee angle, from different types and models of prosthetic knees 1204. Continuing this example, the hardware abstraction layer 1212 of the ankle device 1202 may provide, in one embodiment, a knee angle that is updated every 5 milliseconds regardless of whether the sensor is configured to be polled by the processor to receive updates or whether the sensor signals the processor via, e.g., an interrupt channel. The hardware abstraction layer 1212 may also be configured to provide the knee angle value that is upsampled or downsampled to a consistent, accurate value regardless of the sensor resolution. For example, the knee angle value may be represented with a value having a resolution of 8 bits, 10 bits or higher. Moreover, the interface to the data may be the same regardless of whether the data is coming from the same mechatronic device 1202 or other mechatronic devices 1204, 1206.

It is to be recognized that some embodiments include mechatronic devices in which the hardware abstraction layer 1212 is configured to communicate with a patient's nervous or muscular system. For example, the actuator may include a muscle. In one embodiment, a sensor includes a nerve of the patient's body.

The dynamic learning module 1214 may include a dynamic learning matrix that updates runtime parameters such as may be used by the state machine module 1212. In one embodiment, the learning module 1214 may adapt runtime parameters to the current pace of movement, particular activity, terrain, etc. One exemplary embodiment of a learning module 1214 is described in U.S. Pat. No. 6,610,101, filed Mar. 29, 2001, and issued on Aug. 26, 2003, incorporated above.

The configuration module 1216 may be configured to store and maintain control parameters. The parameters may be subsequently automatically adjusted by the learning module 1214 or through the configuration device 1118. In one embodiment, the data maintained by the configuration module 1216 is substantially static. The configuration module 1216 may be configured to communicate with the BDB 1120 to the configuration device 1118 to send and receive parameter data. The configuration module 1216 may provide a standard interface over the BDB 1120 to the configuration device 1118. In one embodiment, the configuration module 1216, e.g., of the slave device 1114 is configured to receive parameters through other devices such as the master device 1112. Thus, the components of the system 1100 may be configured together through the configuration device 1118 in communication with the master device 1112, which further communicates parameters to other devices such as devices 1204 and 1206 in the system 1100.

In one embodiment, the abstraction module 1212 controls one or more actuators in a mechatronic system 1100. In one embodiment, this comprises applying damping through an actuator in, e.g., a prosthetic knee. In one embodiment, at least a portion of the abstraction module 1212 executes at a frequency that is different from the execution rate of the state machine or learning modules 1210 and 1214. For example, in one embodiment the low level abstraction module 1212 executes with a period of 1 millisecond (ms) while the higher level code of the state machine executes with a period of 5 ms.

The bionic data bus (BDB) module 1218 is configured to provide data communications between devices in the system 1100 over the BDB 1120. One embodiment of the BDB module 1218 includes a software interface that abstracts or standardizes an interface to the other modules 1210, 1212, 1214, and 1216 for communicating over the BDB 1120 regardless of the particular embodiment of the BDB 1120, e.g., regardless of whether the BDB includes a network or a peripheral bus such as USB.

The BDB module 1218 may provide a layered interface to the BDB 1120. In one embodiment, the layers may correspond to one or more physical channels provided by the BDB 1120. In other embodiments, the layers may correspond to logical channels over the BDB 1120. In one embodiment, the channels provided by the BDB module 1218 includes a state channel 1230, a parameter channel 1232, a sensor channel 1234, and an actuation channel 1236.

The state channel 1230 may be configured to communicate high frequency, low volume state machine data between mechatronic devices. In one embodiment, this data may include data related to the gait cycle of a prosthetic knee. The data may include state data or state change data. For example, in a prosthetic knee, the state change may indicate a change in a gait cycle.

The parameter channel 1232 may be configured to communicate data at intermediate frequencies and volumes to communicate parameter settings between devices, e.g., between the configuration device 1118 and the master device 1112. The parameter channel 1232 may data may include configuration parameters such as are described in U.S. Patent Publication No. 2005-0283257, filed on Mar. 9, 2005, which was previously incorporated herein.

The sensor channel 1234 may be configured to communicate high frequency, low volume sensor data. Sensor data from one device in the system 1100 may thus be shared for use by other devices. This allows for placement of sensors in locations that are not physically located in or adjacent to a particular mechatronic device but which are physically located within or adjacent to another device in the system 1100. Moreover, certain sensors may thus be shared to reduce overall cost of the system 1100. Sensors may include force sensors, battery voltage sensors, or any other sensors as may be incorporated or attached to any mechatronic device.

Another channel may include the actuation channel 1236. The actuation channel 1236 communicates low volume, high frequency data that includes actuator control signals. In one embodiment, the master device 1112 may send actuator control signals over the actuation channel 1236 to control an actuator on the slave device 1114. The data may include data such as position, force, direction, and velocity.

In addition to communicating with other mechatronic devices, other electronic devices, e.g., a remote server computer (not shown), may communicate with the mechatronic device via the BDB 1120. In one embodiment, the remote server may carry out maintenance activities such as diagnosing faults in the mechatronic device. The device 1202 may communicate sensor data, state change data, or other data generated on the device 1202, or devices 1204, 1206 attached to the device 1202 via the BDB 1120.

In one embodiment, a common naming convention is used to identify the data communicated on the channels. In one embodiment, the data is formatted as structured data using the naming convention, such as in extendible markup language (XML). In one embodiment, the naming convention is based on using terminology analogous to anatomical equivalents. For example, in one embodiment, the naming convention includes terminology from the human muscular system for actuator signals and from the human nervous system for sensor signals.

In addition to communicating with other mechatronic devices, other electronic devices, e.g., a remote server computer (not shown), may communicate with the mechatronic device via the BDB 1120. In one embodiment, the remote server may carry out maintenance activities such as diagnosing faults in the mechatronic device. The device 1202 may communicate sensor data, state change data, or other data generated on the device 1202, or devices 1204, 1206 attached to the device 1202 via the BDB 1120.

Figure 25:
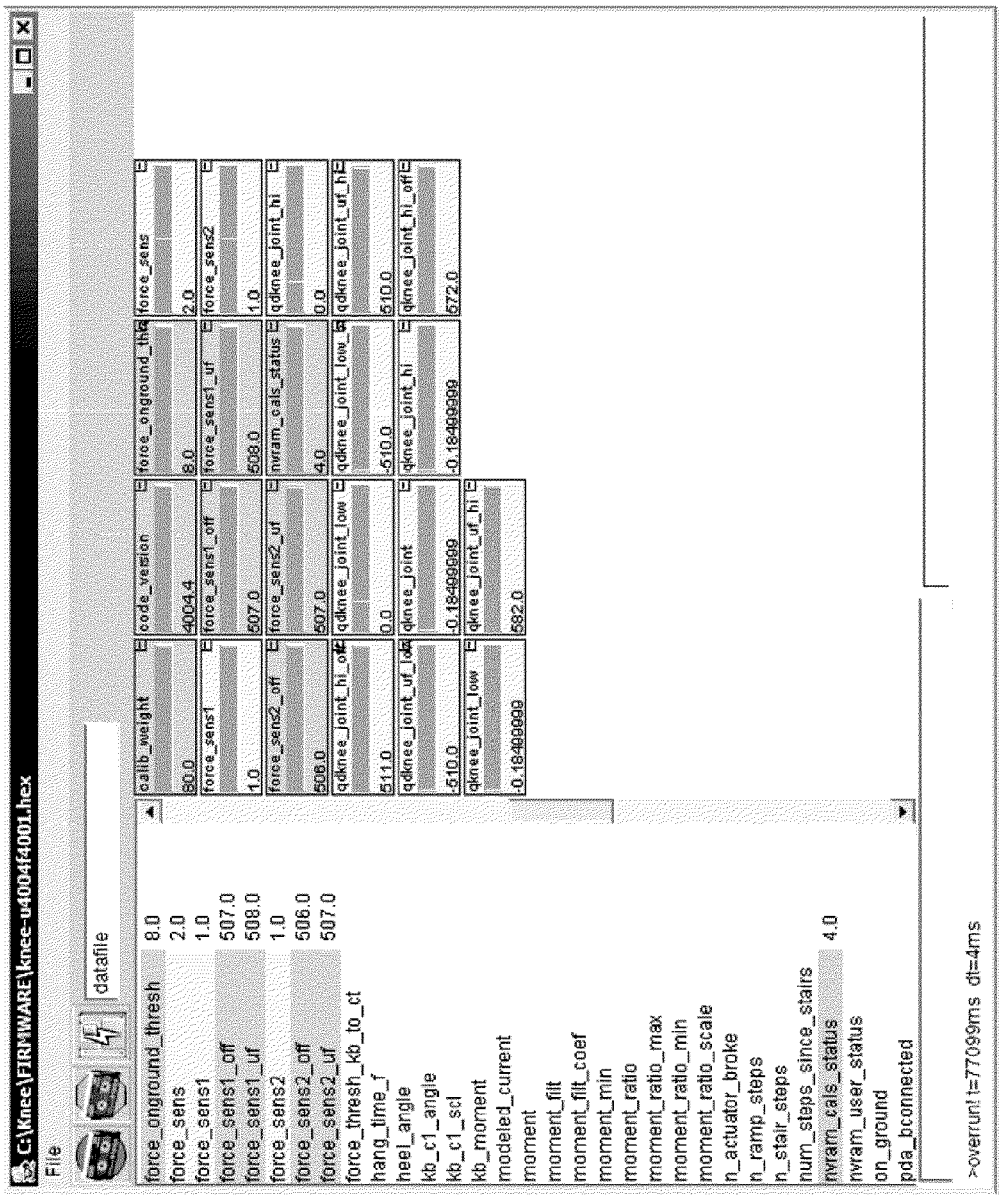
FIG. 25 illustrates a user interface of one embodiment of an instrumentation program for use with a mechatronic device.

In one embodiment, the remote computer includes instrumentation software for maintenance or development of the mechatronic device 1202. FIG. 25 illustrates a user interface of one embodiment of the instrumentation program for use with a prosthetic knee. The left column displays the names of memory locations, registers, or other data that may be monitored on the mechatronic device 1202. In the depicted embodiment, selecting the name of a monitored item causes the value to be displayed. In one embodiment, the displayed value is continuously and automatically updated when new data is received from the device 1202. In one embodiment, the values of the monitored items may be recorded to a file for later analysis. This analysis may include graphical plotting of the data. In one embodiment, the instrumentation program may also send commands to the device 1202, such as to erase data, reset the device 202, and update the software or firmware on the device 1202. In one embodiment, the values of these items may be modified by a user of the instrumentation program. In one embodiment, the instrumentation program may be configured to restrict the values of the updated items to be set within a predetermined range.

FIG. 26A is a schematic block diagram of an exemplary embodiment of the system 1100 that includes a prosthetic knee 1402 and a prosthetic ankle 1404. (See also, e.g., FIG. 30.) When the system 1100 includes an electronically controlled ankle 1404 and an electronically controlled knee 1402 there is a risk of instability if the two "intelligent" components do not share information or otherwise work in a synchronized manner. The knee 1402 may include 3 main sensors, an angle sensor, posterior force sensor (PF) and anterior force sensor (AF). From the signals of PF and AF sensors, the knee 1402 can calculate the moment in a pylon. The knee 1402 can represent the moment as information as to how much the toe is being loaded and how much the heel is being loaded. From the calculation on the values from PF and AF sensors, the knee 1402 is also able to tell if the foot is placed on the ground and with how much force. The force signals together with the angle sensor are evaluated by an algorithm in the state machine module to define the state of the knee 1402 in a high level loop cycling, in one embodiment, every 5 ms. If the signals are incorrect or misinterpreted, the knee 1402 cannot change states or function correctly.

Since the values from the force sensors (bending moment in the knee frame) are translated into toe- and heel load values, the alignment of the foot and especially the angle of the ankle 1404 should be determined. During setup, certain ranges and threshold values may be set for the knee 1402. If the alignment is changed considerably after the initial setup, the knee 1402 can misinterpret the information from the force sensors. The functionality of an electronically adjusted ankle 1404 typically causes just such a change in alignment.

If the ankle 1404 can send information on the angle value to the knee with a sufficiently high frequency, the knee can compensate for the "error" in force signals from the sensors and the whole system 1100 can operate in a more stable way as compared to a non-synchronized system.

The electronic ankle 1404 may also be designed to also fit below-the-knee amputees. In such a mode of use, the ankle 1404 does not need the extra information from a "colleague" component. The extra information that the knee 1402 is able to communicate may however simplify the design of the ankle for use by above-the-knee amputees.

In addition, the use of data from the knee 1402 by the ankle 1404 can provide additional functionality to the system 1100. For example, the angle value of the ankle 1402 can be made accessible to the knee 1404 through the sensor channel 1232 of the BDB 1120. Also if the ankle is offset by some degree (for use with high heels, for example), the knee 1402 may use the information to further compensate for the force sensor measurements. The offset value can be communicated over the parameter channel 1232.

In one embodiment, the ankle may include a prosthetic or orthotic foot, similar to embodiments disclosed in U.S. patent application Ser. No. 11/346,600, filed on Feb. 2, 2006, titled "SENSING SYSTEMS AND METHODS FOR MONITORING GAIT DYNAMICS," and incorporated by reference in its entirety, that is configured to make and provide toe load and heal load measurements over the BDB 1120. In another embodiment, the ankle may include a prosthetic or orthotic foot, similar to embodiments disclosed in U.S. patent application Ser. No. 10/742,455, filed on Dec. 18, 2003, titled "Prosthetic foot with rocker member," and incorporated by reference in its entirety, that is configured to make and provide an angle measurement over the BDB 1120.

FIG. 26B is a schematic block diagram of an exemplary embodiment of the system of FIG. 23 that includes a prosthetic knee 1402 and a prosthetic foot 1406. In one embodiment, the knee 1402 and the ankle 1404 each include a data communications or network interface such as an RS-232 port that are in communication with each other to define the BDB 1120. In another embodiment, the BDB 1120 may be implemented via RS-485 ports on each of the devices 1402 and 1406. In one embodiment, the prosthetic foot 1406 includes a joint that allows the foot to adjust to different grades of slopes. As a result, the response from the foot 1406 will differ from prosthetic feet with a fixed ankle. In one embodiment, the knee 1402 is controlled based on force measurements that are translated into bending moments. From the moment values, the knee 1402 manages state changes and adjusts the resistance of the knee based on whether the knee 1402 is on level ground, on different grades of slopes, or on stairs.

In one embodiment, the knee 1402 may detect that the user is walking on a sloped surface based on changes in force and moment. Due to bending of the jointed foot 1406, the foot 1406 may adjust to a slope so that the knee 1402 does not receive force measurements that are consistent with walking on the slope. Thus, the knee 1402 may act as if the user is walking on level ground when the user is actually descending or ascending a ramp. In one embodiment, the foot 1406 may communicate its joint angle to the knee 1402 when the angle has changed. In other embodiments, the foot 1406 may communicate the angle to the knee at a predetermined rate or when the angle changes by a threshold amount. In one embodiment, the knee 1402 may request the data from the foot 1406 either at intervals or response to particular events such as state changes. The knee 1402 may then use the angle value to correct the moment calculations (e.g., through a proportional calculation as a function of the angle). In one embodiment, the data communicated from the foot 1406 to the knee 1402 may include state machine data. The state machine data may be used by the control system of the knee 1402 to coordinate movement with the foot 1406 and to better identify the proper control response based on the additional information from the foot 1406, e.g., correcting force sensor readings when the joint of the foot 1406 is bent.

In certain embodiments, the jointed foot 1406 may be triggered to adjust its angle after the user has completed, for example, three strides. In other embodiments, the jointed foot 1406 may be triggered to adjust its angle after more than three strides. In addition, the ankle may be triggered to perform a toe lift function when the user has completed three strides and has reached a particular speed of, for example, at least about 0.55 meters per second. A typical transtibial device will require a greater number of strides in order to stabilize the gait pattern of the device user due to the larger range of mobility between transtibial users. In contrast, a transfemoral user, who has both a prosthetic knee 1402 and a jointed foot 1406, can have a narrower range of motion. As a result, three strides provides sufficient information to the device to initiate toe lift and an associated predetermined gait pattern. This faster processing time is beneficial to a prosthetic user as it increases the devices adaptability to changing environments. While the transfemoral device may initiate toe lift after three strides in certain embodiments, in other embodiments, the trigger may be initiated after two strides to five strides and/or when the user has reached a particular speed of between about 0.40 m/s and 0.60 m/s.

As discussed above, in certain embodiments, the knee 1402 maintains force measurements consistent with walking on level ground. The foot unit 1406 adjusts its angle in order to compensate for the slope. In certain embodiments, the foot unit 1406 coupled to a knee unit 1402 may have a greater range of motion than a foot unit 1406 that is coupled to a physiological knee because movement of the prosthetic knee 1402 can be more predictable due to the knee 1402 having fewer degrees of freedom than a physiological knee. For example, the foot unit 1406 coupled to a prosthetic knee 1402 may be able to perform toe lift down to a gradient of about −10 degrees from level-ground, while a foot unit 1402 coupled to a physiological knee may only be able to perform toe lift down to a gradient of about −6.5 degrees from level-ground.

Data may be communicated between the foot 1406 and the knee 1402 using any suitable protocol such as discussed above with reference to the BDB in FIG. 23. For example, in one embodiment, sensor and control data may be communicated as a string of characters over the RS-232 link. In one embodiment, in each program cycle of the knee 1402, the knee reads the serial port, parses the string and filters out the angle value. The angle value is then translated into a correction value for a slope detection routine.

In another embodiment, data may be communicated over the RS-232 layer by a suitable link layer protocol such as the High Level Link Control (HDLC) protocol. In other embodiments, suitable higher level protocols may be used. In one embodiment, the two RS-232 ports may be connected via simple wire interface.

In one embodiment, the knee 1402 may operate as the master device 1112 that receives sensor data from the foot 1406 and use that data to generate control signals that are communicated back to the foot 1406. In such an embodiment, the additional sensor data from the foot 1406 may be used to provide control that is more robust and enable the knee 1402 to be better able to anticipate or otherwise manage state changes. Moreover, the additional sensor data of the knee can be used to extend or improve the control of the foot 1406. For example, the load sensors of the knee 1402 may be able to detect a rapid toe off signal that can indicate initial steps onto stairs. The control system of the foot 1406 may be configured to use this data to anticipate and better detect state changes such as stair ascent or descent. In another example, the load sensors of the foot 1406 may be able to detect a change in incline or decline and alert the master device 1112 to adjust accordingly.

In one embodiment, the foot 1406 and the knee 1402 may also be configured to share a power source. In such an embodiment, the master device 1112, e.g., the knee, may coordinate power management for both devices. In one embodiment, the foot 1406 and knee 1402 may be designed specifically to operate together. However, in other embodiments, any knee 1402 and foot 1406 that include compatible mechanical and communication interfaces may form the system 1100.

FIG. 26C is a schematic block diagram of another exemplary embodiment of the system of FIG. 23 that includes a prosthetic knee 1402, a prosthetic foot 1406, and a master device 1408 operating as a master device 1112. The master device 1408 may include any electronic device configured to receive sensor data from each of the knee 1402 and the foot 1406 and provide control signals to the knee 1402 and the foot 1406 based on that sensor data.

FIG. 26D is a schematic block diagram of another exemplary embodiment of the system of FIG. 23 that includes a prosthetic knee 1402 and a prosthetic foot 1406 in which the prosthetic foot 1406 operates as the master device 1112. In such an embodiment, the controller of the foot 1406 may include one or more state machines for controlling both devices.

Figure 27:
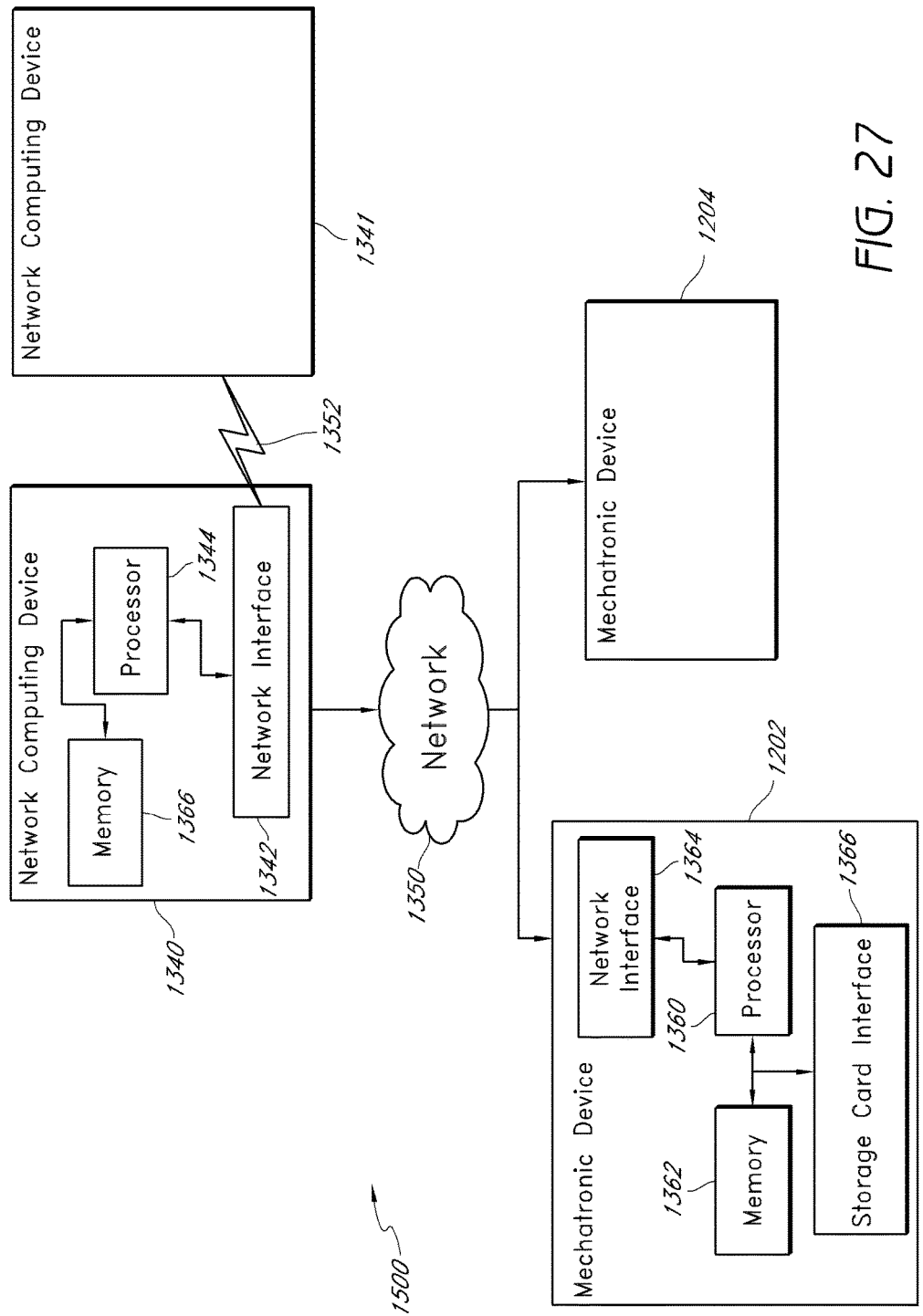
FIG. 27 is a block diagram illustrating one embodiment of a system including mechatronic devices in communication with personal and network computing devices.

FIG. 27 is a block diagram that depicts one embodiment of a system 1500 for communicating with a pair of mechatronic devices 1202 and 1204. In the depicted embodiment, the system 1500 includes a single network computing device 1340 in communication with the mechatronic devices 1202 and 1204 via a data communications network 1350. Other embodiments include only a single mechatronic device 1202, or more than two mechatronic devices. In one embodiment, the system 1500 includes additional network computing devices 1341 that are also in communication with the network computing device 1340 via a network 1352. In one embodiment, the mechatronic devices 1202 and 1204 are configured to communicate with the network computing device 1340 to send and receive configuration and calibration data. In one embodiment, the mechatronic devices 1202 and 1204 are configured to communicate with the network computing device 1340 to receive executable instructions to augment or replace portions, or all, of one or more of the state machine module 1210, the hardware abstraction module 1212, the dynamic learning module 1214, a configuration module 1216, the BDB module 1218, or any other suitable software module of the mechatronic device 1202.

In one embodiment, the network computing device 1340 includes a network interface 1342 in communication with a processor 1344 and a memory 1346. The network computing device 340 may include a server computer, a personal computer, or a mobile computer such as a laptop computer. In one embodiment, the network computing device 1340 includes a personal digital assistant. In another embodiment, the network computing device 1340 includes a mobile telephone.

The network interface 1342 provides network connectivity to one or more computing devices, including the mechatronic devices 1202 and 1204, via the networks 1350 and 1352. In one embodiment, the network interface 1344 to the networks 1350 and 1352 includes one or more of, for example, a remote modem, Ethernet (IEEE 802.3), Token Ring (IEEE 802.5), Fiber Distributed Datalink Interface (FDDI) Asynchronous Transfer Mode (ATM), Wireless Ethernet (IEEE 802.11), Bluetooth (IEEE 802.15.1), or infrared interfaces including IRDA. The network 1350 may include networks such as the Internet, an intranet, Local Area Networks (LAN) or Wide Area Networks (WAN). As used herein, the networks 1350 and 1352 may include network variations such as the public Internet, a private network within the Internet, a secure network within the Internet, a private network, a public network, a value-added network, an intranet, and the like. In one embodiment, the network 1350 includes the network 1352.

The processor 1344 may be any suitable general purpose single- or multi-chip microprocessor such as an ARM, Pentium®, Pentium II®, Pentium III®, Pentium IV®, Pentium® Pro, an 8051, a MIPS®, a Power PC®, an ALPHA®, or any other suitable processor. In addition, the processor 1344 may comprise any suitable special purpose microprocessor such as a digital signal processor or a programmable gate array.

The memory 1346 may include volatile components, such as, for example, DRAM or SRAM. The memory 1346 may also include non-volatile components, such as, for example, memory or disk based storage. In one embodiment, the network computing device 1340 includes a server and the memory 1346 includes disk base storage. In one embodiment, the disk based storage includes a file server.

In one embodiment, the mechatronic device 1202 includes a storage card interface 1366 to a removably connected memory. The storage card interface 1366 may include an interface to a removable storage card that includes semiconductor storage (chips), for example, Random Access Memory (RAM) or various forms of Read Only Memory (ROM), that are removably connected to the processor 1344. Removably connected memory may include memory on any standardized or proprietary device such as a memory card, a secure digital memory card, a memory stick, or any other suitable removable memory device. In one embodiment, the storage card interface 1400 is configured to interface the processor solid state persistent memory such as FLASH memory or magnetoresistance RAM (MRAM). In one embodiment, the memory 1104 includes a disk drive, e.g., a magnetic, optical, or magneto-optical drive.

In one embodiment, each of the mechatronic devices 1202 and 1204, includes a processor 1360 connected to a memory 1362 and a network interface 1364. The processor 1360 may include any suitable processor including those discussed above with respect to the processor 1344. The memory 1362 may include any suitable memory such as discussed above with respect to the memory 1346. The network interface 1364 places the processor 1360 in communication with the network 1350. The network interface 1364 may include any suitable network interface, including those discussed above with respect to the network interface 1342.

Figure 28:
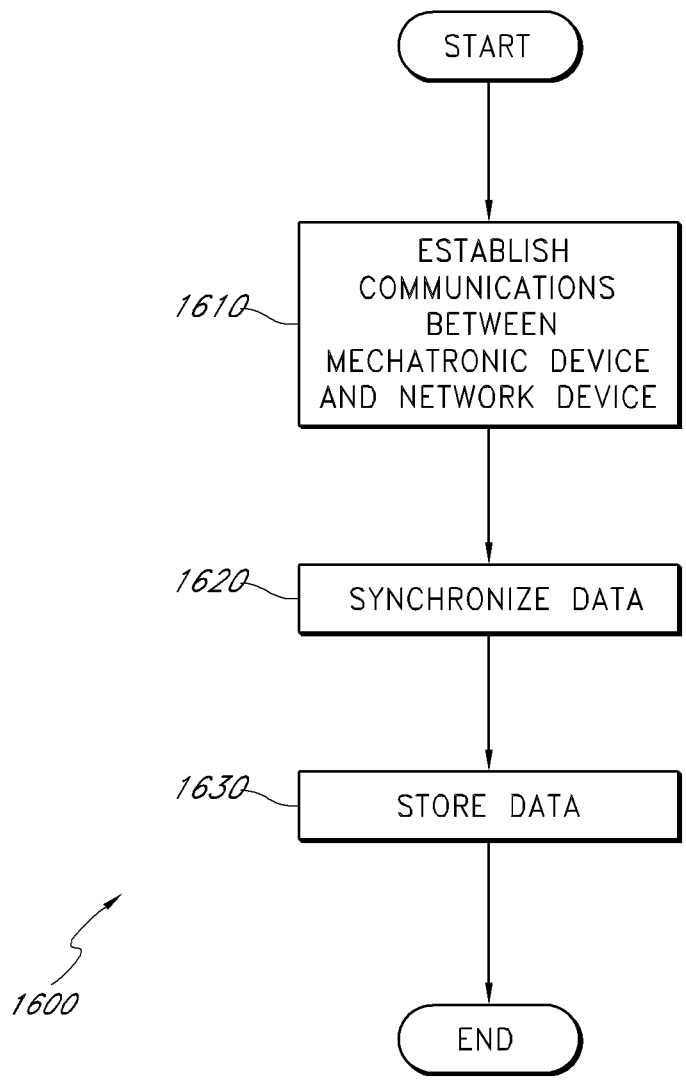
FIG. 28 is a flowchart illustrating one embodiment of a method of synchronizing configuration or calibration data of the mechatronic device with the network computing device.

FIG. 28 is a flowchart illustrating one embodiment of a method 1600 of synchronizing configuration or calibration data of the mechatronic device with the network computing device 1340 of FIG. 27. Configuration data may include data that is entered by a prosthetist, determined based on predetermined parameters, such as the height of a user of the mechatronic device, selected based on experience or preferences of the user of the mechatronic device 1202, or selected by a designer or manufacturer of the mechatronic device, that affects the control system of the mechatronic device 1202. Calibration data may include data that is determined by the control system of the mechatronic during operation of the mechatronic device 1202. Such data may also be generally referred to as control data. The method 1600 begins at a block 1610 in which the mechatronic device 1202 establishes communications with the network computing device 1340. Entry or examination of such data could be made through a screen display such as the one shown in FIG. 25.

Next at a block 1620, the mechatronic device 1202 synchronizes one or more settings with the network computing device 1340 of FIG. 27. In one embodiment, the mechatronic device 1202 receives configuration or calibration information related to a user of the particular mechatronic device 1202. In another embodiment, the mechatronic device 1202 sends configuration or calibration data to the network computing device 1340. In one embodiment, the synchronized configuration and calibration data includes any of the data, discussed above, that is sent over the BDB 1120. In addition, the synchronized data may include any other configuration or calibration data used by the mechatronic device 1120.

In one embodiment, synchronizing the data includes determining the differences between data on the mechatronic device 1202 and data associated with the particular mechatronic device 1202 on the network computing device 1340, and sending that data from one device to the other. In one embodiment, the network computing device 1340 stores the data associated with the mechatronic device 1202 in a database in association with data identifying the particular mechatronic device, e.g., a serial number. In one embodiment, when the particular mechatronic device 1202 is synchronized again, the network computing device 1340 determines the differences in the data based on the data in the database. In one embodiment, after determining which control data is different, the mechatronic device 1202 sends control data to the network computing device 1340 that overwrites control data associated with the mechatronic device 1202. In another embodiment, the network computing device 1340 sends control data to the mechatronic device 1202 that overwrites such data on the mechatronic device. In one embodiment, some data is sent both ways for overwriting. Whether the control data is sent to or from the mechatronic device 1202 may be based on one or more methods. For example, in one embodiment, time stamps are associated with the data so that the newest data associated with a particular item of control data is saved on both the mechatronic device 1202 and the network computing device 1340. In other embodiments, predetermined rules regarding particular items of control data determine how the data is synchronized. In one embodiment, a selection by the user of the device, or a selection by a prosthetist determines in which data particular items of control data are synchronized. In one embodiment, a new mechatronic device 1202 receives initial control data from a database associated with the network computing device 1340 that stores initial data or overwrites any existing data on the mechatronic device 1202.

In one embodiment, the network computing device 1340 acts as a conduit to send and receive the configuration or calibration data to another network computing device 1341 that stores the data. In one embodiment, the network computing device 1340 is a PDA or mobile telephone that communicates with the mechatronic device 1202 via a short range network and relays that data to the network computing device 1341. In one such embodiment, the network computing device 1341 includes a server computer. Thus, the mechatronic device 1202 may synchronize configuration and calibration data with one or both of the network computing devices 1340 and 1341.

Next at a block 1630, the mechatronic device 1202 stores any received data. Also, or alternatively, the network computing devices 1340 and 1341 store any received data. In one embodiment, one or more of the devices 1202, 1340, or 1341 also store data related to the synchronization, e.g., a timestamp or data identifying the devices or data involved in the synchronization. In one embodiment, the network computing device 1340 or 1341 stores the data in a database in association with the mechatronic device. Returning to FIG. 28, the method 1600 proceeds to an end state.

Figure 29:
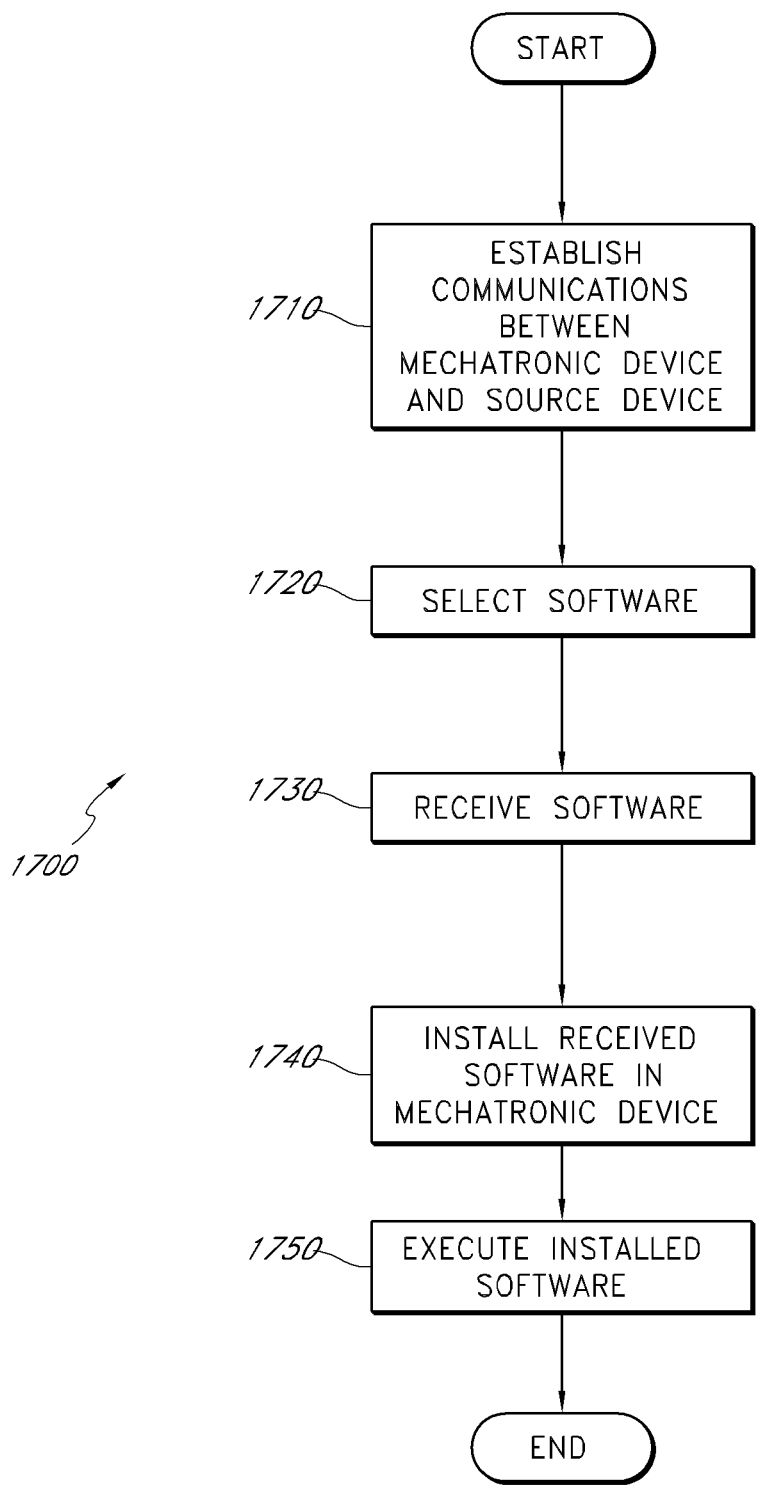
FIG. 29 is a flowchart illustrating one embodiment of a method of replacing or augmenting software on the mechatronic device.

FIG. 29 is a flowchart illustrating one embodiment of a method 1700 of installing, replacing, augmenting, or deinstalling software on the mechatronic device. The method 1700 begins at a block 1710 in which the mechatronic device 1202 establishes communication with a source device containing software configured to execute on the mechatronic device 1202. In one embodiment, the source device includes the network computing device 1340. In such an embodiment, the mechatronic device 1202 establishes communications with the network computing device 1340 via the network 1350. In another embodiment, the source device also includes the network computing device 1341. In such an embodiment, the mechatronic device establishes communications with the network computing device 1341 through the networks 1350 and 1351 via the network computing device 1340. In one embodiment, the source device includes another mechatronic device. In another embodiment, the source device includes a storage card in communication with the storage card interface 1366. The software could be low level firmware and/or high level software, for example.

Moving to a block 1720, the mechatronic device 1202 or the user of the device 1202 selects software to be installed thereon. In one embodiment, the user selects from a list of software adapted to various activities, e.g., hiking, biking, or jogging. In one embodiment, the list is displayed on a user interface associated with the network computing device 1340. In one embodiment, the user interface includes a web browser. In one such embodiment, the user interface receives the list from the network computing device 1341.

Proceeding to a block 1730, the mechatronic device 1202 receives the software from the source device. In one embodiment, receiving the software includes transferring then software over the network 1350. In another embodiment, receiving the software includes having a storage card installed in the storage card interface 1366.

Next at a block 1740, the mechatronic device 1202 installs the software for execution. Installing the software may include saving the software to a portion of the memory 1362, updating pointers or jump tables in the memory 1362 to replace or augment previously installed software, or storing a record of the software installation. In one embodiment, the record includes sufficient data to remove the newly installed software. In one embodiment, the mechatronic device 1202 saves the received software to its memory 1362. In another embodiment, the mechatronic device 1202 executes the new software directly from a storage card.

Moving to a block 1750, the mechatronic device executes the new software. The new software may replace all or a portion of one or more of the state machine module 1210, the hardware abstraction module 1212, the dynamic learning module 1214, a configuration module 1216, the BDB module 1218, or any other suitable software module of the mechatronic device 1202. The new software may include software updates to fix bugs, improve performance, or provide additional features. In one embodiment, the new software may include instructions for controlling the mechatronic device 1202 to perform one or more specific activities such as hiking, biking, swimming, jogging, throwing, jumping, or for movement over a particular type of terrain.

Typically, prosthetic and orthotic devices are designed to operate without taking into account the operation of other prosthetic and/or orthotic devices. Prosthetic and/or orthotic components, however, affect the function of other prosthetic and/or orthotic components. For example, a prosthetic foot or ankle joint affects the function of a prosthetic knee. Furthermore, prosthetic components are typically designed to replicate the function of the limb being replaced, and orthotic components are typically designed to enhance the function of the limb being assisted. For example, a prosthetic foot functions to replace the function of a missing or amputated foot.

Different prosthetic and orthotic devices perform differently in different situations and environments. Some prosthetic and orthotic devices include, for example, sensors, control systems and/or actuators. These devices may have different functions than other prosthetic and orthotic devices. For example, some prosthetic devices may be able to detect gradients, to adapt to variable imposed accelerations, and so forth.

Some prosthetic and/or orthotic devices may be combined in a way to enhance the functionality of one or more of the devices. For example, a prosthetic knee may have particular working angles based on level ground walking. Most prosthetic knee users, however, will encounter diverse terrains of different gradients, such as inclined and declined slopes. If a prosthetic knee is combined with a terrain active ankle, the prosthetic knee may be able to operate at a more comfortable working angle, such as for example for level ground walking, because the ankle device has adapted to, for example, an inclined or declined slope, which may obviate the advantages in adapting the prosthetic knee for sloped gradients.

As another example, a prosthetic knee may not provide for ground clearance with toe lift as would a healthy knee. In order to compensate, prosthetic knee users may move their prosthetic legs in a different manner than a healthy knee. Moreover, prosthetic knee devices may also be programmed to move differently than a healthy knee in order to compensate for the lack of toe lift. Moving in a different manner, however, may be uncomfortable to a prosthetic knee user. If a prosthetic knee is combined with an ankle prosthetic capable of toe lift during swing, it may be possible to move the prosthetic knee in a manner similar to a healthy knee.

Thus, prosthetic and orthotic devices may not only replace missing or amputated body parts, but may also improve the function of another prosthetic and/or orthotic component. Furthermore, a prosthetic and orthotic device may also improve the functionality of natural physiological condition such as, for example, a weak knee, or a weak hip.

In some embodiments, a prosthetic device has a primary function of replacing a lost body part and also a secondary function of improving the function of one or more prosthetic components. Rather than merely affecting the function of another prosthetic or orthotic device or of a physiological condition, embodiments improve such functions. In some embodiments, sensing and actuating systems that replace the function of a missing or amputated body part may also provide the function of improving one or more other prosthetic and/or orthotic devices, as well as one or more other physiological conditions. For example, in some embodiments, a prosthetic device can improve how another device, or body part, performs walking on level ground, ascending and descending stairs, wearing high heels, ascending inclines and descending declines, and walking with variations in stride length, on variable terrain, and with improved comfort and stability of the user.

In some embodiments, improving the function of another prosthetic device may be accomplished in addition to synchronizing and/or coordinating multiple prosthetic and/or orthotic devices. In other embodiments, improving the function of another prosthetic device may be accomplished without synchronizing and/or coordinating multiple prosthetic and/or orthotic devices. The goal of the present invention is not only to coordinate two or more coupled prosthetic devices such that they would perform their necessary tasks, but also to provide sensing and actuating systems, which would improve the function of other operatively coupled prosthetic devices and provide the most natural movement.

Figure 30:
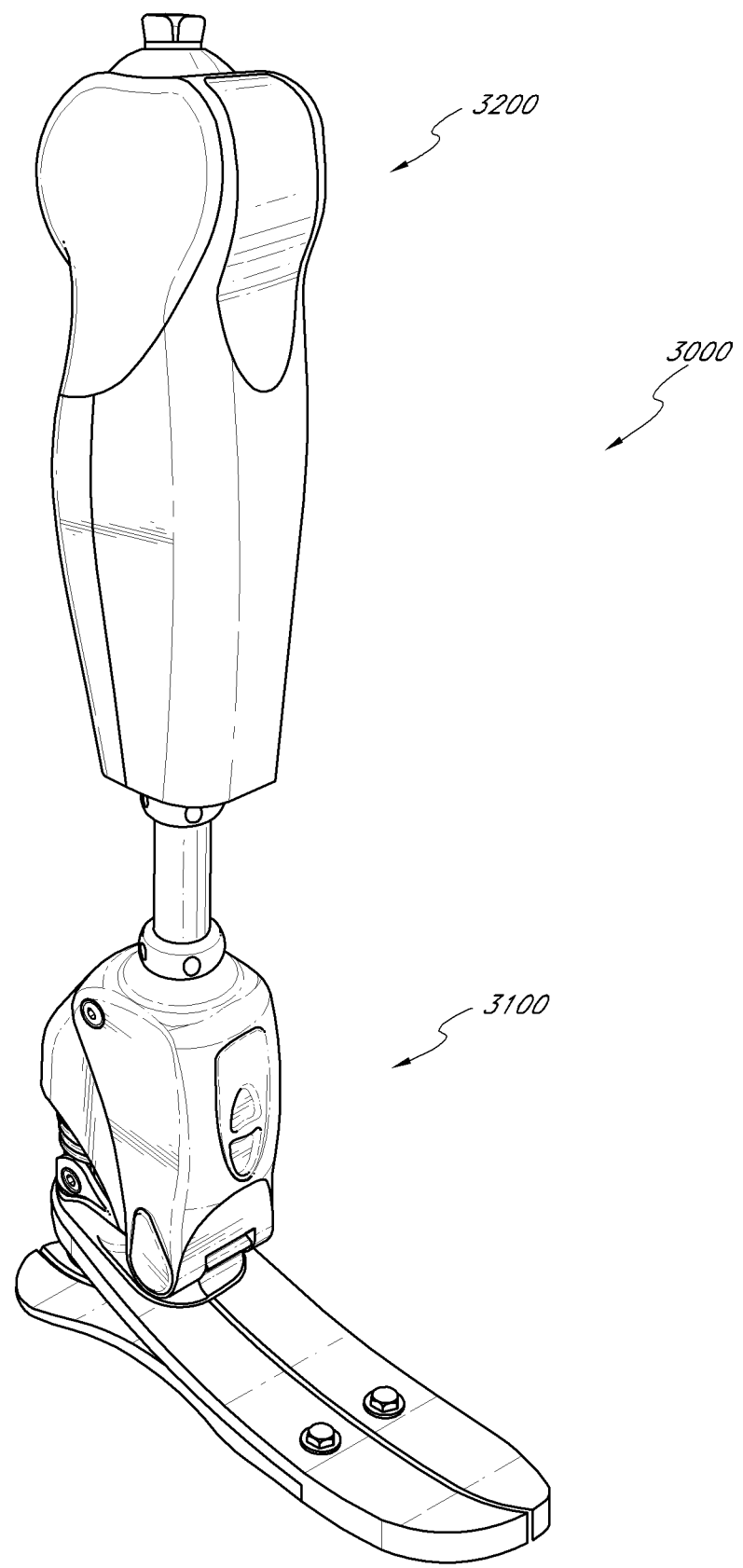
FIG. 30 is a perspective view of a transfemoral prosthesis having an ankle-motion-controlled foot unit and an actuated knee unit according to one embodiment of the invention.

One example of a prosthetic device whose function may be improved when coupled to another prosthetic device is a prosthetic ankle that may be used with a prosthetic knee. One example of a prosthetic knee that may be used in this configuration is the Total Knee, described in U.S. Pat. No. 5,314,498, which is herein incorporated by reference in its entirety. FIG. 30 illustrates one embodiment of a transfemoral device 3000 having an actively adjustable prosthetic ankle 3100 and an actively adjustable prosthetic knee 3200. In certain embodiments, as described in this specification, the illustrated ankle 3100 adjusts to the angle of the incline or decline so that the actuated knee 3200 can operate more closely to ground level walking.

In some embodiments, a prosthetic ankle device monitors the movement and/or position of the device over a number of steps before adjusting the device (such as adjusting the angle of the foot with respect to a neutral position when the foot contacts the ground) in response to a particular terrain. Although in some embodiments the number of steps recorded is fixed, in other embodiments the number can be determined dynamically. In some embodiments, a transfemoral prosthetic ankle device may benefit a transfemoral user (someone who uses a prosthetic knee) by adapting to changing terrain conditions more quickly than it would for a transtibial user (someone with a healthy knee, but who uses a prosthetic ankle). For example, a transfemoral device may monitor about three strides before automatically adapting to the particular terrain (e.g., by performing a toe lift function), whereas a transtibial device may need to monitor around five strides before doing the same. In certain embodiments, this difference is due to the transfemoral user's movements being more predictable (e.g., within a defined range) and having fewer degrees of freedom than a transtibial user's movements. Such calibrations may accommodate transfemoral users who are more sensitive to changes in terrain than transtibial users.

In some embodiments, a prosthetic ankle device has a particular speed of movement at which the device provides for toe lift or toe clearance. In some embodiments, a transfemoral prosthetic ankle device may be improved by adjusting the particular speed at which the device provides for toe lift during, for example, a swing phase of gait. A transfemoral user may have a slower gait speed and more limited movement. A decreased threshold for providing toe lift may provide the transfemoral user with a more comfortable and natural walking experience. For example, in certain embodiments, the toe lift of the combined actuated prosthetic knee and ankle-motion controlled foot unit is triggered after three strides of the prosthetic system, after reaching a particular speed of about 0.55 meters per second. In other embodiments, the toe lift of a transfemoral device is be triggered at between about 0.40 m/s and about 0.60 m/s.

In some embodiments, a prosthetic ankle device may allow for a transition into a relaxed mode. In some embodiments, a transfemoral device may benefit a transfemoral user by disallowing a relaxed mode because, for example, it is more difficult for a transfemoral user (due to insufficient knee control, for example) to position the prosthetic device by, for example, extending the foot portion, so as to enter a relaxed mode. In other embodiments, a transfemoral device may be improved by modifying a relaxed mode to allow a user to enter the relaxed mode by physically placing the prosthetic device into a relaxed position. For example, a user may lift the prosthetic knee into a sitting position characterized by a bent knee joint with the ankle approximately directly below the knee joint, which may trigger a relaxed mode. This may be an option for a transfemoral user who would not normally be able to position a leg into a relaxed position without physically moving it.

In some embodiments, a prosthetic ankle device may provide a learn mode for calibrating the device to a user's specific gait. In some embodiments, a learn mode may benefit a transfemoral user by, for example, utilizing the learn mode from the beginning to calibrate, by way of example, for the gait of a transfemoral prosthetic device user.

In some embodiments, a prosthetic ankle device may provide a decline angle at which toe clearance is no longer provided. In some embodiments, a transfemoral prosthetic ankle device may benefit a transfemoral user by increasing the angle at which toe clearance is provided. Transfemoral users may rely more on toe clearance functions, making them more stable, than transtibial users whose natural knee often provides a greater degree of freedom than a prosthetic knee. During decline at certain angles, a transtibial user may not benefit from toe clearance because they walk off the edge. Thus, transfemoral prosthetic ankle devices may benefit transfemoral users by providing for toe clearance at certain decline angles at which a transtibial user would prefer to have the ankle locked. For example, a transtibial user, using an ankle-motion controlled prosthetic foot as herein described, can have, in certain embodiments, toe lift up down to a gradient of about −4 to −8 degrees, more preferably about −6.5 degrees from level-ground. In contrast, a transfemoral user may have toe lift down to a gradient of about −8 to −12 degrees, more preferably about −10 degrees from level-ground.

In some embodiments, a prosthetic ankle device is capable of making adjustments for ascending and/or descending stairs. In some embodiments, a transfemoral prosthetic ankle device may benefit a transfemoral user by disabling a stairs mode. A transfemoral user may not benefit from the adjustments made for stairs provided to a transtibial user, and may have a more comfortable and natural gait by disabling a stairs mode.

It is to be appreciated that depending on the embodiment, certain acts or events of a method described herein can be performed in a different sequence, may be added, merged, or left out all together (e.g., not all described acts or events are necessary for the practice of the method). Moreover, in certain embodiments, acts or events may be performed concurrently, e.g., through multi-threaded processing, interrupt processing, or multiple processors, rather than sequentially.

While certain embodiments of the inventions have been described, these embodiments have been presented by way of example only, and are not intended to limit the scope of the inventions. Indeed, the novel methods and systems described herein may be embodied in a variety of other forms. For example, the foregoing may be applied to the motion-control of joints other than the ankle, such as a knee or a shoulder. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

I claim:

1. A transfemoral prosthetic device associated with a limb, comprising:
   a foot unit;
   a tibial member pivotally attached to the foot unit to define an ankle joint;
   a femoral member pivotally attached relative to the tibial member to define a knee joint;
   an actuator operatively coupled to the ankle joint and configured to actively adjust an ankle-angle between the tibial member and the foot unit during at least a portion of a swing phase of a gait cycle;
   at least one sensor disposed on the transfemoral prosthetic device and configured to generate data indicative of at least one of position or movement of the transfemoral prosthetic device during a gait of a user; and
   a processor communicatively coupled to the at least one sensor and configured to:
      receive said generated data,
      determine the ankle-angle of the transfemoral prosthetic device and that the user is moving up an incline or down a decline based at least in part on said generated data,
      determine ankle-angle adjustments based at least in part on determining that the user is moving up the incline or down the decline and on said determined ankle-angle of the transfemoral prosthetic device satisfying an ankle-angle threshold, wherein the ankle-angle adjustments comprise a first ankle-angle adjustment and a second ankle-angle adjustment, and wherein the first ankle-angle adjustment is used for ankle angle amounts in between a first threshold and a second threshold and the second ankle-angle adjustment is used for ankle angle amounts beyond the second threshold,
      generate a control signal based at least in part on said determined ankle-angle adjustments of the transfemoral prosthetic device, and
      actively adjust the ankle-angle of the transfemoral prosthetic device by actuating the at least one actuator operatively coupled to the ankle joint during at least a portion of the swing phase of the gait cycle based at least in part on said generated control signal.

2. The transfemoral prosthetic device of claim 1, wherein the actuator operatively coupled to the ankle joint is a first actuator, and the knee joint comprises a second actuator configured to affect a knee angle between the tibial member and the femoral member.

3. The transfemoral prosthetic device of claim 2, wherein the processor is configured to actuate the first actuator to affect the foot unit relative to the tibial member in a manner mimicking movement of a healthy ankle.

4. The transfemoral prosthetic device of claim 2, wherein the processor is configured to actuate the second actuator to affect the femoral member relative to the tibial member such that the knee angle moves in a manner mimicking movement of a healthy knee.

5. The transfemoral prosthetic device of claim 2, wherein the second actuator is configured to affect the angle between the femoral member and the tibial member consistent with a healthy knee walking on level ground.

6. The transfemoral prosthetic device of claim 2, wherein the second actuator is configured to affect the knee angle between the tibial member and the femoral member consistent with a healthy knee walking on level ground while actually walking on a sloped surface.

7. The transfemoral prosthetic device of claim 6, wherein the at least one sensor is configured to monitor a load on the knee joint, and wherein the knee maintains a load consistent with a healthy knee walking on level ground while actually walking on the sloped surface.

8. The transfemoral prosthetic device of claim 2, wherein the second actuator is configured to actively adjust the knee angle between the tibial member and the femoral member.

9. The transfemoral prosthetic device of claim 2, wherein the first actuator is configured to affect the ankle-angle between the tibial member and the foot and the second actuator is configured to affect the knee angle between the femoral member and the tibial member to reduce a load on a physiological member that is coupled with the transfemoral prosthetic device.

10. The transfemoral prosthetic device of claim 2, wherein the first actuator is configured to actively adjust the ankle-angle between the tibial member and the foot unit in a toe lift after about three strides of a user of the transfemoral prosthetic device.

11. The transfemoral prosthetic device of claim 2, wherein the first actuator is configured to affect the ankle-angle between the tibial member and the foot unit during a stance phase of the gait cycle.

12. The transfemoral prosthetic device of claim 11, wherein the first actuator is configured to actively adjust the ankle-angle between the tibial member and the foot unit during the stance phase of the gait cycle.

13. The transfemoral prosthetic device of claim 2, wherein the second actuator is configured to affect the knee angle between the femoral member and the tibial member during the swing phase of the gait cycle.

14. The transfemoral prosthetic device of claim 1, wherein the at least one sensor comprises an accelerometer and a load sensor.

15. The transfemoral prosthetic device of claim 1, wherein the processor is configured to process the data from the at least one sensor to dynamically determine a gait cycle phase.

16. The transfemoral prosthetic device of claim 1, wherein the actuator is configured to actively adjust the ankle-angle between the tibial member and the foot unit in a toe lift after about three strides of the user of the transfemoral prosthetic device.

17. The transfemoral prosthetic device of claim 1, wherein the actuator is configured to affect the ankle-angle between the tibial member and the foot unit: during a stance phase of the gait cycle.

18. The transfemoral prosthetic device of claim 17, wherein the actuator is configured to actively adjust the ankle-angle between the tibial member and the foot unit during the stance phase of the gait cycle.

19. The transfemoral prosthetic device of claim 1, wherein the first threshold is 2.5 degrees and the second threshold is 5 degrees.

20. A transfemoral prosthetic device associated with a limb, comprising:
   a foot unit;
   a tibial member pivotally attached to the foot unit to define an ankle joint;
   a femoral member pivotally attached relative to the tibial member to define a knee joint;
   an actuator operatively coupled to the ankle joint and configured to actively adjust an ankle-angle between the tibial member and the foot unit during at least a portion of a swing phase of a gait cycle;

at least one sensor disposed on the transfemoral prosthetic device and configured to generate data indicative of at least one of position or movement of the transfemoral prosthetic device during a gait of a user; and a processor communicatively coupled to the at least one sensor and configured to:

receive said generated data, determine the ankle-angle of the transfemoral prosthetic device and that the user is moving up an incline based at least in part on said generated data, determine ankle-angle adjustments based at least in part on determining that the user is moving up the incline and on said determined ankle-angle of the transfemoral prosthetic device satisfying an ankle-angle threshold, wherein the ankle-angle adjustments are based on an angular amount of the incline, wherein the ankle-angle adjustments comprise a first ankle-angle adjustment and a second ankle-angle adjustment, wherein the first ankle-angle adjustment is used for incline angular amounts greater than a first threshold but lower than a second threshold and the second ankle-angle adjustment is used for incline angular amounts greater than the second threshold;

generate a control signal based at least in part on said determined ankle-angle adjustments of the transfemoral prosthetic device, and actively adjust the ankle-angle of the transfemoral prosthetic device by actuating the at least one actuator operatively coupled to the ankle joint during at least a portion of the swing phase of the gait cycle based at least in part on said generated control signal.

21. A transfemoral prosthetic device associated with a limb, comprising:

a foot unit;

a tibial member pivotally attached to the foot unit to define an ankle joint;

a femoral member pivotally attached relative to the tibial member to define a knee joint;

an actuator operatively coupled to the ankle joint and configured to actively adjust an ankle-angle between the tibial member and the foot unit during at least a portion of a swing phase of a gait cycle;

at least one sensor disposed on the transfemoral prosthetic device and configured to generate data indicative of at least one of position or movement of the transfemoral prosthetic device during a gait of a user; and a processor communicatively coupled to the at least one sensor and configured to:

receive said generated data, determine the ankle-angle of the transfemoral prosthetic device and that the user is moving down a decline based at least in part on said generated data, determine ankle-angle adjustments based at least in part on determining that the user is moving down the decline and on said determined ankle-angle of the transfemoral prosthetic device satisfying an ankle-angle threshold, wherein the ankle-angle adjustments are based on an angular amount of the decline, wherein the ankle-angle adjustments comprise a first ankle-angle adjustment and a second ankle-angle adjustment, wherein the first ankle-angle adjustment is used for decline angular amounts greater than a first threshold but lower than a second threshold and the second ankle-angle adjustment is used for decline angular amounts greater than the second threshold;

generate a control signal based at least in part on said determined ankle-angle adjustments of the transfemoral prosthetic device, and actively adjust the ankle-angle of the transfemoral prosthetic device by actuating the at least one actuator operatively coupled to the ankle joint during at least a portion of the swing phase of the gait cycle based at least in part on said generated control signal.

* * * * *

UNITED STATES PATENT AND TRADEMARK OFFICE
CERTIFICATE OF CORRECTION

PATENT NO. : 10,195,057 B2
APPLICATION NO. : 13/244010
DATED : February 5, 2019
INVENTOR(S) : Arinbjörn Viggo Clausen It is certified that error appears in the above-identified patent and that said Letters Patent is hereby corrected as shown below:

On the Title Page

On Page 9, Column 2, Item (56), Line 47, under Other Publications, change "involving" to --(involving--.

In the Specification

In Column 34, Line 22, change "FIG." to --FIGS.--.

In Column 34, Line 64, change "the" to --The--.

In Column 39, Line 15, change "and or" to --and/or--.

In Column 45, Line 49, change "plantarfex" to --plantarflex--.

In Column 52, Line 16, change "may data may" to --data may--.

In the Claims

In Column 63, Lines 35-36, Claim 1, change "ankle angle" to --ankle-angle--.

In Column 63, Line 38, Claim 1, change "ankle angle" to --ankle-angle--.

In Column 64, Line 14, Claim 9, after "foot" insert --unit--.

In Column 64, Line 50, Claim 17, change "unit:" to --unit--.

Signed and Sealed this
Fourth Day of June, 2019

Andrei Iancu
*Director of the United States Patent and Trademark Office*